(12) United States Patent
Nordt, III et al.

(10) Patent No.: US 7,691,074 B2
(45) Date of Patent: *Apr. 6, 2010

(54) FLEXIBLE SUPPORT WITH JOINT-SPANNING DOUBLE HINGE

(75) Inventors: William E. Nordt, III, Charles City, VA (US); Ian D. Kovacevich, Charlotte, NC (US); Kevin J. Dahlquist, Charlotte, NC (US); Tom J. Philpott, Charlotte, NC (US)

(73) Assignee: Nordt Development Co., LLC, Charles City, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/933,329

(22) Filed: Oct. 31, 2007

(65) Prior Publication Data

US 2008/0065230 A1    Mar. 13, 2008

Related U.S. Application Data

(63) Continuation of application No. 11/160,384, filed on Jun. 21, 2005, which is a continuation-in-part of application No. 11/058,109, filed on Feb. 15, 2005, now abandoned.

(60) Provisional application No. 60/590,852, filed on Jul. 22, 2004, provisional application No. 60/590,946, filed on Jul. 22, 2004, provisional application No. 60/637,026, filed on Dec. 17, 2004.

(51) Int. Cl.
    *A61F 5/00* (2006.01)
(52) U.S. Cl. ............................... 602/16; 602/5; 602/20; 602/23; 602/26

(58) Field of Classification Search ..................... 602/5, 602/14, 19, 20, 23, 26, 6, 16, 60–63
See application file for complete search history.

(56) References Cited

U.S. PATENT DOCUMENTS 2,195,024 A    3/1940  Bullock
4,296,744 A    10/1981 Palumbo (Continued)

OTHER PUBLICATIONS

U.S. Appl. No. 11/160,381, filed Jun. 21, 2005, pending.

(Continued)

*Primary Examiner*—Patricia Bianco
*Assistant Examiner*—Keri J Nicholson
(74) *Attorney, Agent, or Firm*—Tillman Wright, PLLC; Chad D. Tillman; Jeremy C. Doerre

(57) ABSTRACT

A potentiating support for an area of a body includes: a framework having a surface for abutment with an area of a body including a hinge joint, the framework defining a plurality of permanent openings in the surface; and two strut members each attached to the framework such that each the strut member spans the hinge joint when the framework is disposed in abutment with the area of the body, the strut members providing a measure of rigidity to the framework in the direction of their respective lengths, each respective the strut member including an intermediate portion thereof spanning the hinge joint that is expandable and recoverable between a first initial state and extended states wherein, when expanded to a the extended state during flexing of the hinge joint, the respective strut member stores potential energy that is released as kinetic energy upon its return to the initial state.

19 Claims, 55 Drawing Sheets

U.S. PATENT DOCUMENTS

| | | | |
|---|---|---|---|
| 4,354,280 | A | 10/1982 | Hayes |
| 4,408,600 | A | 10/1983 | Davis |
| 4,453,271 | A | 6/1984 | Donzis |
| 4,700,698 | A | 10/1987 | Kleylein |
| 4,765,318 | A | 8/1988 | Tranberg et al. |
| 4,872,448 | A | 10/1989 | Johnson, Jr. |
| 4,884,561 | A | 12/1989 | Letson, Sr. |
| 5,154,690 | A | 10/1992 | Shiono |
| 5,226,192 | A | 7/1993 | Jones et al. |
| 5,277,697 | A | 1/1994 | France et al. |
| 5,288,287 | A | 2/1994 | Castillo et al. |
| 5,385,538 | A | 1/1995 | Mann |
| 5,399,153 | A | 3/1995 | Caprio et al. |
| 5,449,341 | A | 9/1995 | Harris |
| 5,451,201 | A | 9/1995 | Prengler |
| 5,537,689 | A | 7/1996 | Danctger |
| 5,606,745 | A | 3/1997 | Gray |
| 5,634,211 | A | 6/1997 | Chen |
| 5,730,710 | A | 3/1998 | Eichhorn et al. |
| 5,759,167 | A | 6/1998 | Sheilds et al. |
| 5,782,780 | A | 7/1998 | Mason et al. |
| 5,865,776 | A | 2/1999 | Springs |
| 5,921,945 | A * | 7/1999 | Gray ........................ 602/5 |
| 5,934,599 | A | 8/1999 | Hammerslag |
| 5,984,885 | A | 11/1999 | Gaylord et al. |
| 6,024,712 | A * | 2/2000 | Iglesias et al. ................ 602/6 |
| 6,065,152 | A | 5/2000 | Parker |
| 6,151,714 | A | 11/2000 | Pratt |
| 6,202,953 | B1 | 3/2001 | Hammerslag |
| 6,219,843 | B1 | 4/2001 | Passi et al. |
| 6,226,797 | B1 | 5/2001 | Tollini |
| 6,238,360 | B1 * | 5/2001 | Gildersleeve et al. ......... 602/26 |
| 6,258,014 | B1 | 7/2001 | Karecki |
| D448,084 | S | 9/2001 | Hopwood et al. |
| 6,289,558 | B1 | 9/2001 | Hammerslag |
| 6,383,156 | B1 * | 5/2002 | Enzerink et al. .............. 602/16 |
| 6,687,912 | B2 | 2/2004 | Collins et al. |
| 6,994,682 | B2 | 2/2006 | Bauerfeind et al. |
| 7,004,919 | B2 | 2/2006 | Gaylord et al. |
| D521,644 | S | 5/2006 | Nordt et al. |
| 7,237,270 | B2 | 7/2007 | Crye et al. |
| 2002/0095750 | A1 | 7/2002 | Hammerslag |
| 2003/0204938 | A1 | 11/2003 | Hammerslag |
| 2006/0156517 | A1 | 7/2006 | Hammerslag et al. |

OTHER PUBLICATIONS

U.S. Appl. No. 11/160,382, filed Jun. 21, 2005, pending.
U.S. Appl. No. 11/160,383, filed Jun. 21, 2005, pending.
U.S. Appl. No. 11/160,396, filed Jun. 22, 2005, pending.
U.S. Appl. No. 11/160,398, filed Jun. 22, 2005, pending.
U.S. Appl. No. 11/160,387, filed Jun. 21, 2005, pending.
U.S. Appl. No. 11/160,385, filed Jun. 21, 2005, pending.
U.S. Appl. No. 11/160,388, filed Jun. 21, 2005, pending.
U.S. Appl. No. 11/160,386, filed Jun. 21, 2005, pending.
U.S. Appl. No. 11/160,384, filed Jun. 21, 2005, pending.
U.S. Appl. No. 11/875,595, filed Oct. 19, 2007, pending.
U.S. Appl. No. 11/875,608, filed Oct. 19, 2007, pending.
U.S. Appl. No. 11/876,573, filed Oct. 22, 2007, pending.
U.S. Appl. No. 11/876,578, filed Oct. 22, 2007, pending.
U.S. Appl. No. 11/876,589, filed Oct. 22, 2007, pending.
U.S. Appl. No. 11/876,598, filed Oct. 22, 2007, pending.
U.S. Appl. No. 11/187,589, filed Jul. 22, 2005, pending.
U.S. Appl. No. 11/187,590, filed Jul. 22, 2005, pending.
U.S. Appl. No. 12/101,763, filed Apr. 11, 2008, pending.

* cited by examiner

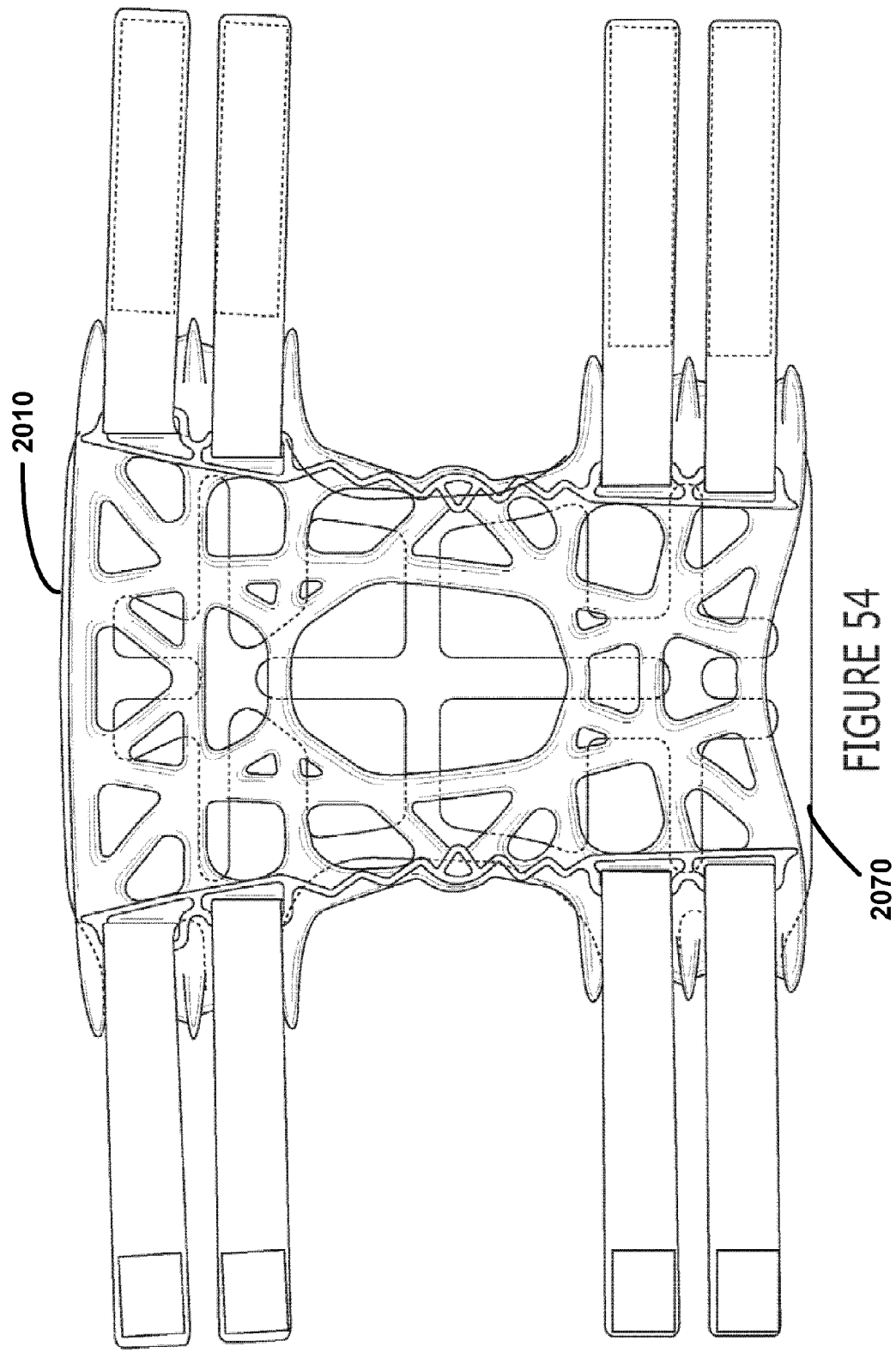

FLEXIBLE SUPPORT WITH JOINT-SPANNING DOUBLE HINGE

CROSS-REFERENCE TO RELATED APPLICATION

The present application claims all priority benefits under 35 U.S.C. §119 and §120 to the following, wherein the present application is a continuation patent application of U.S. nonprovisional patent application Ser. No. 11/160,384, filed Jun. 21, 2005, now U.S. Pat. No. 7,615,019, which '384 application published as US 2006-0030804 A1, and which '384 application is a continuation-in-part patent application of U.S. nonprovisional patent application Ser. No. 11/058,109, filed Feb. 15, 2005, abandoned, and which '384 application is a nonprovisional patent application of each of U.S. provisional patent application 60/590,852, filed Jul. 22, 2004, expired; U.S. provisional patent application 60/590,946, filed Jul. 22, 2004, expired; and U.S. provisional patent application 60/637,026, filed Dec. 17, 2004, expired.

Each of the foregoing patent applications and patent publications are incorporated herein by reference.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Joint fatigue, pain, and instability are common conditions of active and aging people. This is especially true with regard to hinge joints of the body, including the knee joint and the elbow joint. Such joint ailments often can be attributed to damages and degenerative wear in the contact surfaces of bone ends meeting at the joint. External support in these areas of the body can help address joint fatigue, pain, and/or instability and, generally, external support in various areas of the body can serve to address many different conditions. One or more aspects of the invention provides such support. Moreover, one or more aspects of the invention even augments motion about joints and, in particular, about hinge joints.

SUMMARY OF THE PRESENT INVENTION

The invention relates to various supports for the body and, with respect to certain embodiments, the invention relates to potentiating supports for hinge joints of the body. Indeed, certain supports are designed for the area of the knee and other supports are designed for the area of the elbow. These supports of the invention are useful for injury treatment or prevention, rehabilitation, and motion enhancement. For example, a preferred potentiating support for the knee provides a secure fitting and comfortable knee brace for the purposes of supporting knee alignment, comfort, and protection in the activities of daily living, athletics, and working and in the treatment or rehabilitation of an injured or ailing knee, all the while providing joint motion assistance for performance enhancement in everyday and athletic activities. In this regard, kinetic energy is stored and returned for use to assist the body in its natural knee movement in a preferred knee support of the present invention. Other preferred supports of the present invention include clothing have expandable and recoverable frameworks for support of areas of the body. Embodiments of these supports, as well as aspects and features of the invention, are set forth below and in the detailed description section herein.

FIRST ASPECT OF THE INVENTION

A first aspect of the invention generally relates to a support for an area of a body. Broadly described, the support includes an elastically stretchable framework for abutment with the area of the body and a fastening mechanism for securing the framework in its abutment with the area of the body. The framework defines a plurality of permanent openings therein regardless of whether the framework is secured in abutment with the area of the body. Furthermore, the fastening mechanism is connected to and applies tension at points proximate a perimeter of the framework such that the framework is expanded and tensioned in its abutment with the area of the body.

More specifically described, the framework of the support extends in generally first and second directions to define a surface of the framework for abutment with the area of the body when the framework is secured by the fastening mechanism. In particular, this surface of the framework is intended to abut an area of the body when the support is worn, such as a portion of an arm, leg, or torso. With reference to a cylindrical coordinate system, the framework of the support generally extends in a first axial direction and in a second circumferential direction to define a surface of the framework. The fastening mechanism further is connected to and applies tension at points along the framework, whereby the framework is expanded. Accordingly, the surface of the framework is tensioned in its abutment with the area of the body when the support is worn. Because the framework elastically stretches in its expansion in the axial and circumferential directions, the surface of the framework is generally shaped to fit an area of a leg, arm, or torso in its abutting engagement.

Continuing this description, the framework defines a plurality of permanent openings in the surface thereof regardless of whether the framework is secured with the surface in abutment with the area of the body. In this regard, the framework of the support comprises a structure of interconnected portions that define openings therein regardless of whether the support actually is worn. The interconnected portions completely bounding at least one of the openings are substantially similar in thickness and cross-section and, preferably, include a non-planar cross-section. This is in contrast to conventional wraps, in which a length of fabric that may be wrapped about the body for support may form a temporary framework having temporary openings. The framework and openings conventionally defined by the wrapped fabric are temporary because the framework and openings do not persist when the fabric is unwrapped. In contrast, the framework of this aspect is permanent, and openings defined therein are permanent, because neither the framework nor the openings are dependent upon the support actually being worn. The interconnected structure is permanent and, thus, the framework and openings defined by the structure are permanent.

The fastening mechanism generally secures the framework to the area of the body by partially or completely encircling the body with the support. In a feature of this aspect, the support only partially encircles the body when the framework is in abutment with the area of the body. Alternatively, the support fully encircles the body when the framework is in abutment with the area of the body.

In additional features of this aspect, a plurality of segments or members define the framework, with each of the members comprising a generally linear segment of an elastomeric material. The framework thus comprises a network of interconnected, generally linear members. Moreover, the members may be integrally formed through a conventional molding process. Alternatively, the members may be formed from the interconnection of preformed members. The permanent openings defined by the framework may have different configurations and dimensions, including oval and polygonal shapes, but the openings overall preferably are symmetrically disposed about an axis of symmetry of the framework.

In another feature of this aspect, openings in the surface of the framework do not extend entirely through the framework, thereby forming cavities in the surface. Alternatively, the surface in which the openings are defined comprises an inner surface of the support for disposition toward the body, and the openings extend completely through the framework to an outer surface of the framework. A benefit of the openings extending from inner to outer surfaces of the framework is that these openings may permit portions of the area of the body that are in abutting engagement with the framework to breathe, especially where the inner surface directly contacts the body and no intermediate member extends there between, such as a liner. The area of the openings in the surface of the framework to the surface area of the framework preferably has an "open air ratio" of 50% or greater.

In an additional feature of this aspect, the fastening mechanism includes a first fastening component connected to a first said side of the framework and another fastening component connected to a second said side of the framework. The two fastening components removably fasten directly to one another to fully encircle the body with the support and to secure the surface of the framework in its abutment with the area of the body. Alternatively, a band, sleeve, or clothing (hereinafter generally referred to as "garment") is disposed proximate (i.e., at or near) the area of the body, and the two fastening components each is adapted to removably fasten directly to the garment in order to at least partially encircle the body with the support and to secure the surface of the framework in its abutment with the area of the body. Furthermore, a portion of the garment may comprise a liner extending between the framework and the area of the body with which the framework abuts. If the garment comprises clothing, the garment may include, for example, a shirt, pants, or jumpsuit. Fastening of the fastening components may be accomplished through any fasteners or fastening means including, for example, cohesives; adhesives; hooks and loops for hook-and-loop coupling; one or more buttons and a row of buttonholes to provide adjustable and removable coupling; hook and eye fasteners; press-studs arrangements; laces and holes; holed belts and buckles; zippers; staples; tacks; clasps; toggles; and threaded connectors and turnbuckles, and the like and any equivalents thereof. The opposite sides to which the fastening components are connected may comprise areas that are generally proximate to the edges of the framework.

In an alternative to the aforementioned feature, the fastening mechanism includes first and second components connected to a first said side of the framework and third and fourth components connected to a second said side of the framework. The first and the third components removably fasten directly to one another, and the second and fourth components removably fasten directly to one another, to fully encircle the body with the support and to secure the surface of the framework in its abutment with the area of the body. Alternatively, a garment is worn about the area of the body, and the fastening components each is adapted to removably fasten directly to the garment in order to at least partially encircle the body with the support and to secure the surface of the framework in its abutment with the area of the body. Furthermore, a portion of the garment may comprise a liner extending between the framework and the area of the body with which the framework abuts. If the garment comprises clothing, the garment may include, for example, a shirt, pants, or jumpsuit. Fastening of the fastening components may be accomplished through fasteners. The opposite sides to which the fastening members are connected may comprise edges of the framework or areas generally proximate to the edges of the framework.

In another feature of this aspect, the framework extends across a joint of the body, and, because of its overall elastic stretchability, the framework stores energy as the joint is flexed and the framework releases the stored energy as the joint is extended. In particular, the framework preferably includes one or more expandable and recoverable portions or members that, as the joint is flexed, are increasingly tensioned and lengthen, thereby storing kinetic energy as potential energy; and that, as the joint is extended, are decreasingly tensioned and shortened, thereby releasing potential energy as kinetic energy.

In yet another feature of this aspect, the support may include one or more additional tensioning members for adjustably applying additional tension to the framework. Such an additional tensioning member preferably comprises a crank having tensioning lines that are attached to the framework for adjustably applying additional tension to the framework for elastically stretching the framework in controlled, defined increments.

In still yet additional features of this aspect, the framework of the support is exposed (i.e., not covered); has no internal cavity (i.e., solid); and includes a generally four-sided perimeter.

SECOND ASPECT OF THE INVENTION

A second aspect of the invention relates to a method of donning a support for an area of a body. The method includes the steps of positioning an elastically stretchable framework in abutment with an area of a body; applying tension at points along opposite sides of the framework such that the framework is expanded and the surface of the framework is tensioned in its abutment with the area of the body; and securing the tensioned framework in its forced abutment with the area of the body using a fastening mechanism. The framework defines a plurality of permanent openings therein regardless of whether the support is donned.

In a feature of this aspect, the fastening mechanism applies tension at points along opposite sides of the framework, and an amount of tension applied to a first portion or member of the framework extending from a point along a said side of the framework differs from an amount of tension applied to a second portion or member of the framework extending from another point along the same said side of the framework. In a similar feature, the fastening mechanism applies tension at points along opposite sides of the framework, and an amount of tension applied to a first group of members extending from a point along a said side of the framework differs from an amount of tension applied to a second group of members extending from another point along the same said side of the framework.

In yet another feature of this aspect of the invention, the step of positioning the framework in abutment with the area of the body includes the step of slipping the support over a terminal end of an arm or leg of the body, such as pulling the support over a hand or foot. Alternatively, step of positioning the framework in abutment with the area of the body includes the step of wrapping the support over the area of the body without slipping the support over a terminal end of a leg or arm of the body.

THIRD ASPECT OF THE INVENTION

A third aspect of the invention generally relates to a support for an area of a body. Broadly described, the support includes an elastically stretchable framework, a garment, and a fastening mechanism that secures the framework to the area of the body when the support is worn. The framework defines a plurality of permanent openings therein regardless of whether the framework is secured in its abutment with the area of the body. Furthermore, the fastening mechanism applies tension at points such that said framework is expanded and tensioned in its abutment with the area of the body. The fastening mechanism of this aspect further works in conjunction with the garment. The garment is worn proximate the area of the body with which the surface of the framework abuts, and the fastening mechanism fastens directly to the garment.

More specifically described, the framework of the support extends in generally first and second directions to define a surface of the framework for abutment with the area of the body when the framework is secured by the fastening mechanism. In particular, this surface of the framework is intended to abut an area of the body when the support is worn, such as a portion of an arm, leg, or torso. With reference to a cylindrical coordinate system, the framework of the support generally extends in a first axial direction and in a second circumferential direction to define a surface of the framework. The fastening mechanism further is connected to and applies tension at points along the framework, whereby the framework is expanded. Accordingly, the surface of the framework is tensioned in its abutment with the area of the body when the support is worn. Because the framework elastically extends in axial and circumferential directions, the surface of the framework is generally shaped to fit an area of a leg, arm, or torso in its abutting engagement.

Continuing this description, the framework defines a plurality of permanent openings in the surface thereof regardless of whether the framework is secured with the surface in abutment with the area of the body. In this regard, the framework of the support defines openings therein regardless of whether the support actually is worn. The framework is permanent, and the openings defined therein are permanent, because neither the framework nor the openings are dependent upon the support actually being worn. The structure is permanent and, thus, the framework and openings defined by the structure are permanent.

In an additional feature of this aspect, the fastening mechanism includes a first component connected to a first of the opposite sides of the framework and a second component connected to a second of the opposite sides of the framework, and each of the fastening components is adapted to removably fasten to the garment. Alternatively, the fastening mechanism includes first and second components connected to a first of the opposite sides of the framework and third and fourth components connected to a second of the opposite sides of the framework, and each of these fastening components is adapted to removably fasten to the garment.

The garment comprises a band, sleeve, or clothing. The garment preferably is designed to extend about an area of an arm, leg, or torso of the body.

In a feature of this aspect, a portion of the garment comprises a liner for the framework. Moreover, the liner may be attached directly to the framework, may be indirectly attached to the framework, or may not be attached to the framework other than through fastening of the fastening components to the garment. The liner also may define openings therein that extend there through, thereby permitting ventilation of the area of the body with which the framework abuts. Moreover, the configuration of the openings in the liner may correspond and register with a configuration of the openings in the framework. In lieu of openings in the liner, or in addition thereto, the liner may be formed from a material that is permeable to air.

FOURTH ASPECT OF THE INVENTION

A fourth aspect of the invention relates to a method of donning a support for an area of a body. The method includes the steps of: positioning a garment proximate an area of a body; positioning a framework in abutment with the area of the body; applying tension at points of attachment to the framework whereby the framework is expanded and the framework is tensioned in its abutment with the area of the body; and fastening each of the fastening components to the garment while applying tension to the framework to secure the tensioned framework in its forced abutment with the area of the body. The framework defines a plurality of permanent openings therein regardless of whether the support is donned, and tension is applied by pulling on one or more fastening components that are anchored at one or more points to the framework.

FIFTH ASPECT OF THE INVENTION

A fifth aspect of the invention relates to a support for an area of a body and, in particular, to clothing having such a support. The clothing is dimensioned to fit a body. The support includes a framework that is attached to a portion of the clothing for abutment with and support of the area of the body when the clothing is worn. The framework defines a plurality of openings in the surface that preferably extend completely through the framework.

The clothing may comprises a sleeve such as, for example, an elbow sleeve, a forearm sleeve, a shin sleeve, a shirt, pants, or a jumpsuit. The clothing may be woven or knit, for example, and may be formed from cotton or a synthetic material such as nylon or polyester. Moreover, the clothing itself may be elastically stretchable. The framework is attached to the clothing by welding such as, for example, by plasticized welding or elastomeric welding. Additionally, the framework may be attached to the clothing by an adhesive or by sewing.

In a feature of this aspect, the framework extends over and is permanently attached to the clothing whereby the framework does not directly contact the area of the body. In this regard, a portion of the clothing (which extends beneath the framework) comprises a liner of the surface of the framework. The liner may be permeable to air, and the liner may define openings therein for exposing part of the supported area of the body. If the liner includes openings, then the openings in the liner preferably register with the openings in the framework for exposing portions of the supported area when the clothing is worn.

In another feature of this aspect, the opening of the framework is dimensioned to receive extending therein a joint protuberance of the body, such as a joint protuberance of an elbow or knee.

In yet additional features of this aspect, the framework comprises a unitary construction of a variable density material; and, the framework comprises an integral piece molded from elastomeric material. Moreover, the integral piece may include, molded therein, one or more separately molded pieces serving as strut members, and the strut members may include openings therein.

In another feature of the present invention, the framework comprises a plurality of expandable and recoverable members. Furthermore, at least one of the expandable members is arranged to increasingly be tensioned and lengthen, thereby storing kinetic energy as potential energy, as a joint of the body is flexed; and is arranged to decreasingly be tensioned and shorten, thereby releasing potential energy as kinetic energy, as the joint is extended.

SIXTH ASPECT OF THE INVENTION

A sixth aspect of the invention relates to a support for an area of a body that includes a liner. In particular, the support includes an elastically stretchable framework, a fastening mechanism for securing the framework in abutment with the area of the body by generally encircling the body by the support, and a liner attached to the framework for disposition between the framework and the area of the body to be supported. The framework defines a plurality of permanent openings that extend completely through the framework. The fastening mechanism is connected to and applies tension at points along opposite sides of the framework such that the framework is expanded into tensioned abutment with the area of the body. In accordance with this aspect of the invention, the liner defines at least two openings that register with the openings in the surface of the framework for exposing the area of the body to be supported. The liner may be woven or knit, and may be formed from cotton or a synthetic material, such as nylon or polyester.

In features of this aspect, the liner is permanently attached to the framework such as, for example, by plasticized welding or elastomeric welding; the liner is attached to the framework by an adhesive; and the liner is attached to the framework by sewing.

In another feature of this aspect, the liner does not include an opening for every opening in the framework, whereby a portion of the liner is exposed through an opening in the framework.

In another feature, the liner is permeable to air.

In still yet another feature of this aspect, both a particular opening in the framework and a particular opening in the liner registering with the particular opening in the framework are dimensioned to receive therein a joint protuberance of the body when the support extends across, i.e., spans, a joint of the body. The joint may comprise an elbow or a knee. The particular openings through which the joint protuberance is received serves to maintain the support in a proper orientation relative to the joint when the support is worn.

In another feature of this aspect, the support includes a sleeve and the liner comprises a portion of the sleeve that extends proximate the surface of the framework. Furthermore, the portion of the sleeve defining the liner may be attached to the framework about a perimeter of the portion of the sleeve. Additionally, the sleeve may include a band that extends between and that is attached to opposite sides of the framework. Moreover, the fastening mechanism may include fastening components attached to the framework, and the fastening components may be adapted to be removably fastened to the band.

SEVENTH ASPECT OF THE INVENTION

A seventh aspect of the invention relates to a support for an area of a body having an alignment opening for orientation of the support relative to a joint protuberance of the body. In accordance with this aspect, the support includes an elastically stretchable framework for abutment with the area of the body and a fastening mechanism for securing the framework in its abutment with the area of the body by generally encircling the body by the support. The framework defines a plurality of permanent openings regardless of whether the surface is in abutment with the area of the body. The fastening mechanism is connected to and applies tension at points along opposite sides of the framework such that the framework is expanded into tensioned abutment with the area of the body. A particular opening of the framework is an alignment opening that extends completely through the framework and is dimensioned to receive therein a joint protuberance of the body. The alignment opening serves to maintain the support in a proper orientation relative to the joint when the support is worn.

In features of this aspect, the alignment opening is symmetrically disposed about an axis extending along the first direction and the alignment opening is disposed generally equidistant from edges of the opposite sides of the framework that extend along the first direction. Furthermore, out of the openings defined in the framework, the alignment opening preferably comprises the largest opening that is defined by the framework.

In still yet another feature, the support includes an elastically stretchable liner attached to the framework for disposition between the surface of the framework and the area of the body to be supported, and the alignment opening is dimensioned to receive therethrough the joint protuberance covered by the liner. Alternatively, the liner defines an opening that registers with the alignment opening of the framework, and the joint protuberance extends within both the opening in the liner as well as the alignment opening in the framework.

In another feature of this aspect, the support further includes an alignment member that can be disposed between the framework and body for receiving therein the joint protuberance. The alignment member is contoured to receive the joint protuberance and, preferably, the alignment member comprises a ring whereby pressure is applied to the supported area of the body by the alignment ring along a perimeter of the alignment member.

The alignment member may be removably positionable between a liner and the surface of the framework, and the framework and the alignment member preferably are adapted for insertion and withdrawal of the alignment member through the alignment opening, even when the support is donned. The alignment member further may be dimensioned to at least partially extend within the alignment opening of the framework when the joint protuberance is received by the alignment member. The alignment member also preferably includes a portion contoured to receive part of the framework for securing the alignment member relative to the alignment opening, and preferably includes fingers that extend within a plurality of the openings in the framework for securing the alignment member relative to the alignment opening.

Alternatively, the liner is adapted to secure the alignment member in registry with the alignment opening at a surface of the liner facing away from the framework. In this regard, the liner preferably includes a pocket in which the alignment member is received for securing the alignment member in registry with the alignment opening, the liner extending between the alignment opening and the alignment member.

EIGHTH ASPECT OF THE INVENTION

An eighth aspect of the invention relates to a support for an area of a body that includes a removable member for receiving a joint protuberance of the body. In accordance with this aspect, the support includes an elastically stretchable framework for abutment with the area of the body and a fastening mechanism for securing the framework. The framework defines a permanent opening therein regardless of whether the support is donned. The permanent opening extends completely through the framework. The fastening mechanism is connected to and applies tension at points along opposite sides of the framework such that the framework is expanded and tensioned in its abutment with the area of the body. A member that is separate and removable from the framework is positionable proximate to the permanent opening of the framework for disposition between the permanent opening of the framework and the area of the body to be supported. The removable member is specifically contoured to receive a joint protuberance of the body, such as a protuberance of a knee or an elbow.

In various features of this aspect, the permanent opening in the framework is symmetrically disposed about the opposite sides of the framework; the permanent opening is dimensioned to receive a protuberance of the knee and comprises a patellar ring; the permanent opening is dimensioned to receive a protuberance of the elbow; the removable member comprises an alignment ring that applies pressure to the supported area of the body along a perimeter of the alignment ring; and the removable member extends within the permanent opening in the framework.

In another feature of this aspect, the framework comprises interconnected members that define a plurality of permanent openings in addition to the first permanent opening, and the removable member is further contoured to receive an interconnected member of the framework for securing the removable member relative to the first permanent opening during abutment of the framework with the body. In this regard, the removable member extends within the first permanent opening of the framework.

In yet another feature of this aspect, the framework defines a plurality of permanent openings in addition to the first permanent opening, and the removable member extends within the additional openings of the framework for securing an orientation of the removable member relative to the first permanent opening during abutment of the framework with the body. In this regard, the removable member may include fingers that extend within the additional openings for securing the removable member in an orientation relative to the first permanent opening of the framework.

In still yet another feature of this aspect, the support includes a liner attached to the framework for disposition between the surface of the framework and the area of the body to be supported, and the liner includes a pocket in which the removable member is received for securing the removable member relative to the framework. Alternatively, the support includes a liner attached to the framework for disposition between the surface of the framework and the area of the body to be supported, and the removable member is disposed between the liner and the surface of the framework. In this regard, the framework and the removable member preferably are adapted for insertion and withdrawal of the removable member through the permanent opening in the framework, even when the support is donned.

NINTH ASPECT OF THE INVENTION

A ninth aspect of the invention relates to a support for an area of a body having struts for increased rigidity in selected areas of an otherwise elastically stretchable framework of the support. In accordance with this aspect, a support for an area of a body includes an elastically stretchable framework and a fastening mechanism for securing the framework in its abutment by generally encircling the body by the support. The framework extends in generally first and second directions to define a surface of the framework for abutment with the area of the body. The fastening mechanism is connected to and applies tension at points of attachment disposed along opposite sides of the framework that extend in the first direction such that the framework is expanded in the second direction and the surface of the framework is tensioned in its abutment with the area of the body. Strut members extend generally in the first direction to increase rigidity of the sides of the framework along the first direction. Moreover, with reference to cylindrical coordinates, the first direction preferably comprises an axial direction and the second direction preferably comprises a circumferential direction.

The strut members are attached to, or embedded in, the framework or to the fastening mechanism, or are formed as part of the framework. If attached to the framework or to the fastening mechanism, the strut members may be attached through welding, including either plasticized or elastomeric welding. The strut members also may be attached by adhering the strut members.

In features of this aspect, a strut member has a cross-sectional dimension that varies along the strut member in the first direction; a strut member includes a middle portion and two end portions, wherein a cross-sectional area of the middle portion is less than the cross-sectional area of either end portions, whereby the strut member is more flexible in the middle portion than along the end portions; a strut member includes a middle portion thereof that is more susceptible to hinging movement than other portions thereof, and a strut member has a density that varies along the first direction, decreasing toward the middle portion, such that the strut member is more flexible in the middle portion than along the end portions.

In another feature of this aspect, the framework comprises interconnected portions, segments or members formed from an elastomeric material, each strut member is formed from an elastomeric material, and elastic members forming the framework have a greater elastic stretchability than the elastic stretchability of the strut members. Furthermore, the framework may comprise an integral piece formed in a conventional molding process, or may comprise preformed members that are connected together. The framework also may comprises an integral piece molded from elastomeric material that includes, separately molded and embedded therein, one or more pieces constituting strut members.

In addition to the aforementioned aspects and features of the invention, it should be noted that the invention further includes the various possible combinations of such aspects and features. Instances of such combinations are illustrated in the detailed description set forth below, for example.

BRIEF DESCRIPTION OF THE DRAWINGS

Several embodiments of the invention will now be described in detail with reference to the accompanying drawings, wherein similar elements are referred to with similar reference numerals.

FIG. 54 is a front elevational view of a nineteenth support in accordance with an aspect of the invention.

DETAILED DESCRIPTION OF THE PREFERRED EMBODIMENTS

Figure 1:
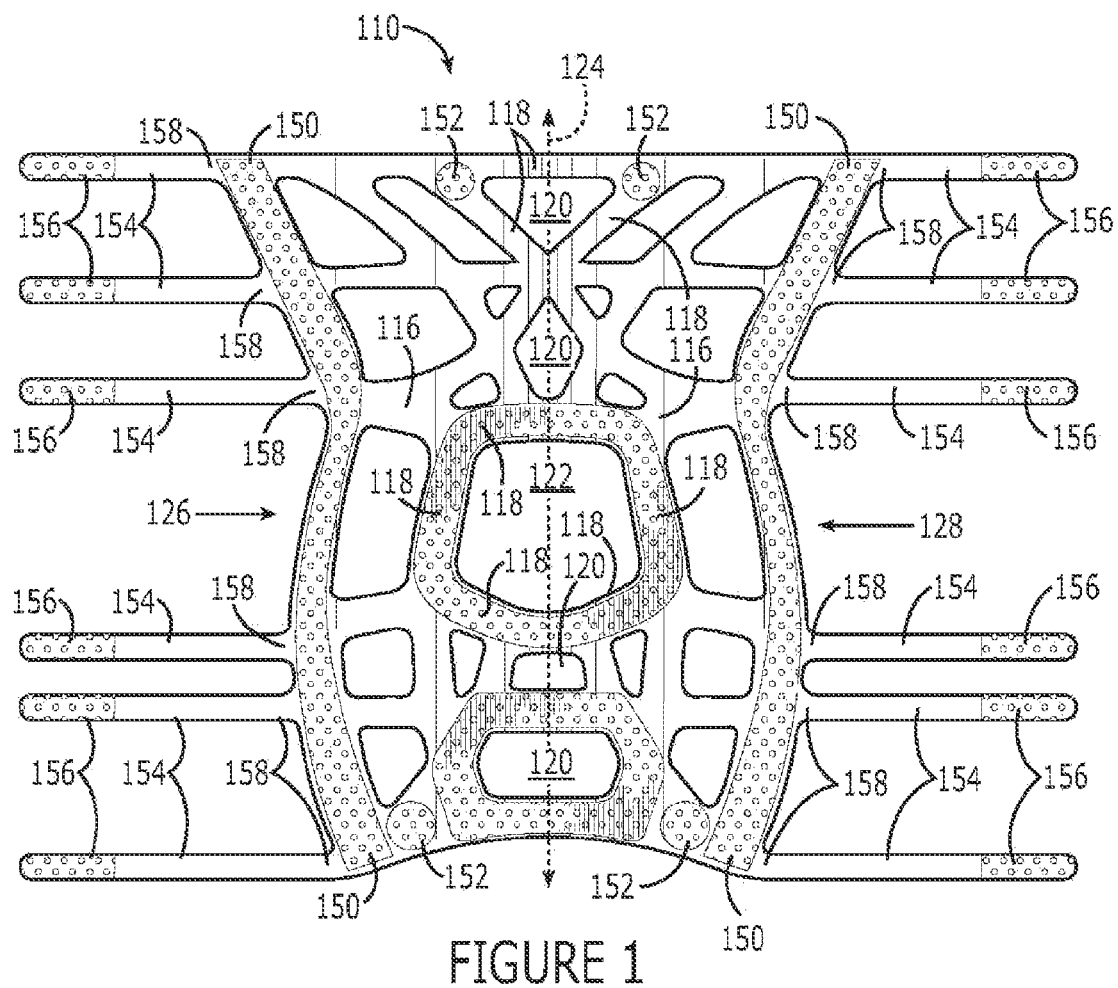
FIG. 1 is a top plan view of components of a first support in accordance with an aspect of the invention.

As a preliminary matter, it will readily be understood by one having ordinary skill in the relevant art ("Ordinary Artisan") that the invention is susceptible of broad utility and application. Furthermore, any embodiment discussed and identified as being "preferred" is considered to be part of a best mode contemplated for carrying out one or more aspects of the invention. Other embodiments also may be discussed for additional illustrative purposes in providing a full and enabling disclosure of the invention. Moreover, many embodiments, such as adaptations, variations, modifications, and equivalent arrangements, will be implicitly disclosed by the embodiments described herein and fall within the scope of the invention.

Accordingly, while the invention is described herein in detail in relation to one or more embodiments, it is to be understood that this disclosure is illustrative and exemplary of the invention, and is made merely for the purposes of providing a full and enabling disclosure of the invention. The detailed disclosure herein of one or more embodiments is not intended, nor is to be construed, to limit the scope of patent protection afforded the invention, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent a clear indication otherwise. Indeed, the steps in such processes or methods generally may be carried out in various different sequences and orders while still falling within the scope of the invention. Accordingly, it is intended that the scope of patent protection afforded the invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at lease one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

General Characteristics of Inventive Supports

In accordance with the invention, many of the inventive supports each includes a framework having a surface for abutment with an area of a body. The framework extends in generally first and second directions to define a surface of the framework for abutment with the area of the body. With reference to a cylindrical coordinate system, the framework of the support generally extends in a first axial direction and in a second circumferential direction to define the surface of the framework, which is intended to abut an area of the body when the support is worn, such as a portion of an arm, leg, or torso. Because the framework extends in axial and circumferential directions, the surface of the framework generally is shaped to fit an area of a leg, arm, or torso in its abutting engagement with the body. Furthermore, in many preferred embodiments, the support spans and supports an area that includes a hinge joint of the body and, in such embodiments, the support comprises a potentiating support for the hinge joint. As used herein, a "hinge joint" refers to a knee joint or an elbow joint and is characterized in that the joint provides hinging movement that is generally limited to being within a plane.

In further accordance with the invention, the framework is formed from one or more elastomeric materials such that the framework is expandable and recoverable. As used herein, "elastomeric material" refers to "a material that is capable of being easily expanded and resuming former shape." Something that has the ability to resume its former shape after expansion or compression is referred to herein as being "recoverable." Something that is expandable and recoverable also is referred to herein as being "elastically stretchable." This is in contrast to something that is "resilient," which refers to having "the ability to resume its former shape after compression." Preferably, the framework also is flexible and is capable of conforming to the general area of the body to be supported without substantial stretching; however, it is contemplated within the invention that the framework may need to be stretched in order to conform to the general area of the body to be supported. As used herein, "flexible" refers to "the ability to bend freely and repeatedly without breaking."

Still in accordance with the invention, the framework defines at least one permanent opening in a surface thereof regardless of whether the support is donned and regardless of whether the surface of the framework is in abutment with the area of the body to be supported. The at least one opening is bounded by the framework and, preferably, the at least one opening extends completely through the framework from an inner surface of the framework, when disposed in abutment with the area of the body to be supported, to an outer surface of the framework. Furthermore, when the support is donned, the framework along its entire boundary with the at least one opening is elastically stretchable between a first initial state and extended states and, when expanded to a said extended state, the framework stores potential energy that is released as kinetic energy upon its return to the initial state. In certain preferred embodiments, interconnected segments of elastomeric material constitute the framework, with the interconnected segments defining these permanent openings in the framework. The interconnected segments may be integrally formed through conventional molding processes or, alternatively, the interconnected segments may be constructed from the joining of segments that are preformed from elastomeric material. Each segment preferably comprises a generally linear segment. A benefit of these openings extending from inner to outer surfaces of the framework is that these openings thereby permit ventilation of portions of the area of the body that are in abutting engagement with the framework. Indeed, the area of the openings to the surface area of the framework preferably has an "open air ratio" of 50% or greater. However, in alternative embodiments that are not shown, the openings in the surface of the framework may not extend entirely through the framework. In such embodiments, the openings comprise cavities formed in the surface of the framework.

With reference to all but the illustrated embodiments of the invention discussed with reference to FIGS. 40-47, each of the illustrated embodiments of the support generally includes both the expandable and recoverable framework and a fastening mechanism that is connected to and applies tension at points of attachment to the framework such that the framework is expanded and tensioned in its abutment with the area of the body. The fastening mechanism generally secures the framework to the area of the body by partially or completely encircling the body with the support. The inventive support in each of these illustrated embodiments further preferably includes struts that provide a degree of rigidity to the support, especially proximate a perimeter of the framework. In this regard, the framework—in addition to being flexible and elastically stretchable—also preferably is "semirigid," in that the framework is "rigid in some degree or in some parts or portions thereof." The struts may be attached to or integrally formed with the framework. The framework itself also may be constructed to have a degree of rigidity while still being flexible and elastically stretchable in accordance with the present invention.

ILLUSTRATED EMBODIMENTS OF THE INVENTIVE SUPPORT

With particular reference to the drawings, various exemplary embodiments of one or more of the aforementioned aspects of the invention are illustrated.

Figure 7:
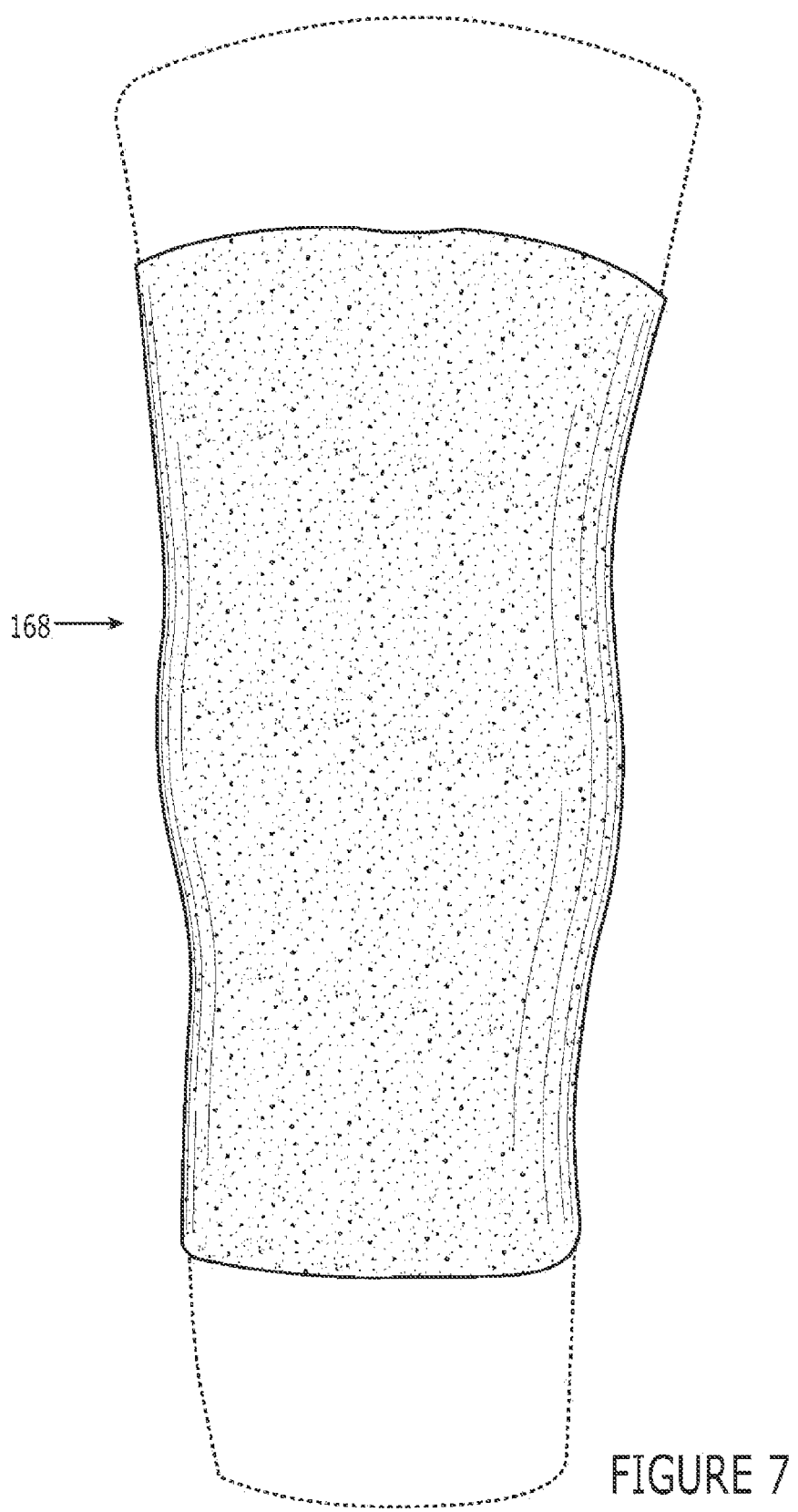
FIG. 7 is a front elevational view of a component of a second support in accordance with an aspect of the invention.
Figure 8:
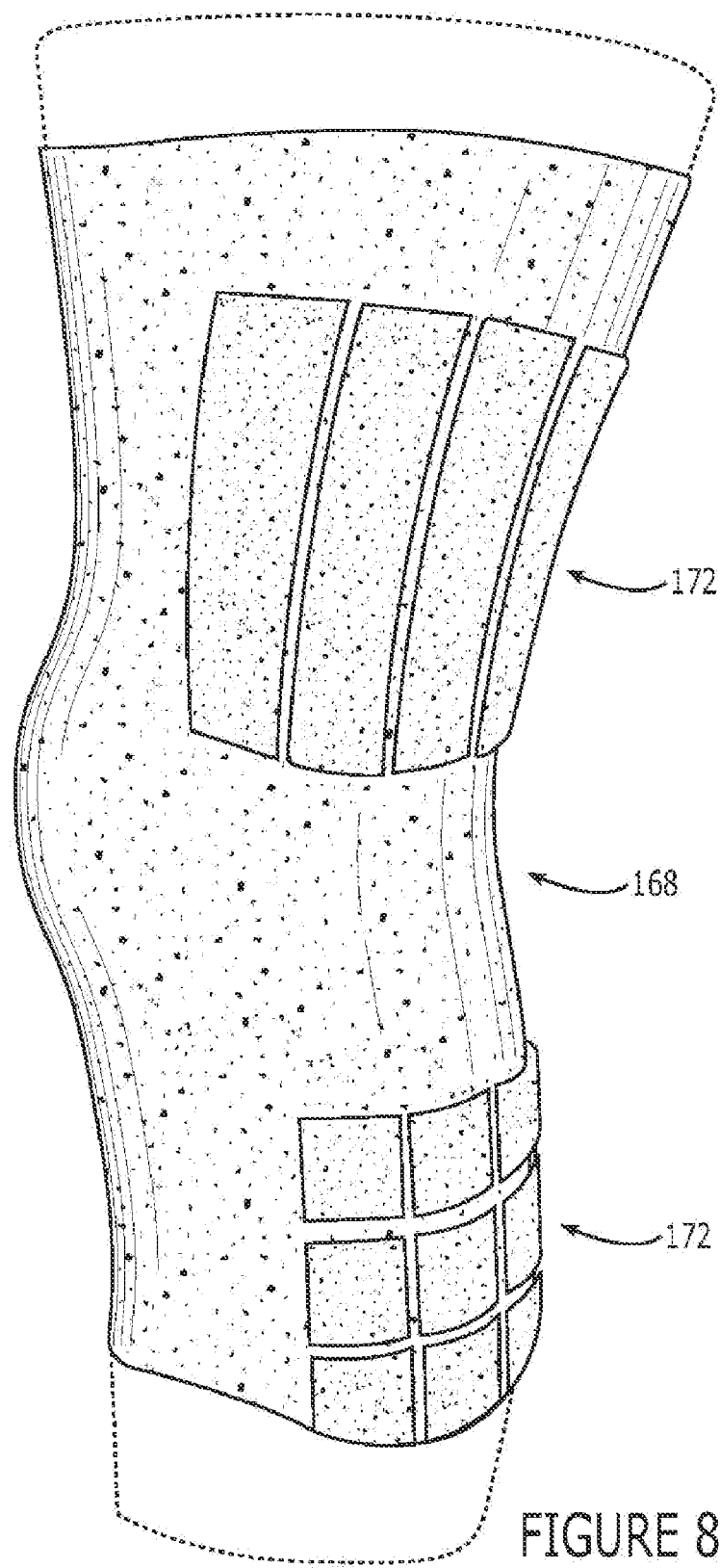
FIG. 8 is a back elevational view of a variation of the component of FIG. 7.
Figure 9:
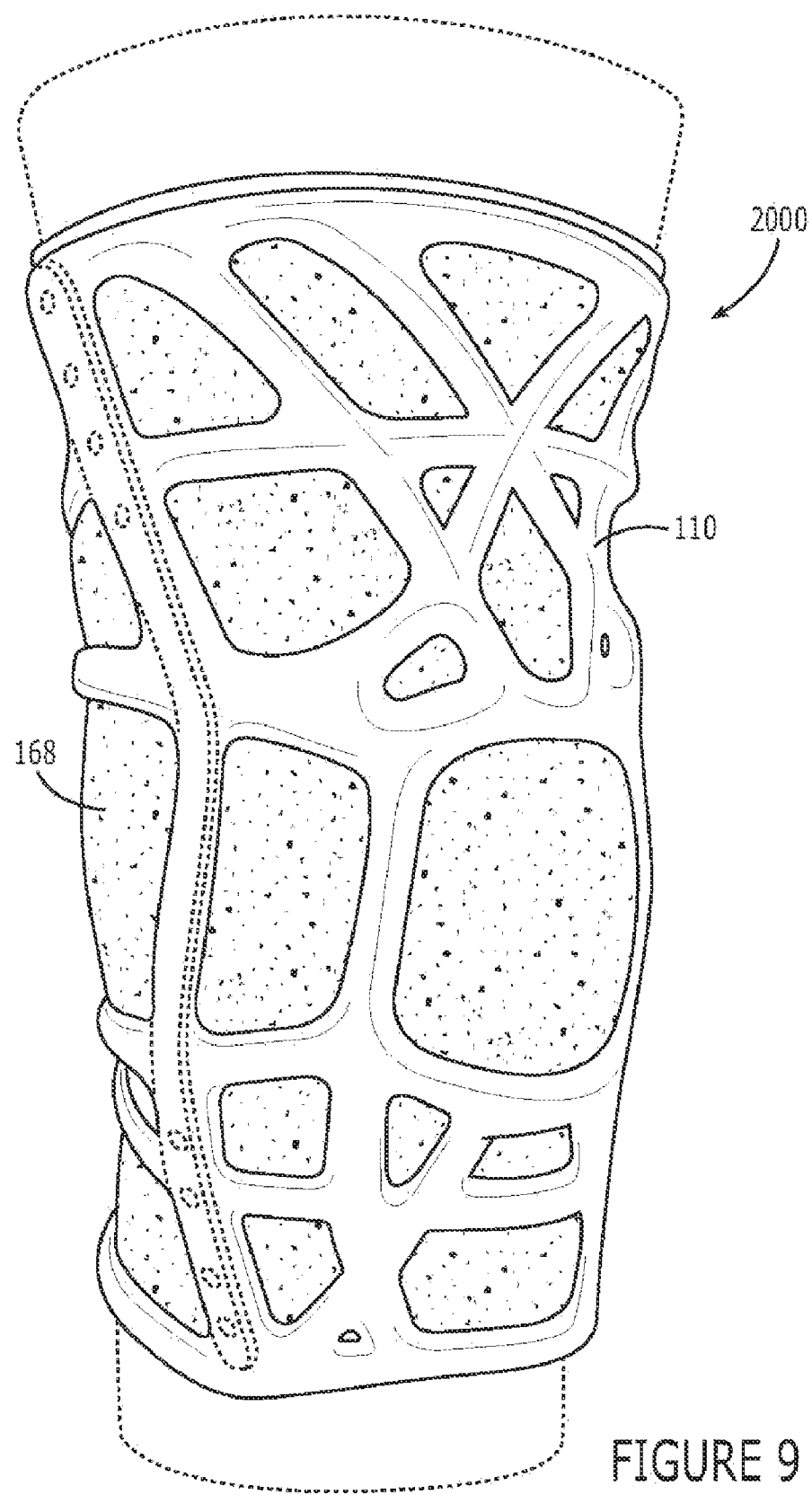
FIG. 9 is a front elevational view of the second support.
Figure 20:
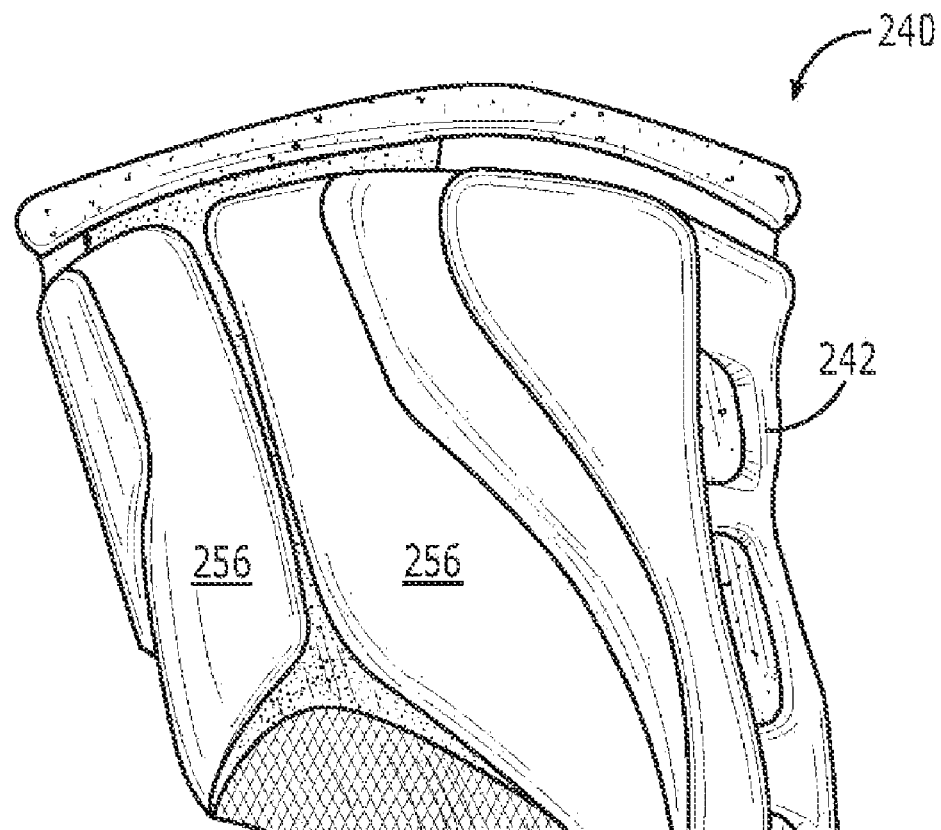
FIG. 20 is a back elevational view of the fourth support.
Figure 21:
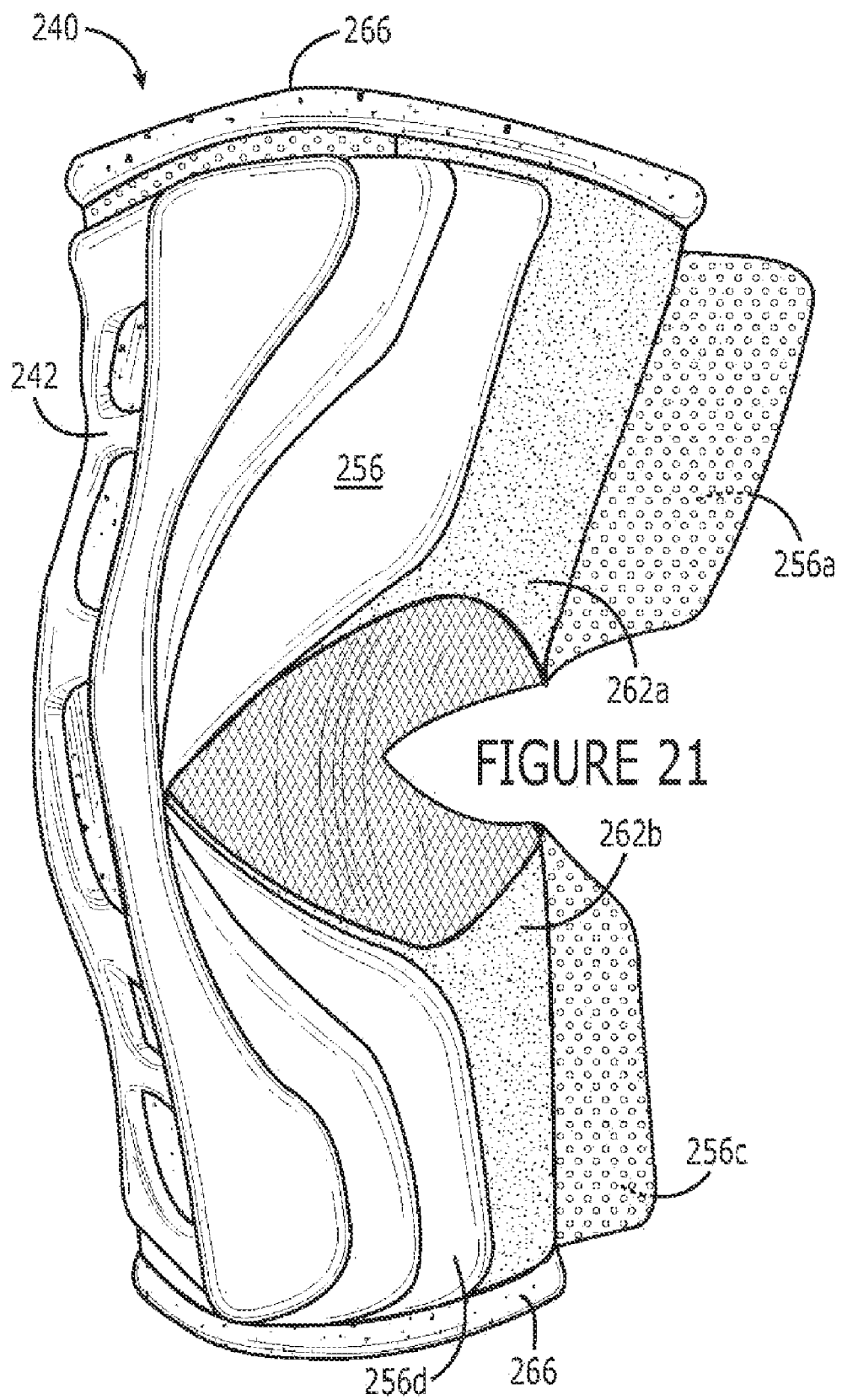
FIG. 21 is another back elevational view of the fourth support.
Figure 22A:
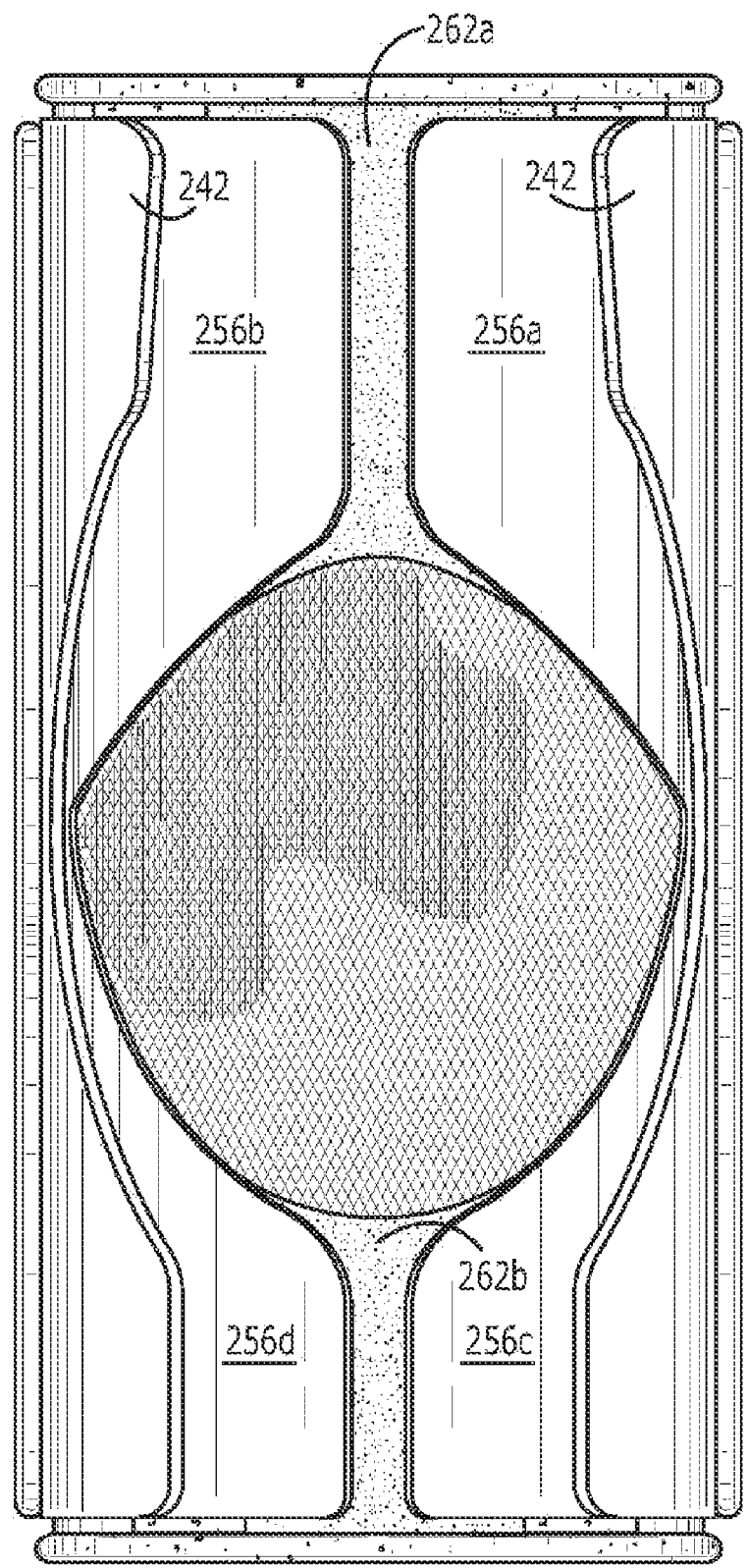
FIG. 22A is a back plan view of the fourth support.
Figure 22B:
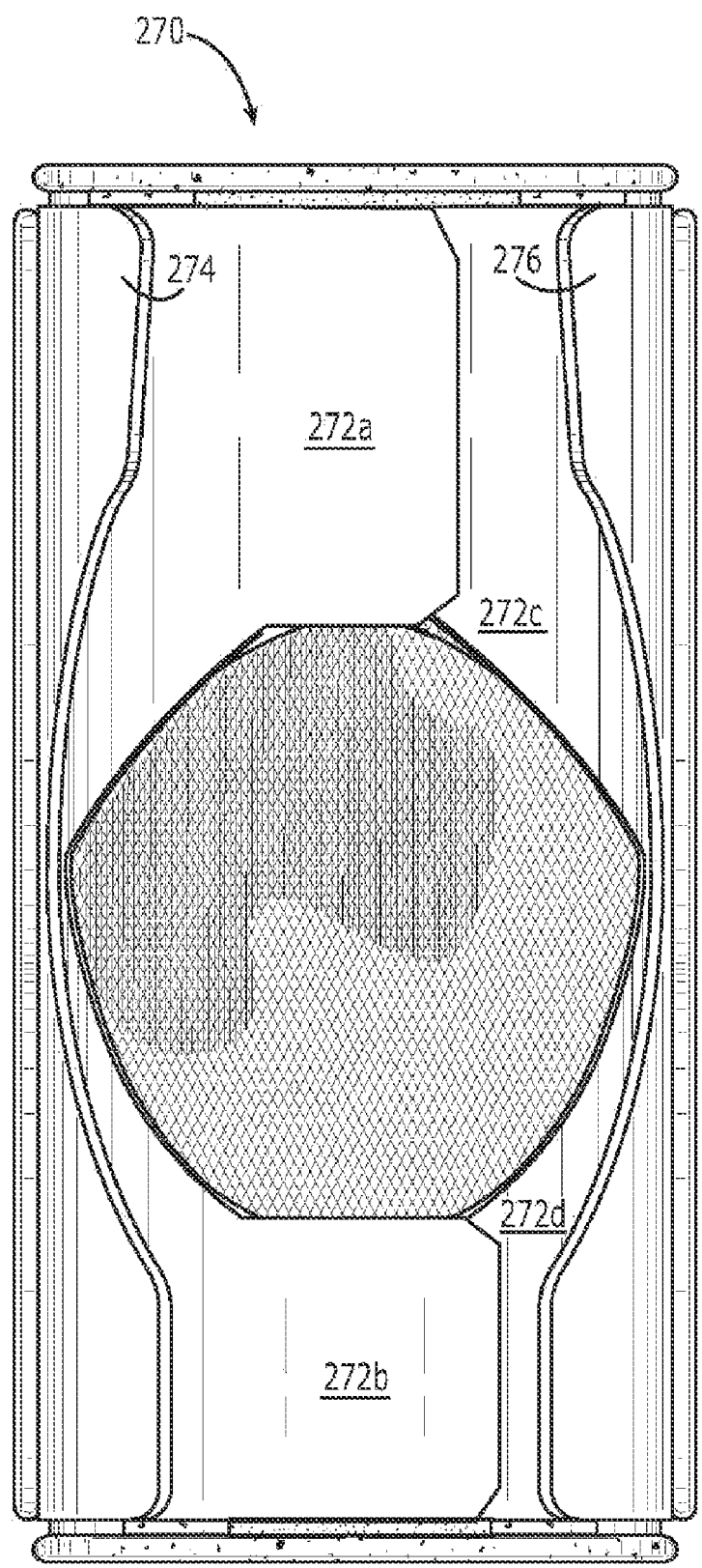
FIG. 22B is a back plan view of an alternative feature of the fourth support.
Figure 23:
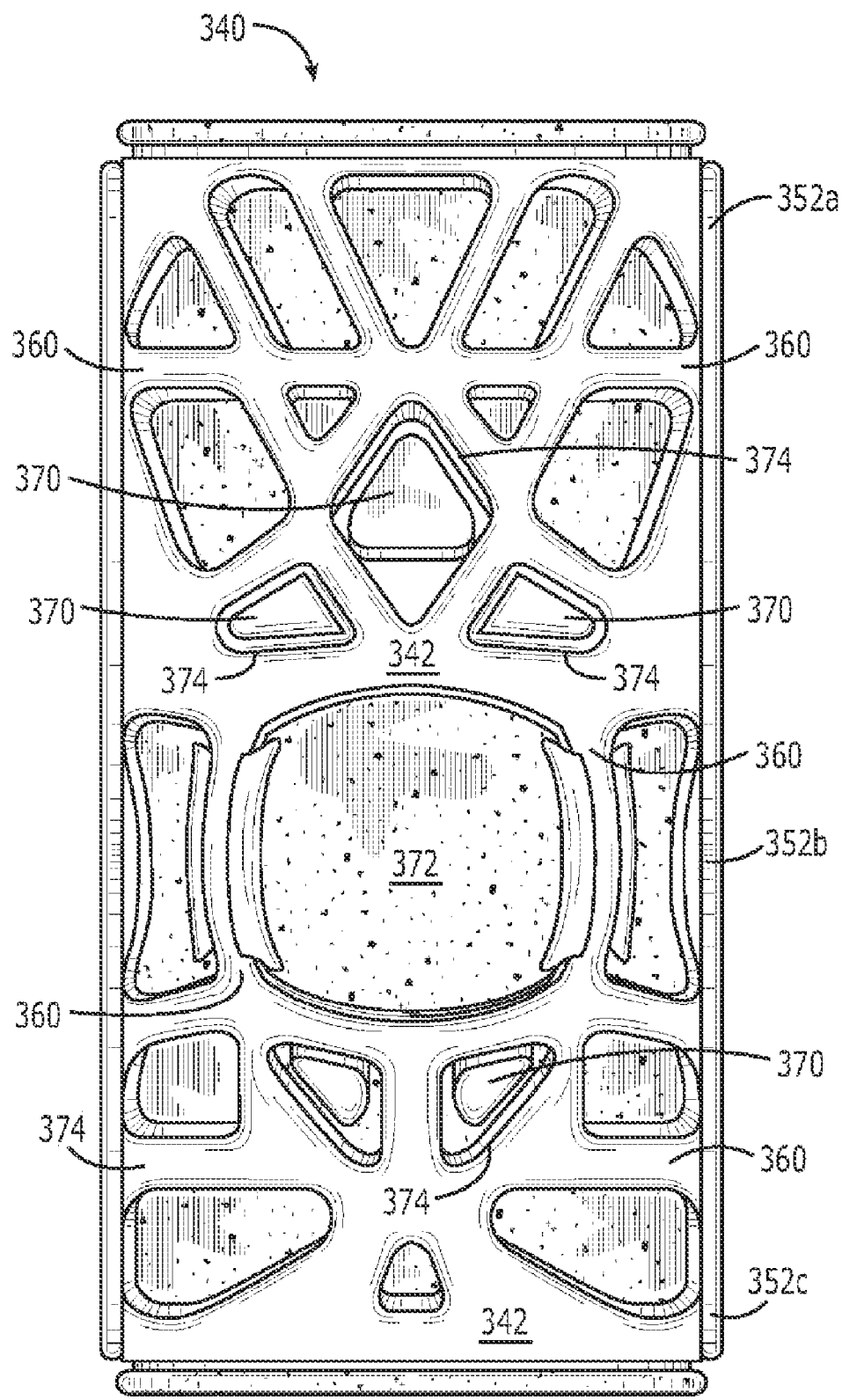
FIG. 23 is a front plan view of a fifth support in accordance with an aspect of the invention.
Figure 24:
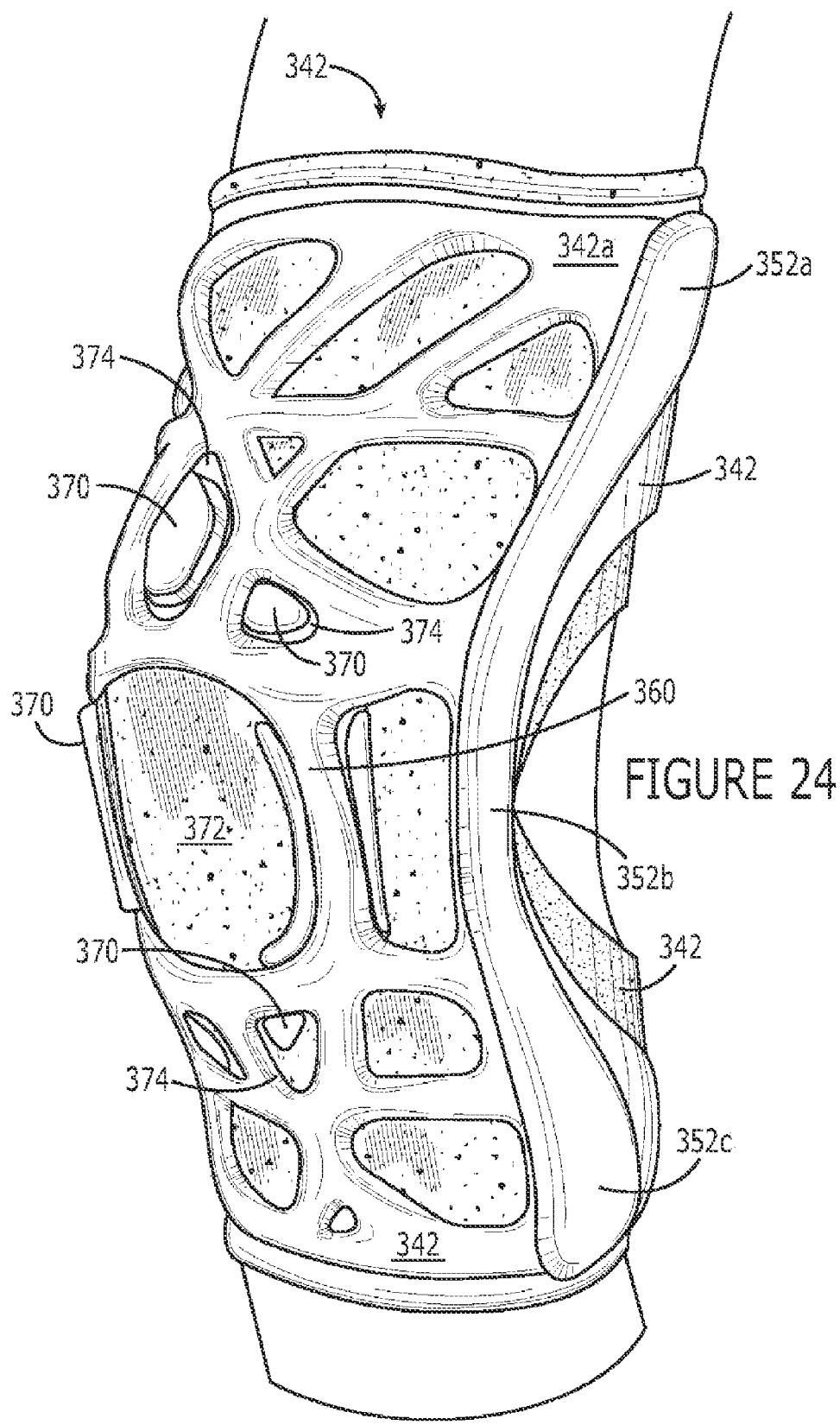
FIG. 24 is a front elevational view of the fifth support in a relaxed position.
Figure 25:
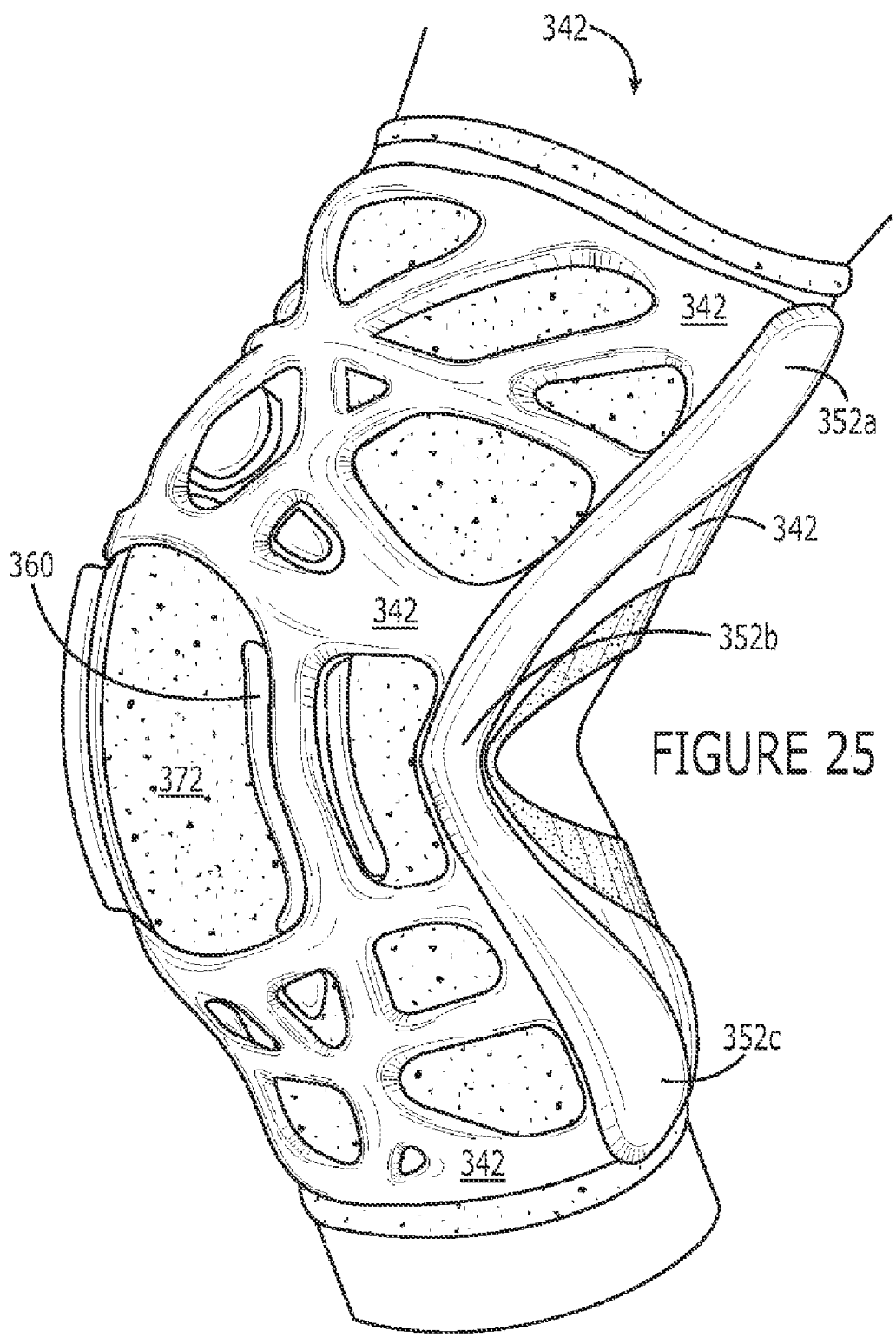
FIG. 25 is a front elevational view of the fifth support in a flexed position.
Figure 32:
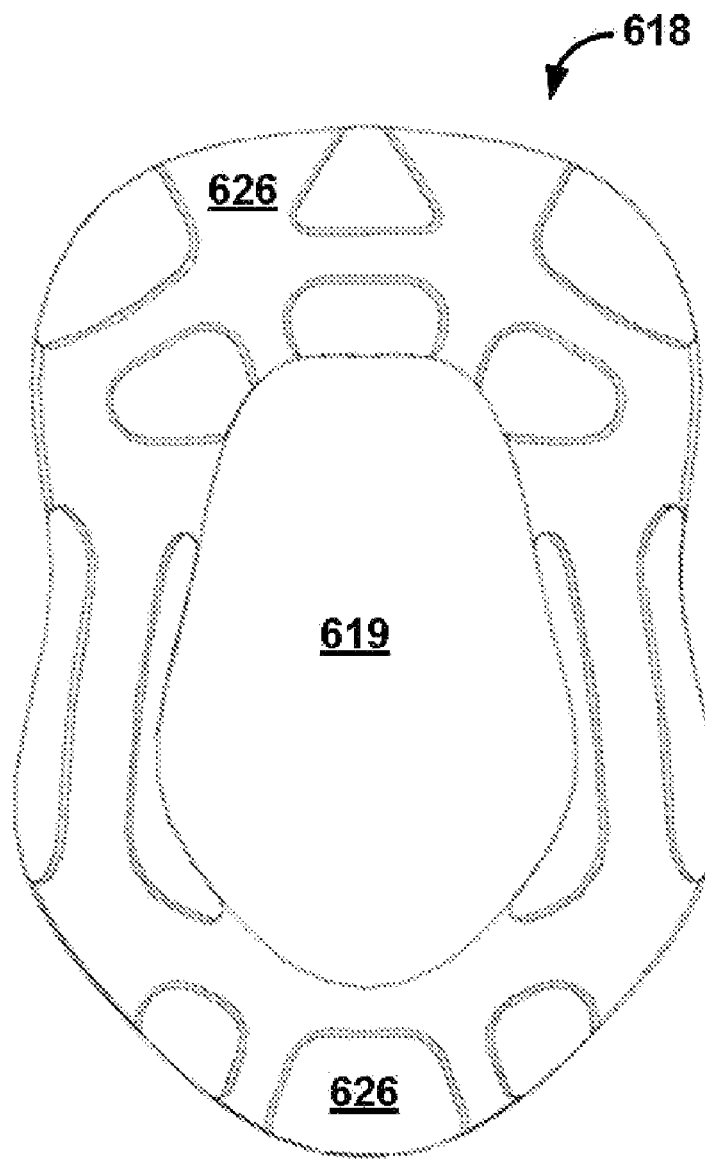
FIG. 32 is a top plan view of the anterior side of the component of FIG. 30.
Figure 33:
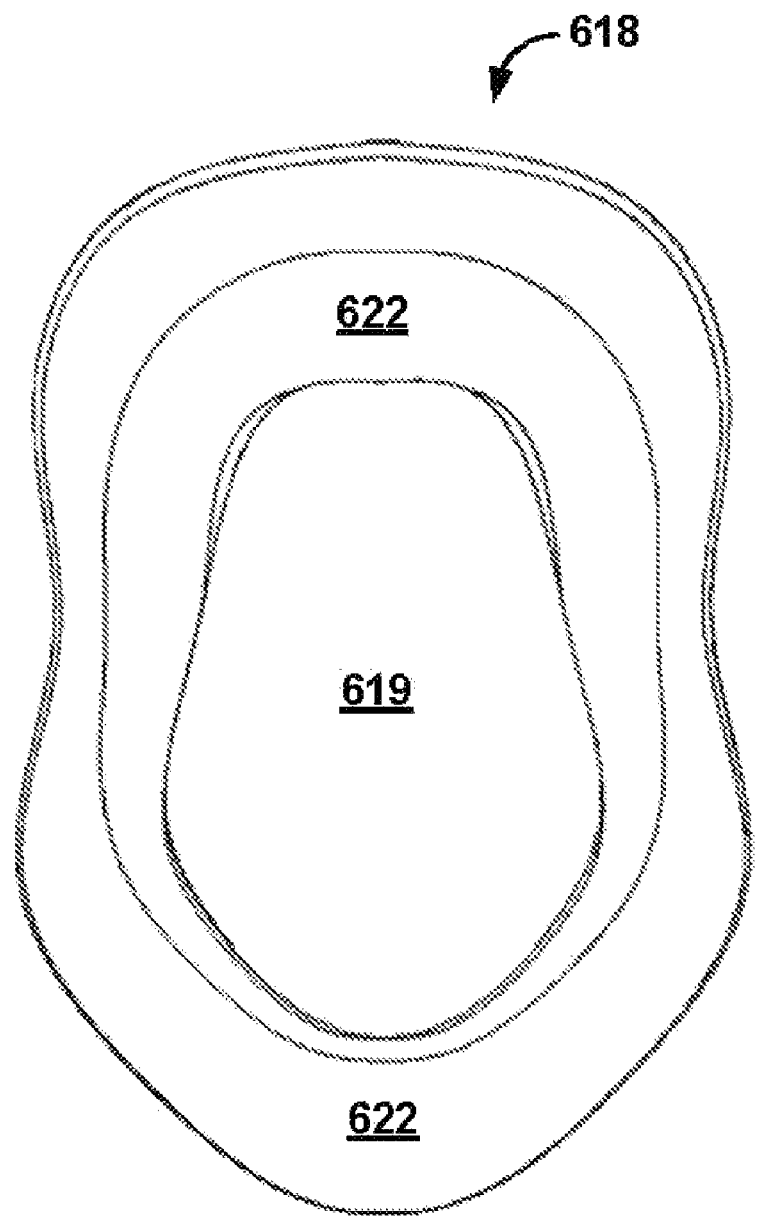
FIG. 33 is a back plan view of the anterior side of the component of FIG. 30.
Figure 34:
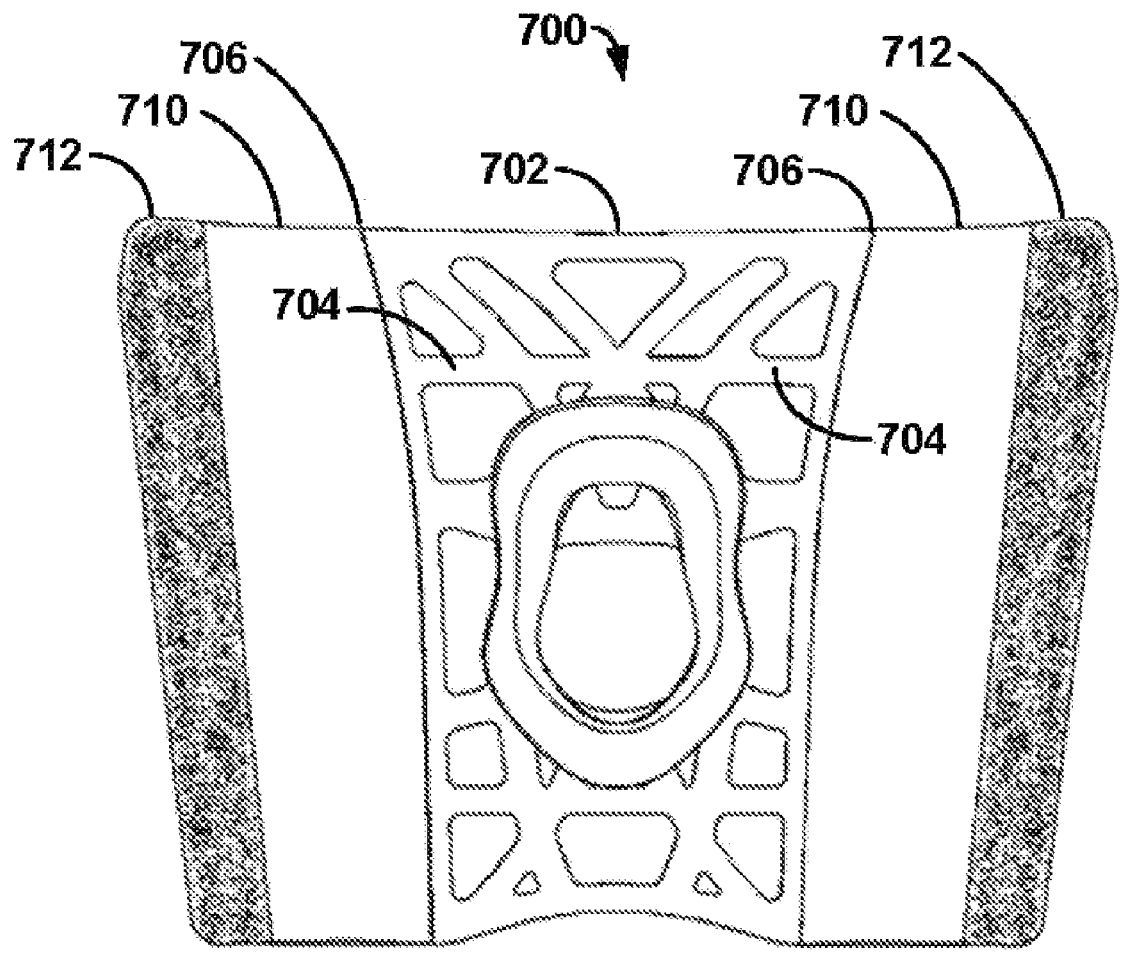
FIG. 34 is a back plan view of a seventh support in accordance with an aspect of the invention.
Figure 35:
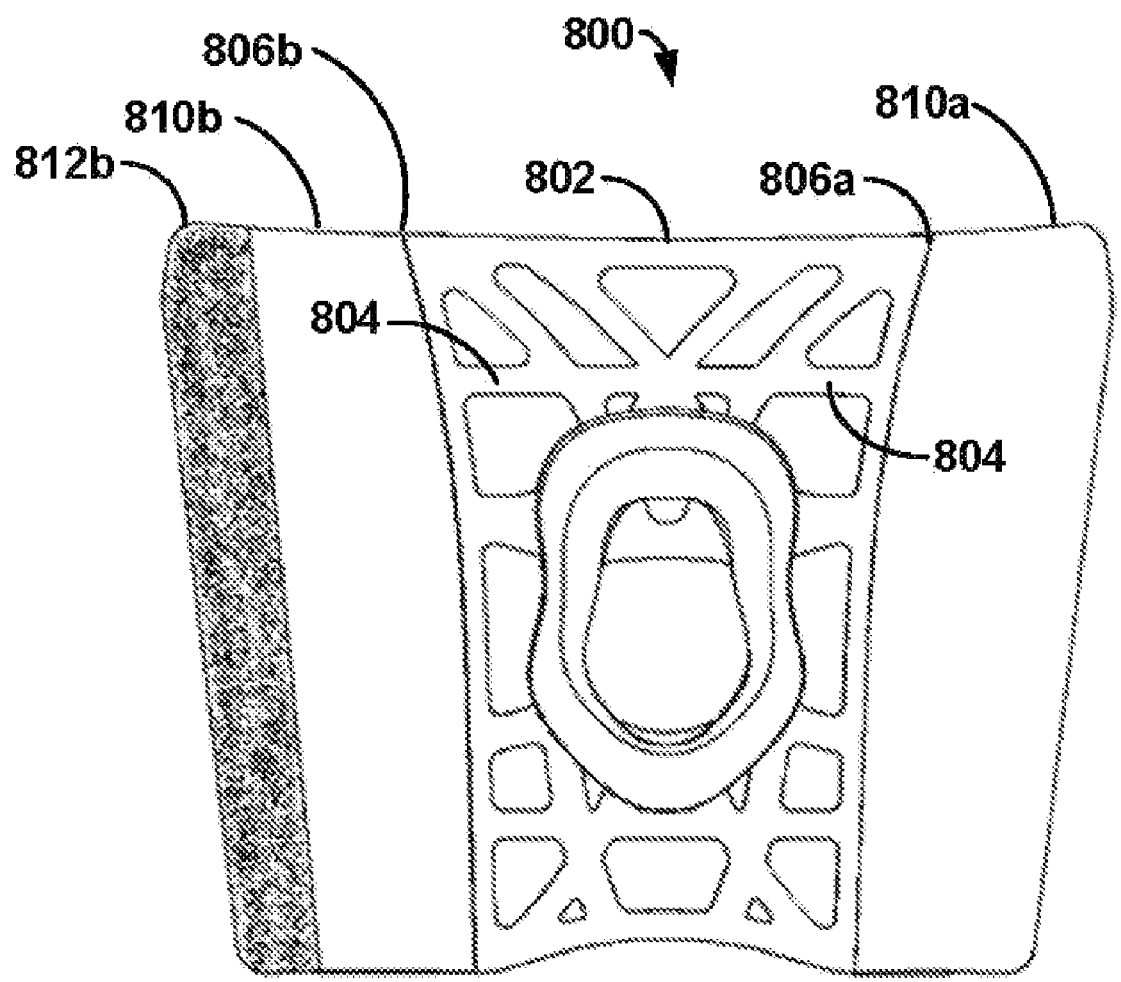
FIG. 35 is a back plan view of an eighth support in accordance with an aspect of the invention.
Figure 36:
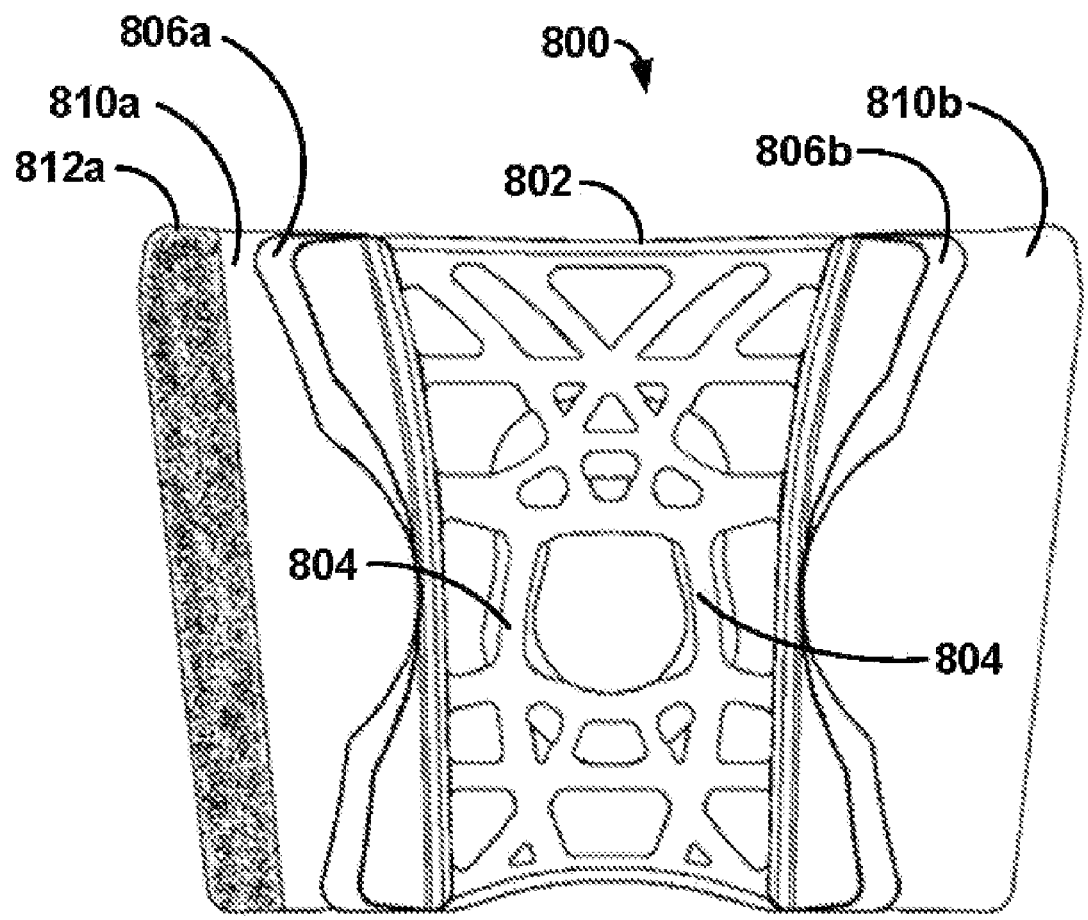
FIG. 36 is a front plan view of the eighth support.
Figure 37:
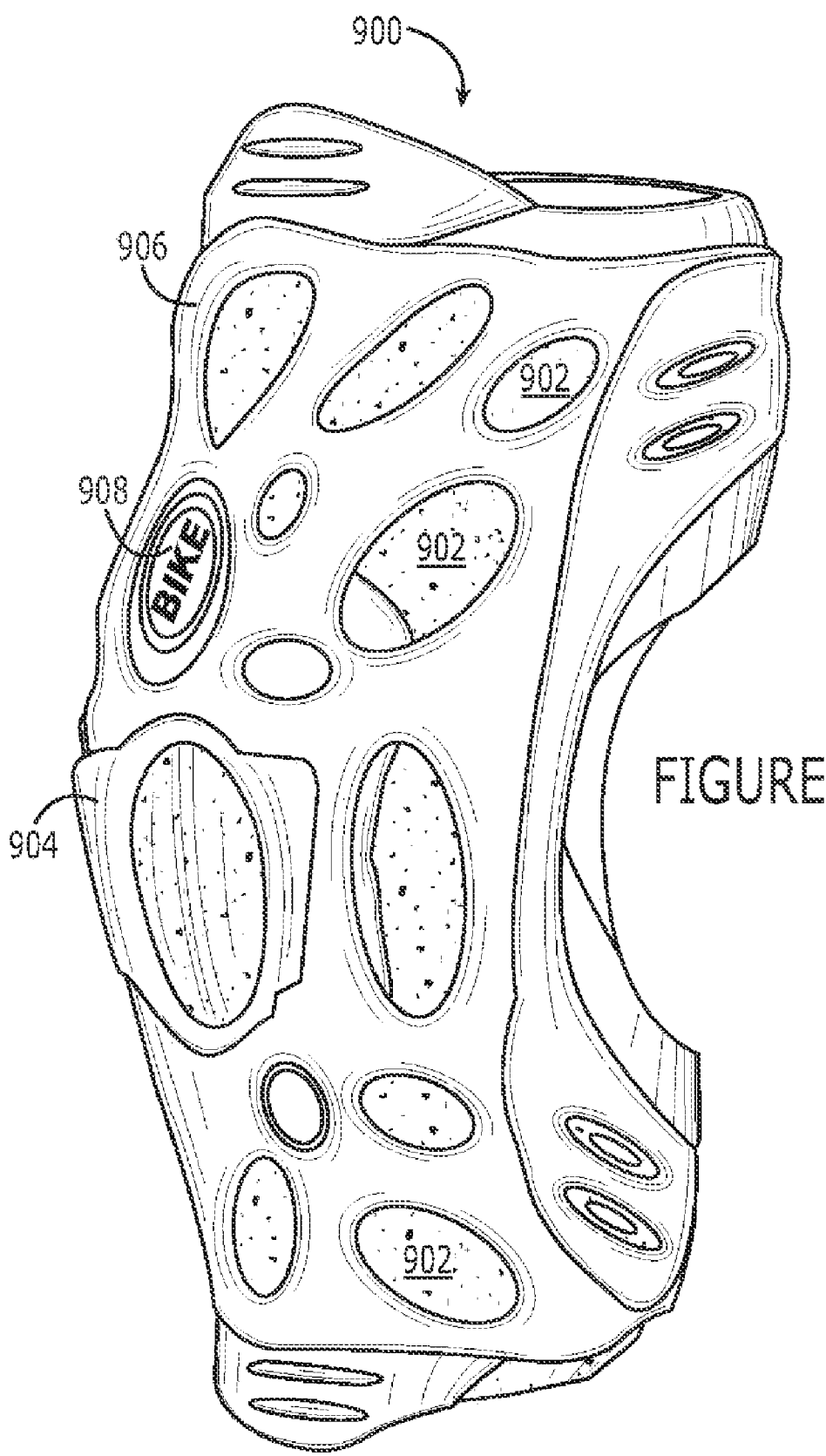
FIG. 37 is a front elevational view of a ninth support in accordance with an aspect of the invention.
Figure 38:
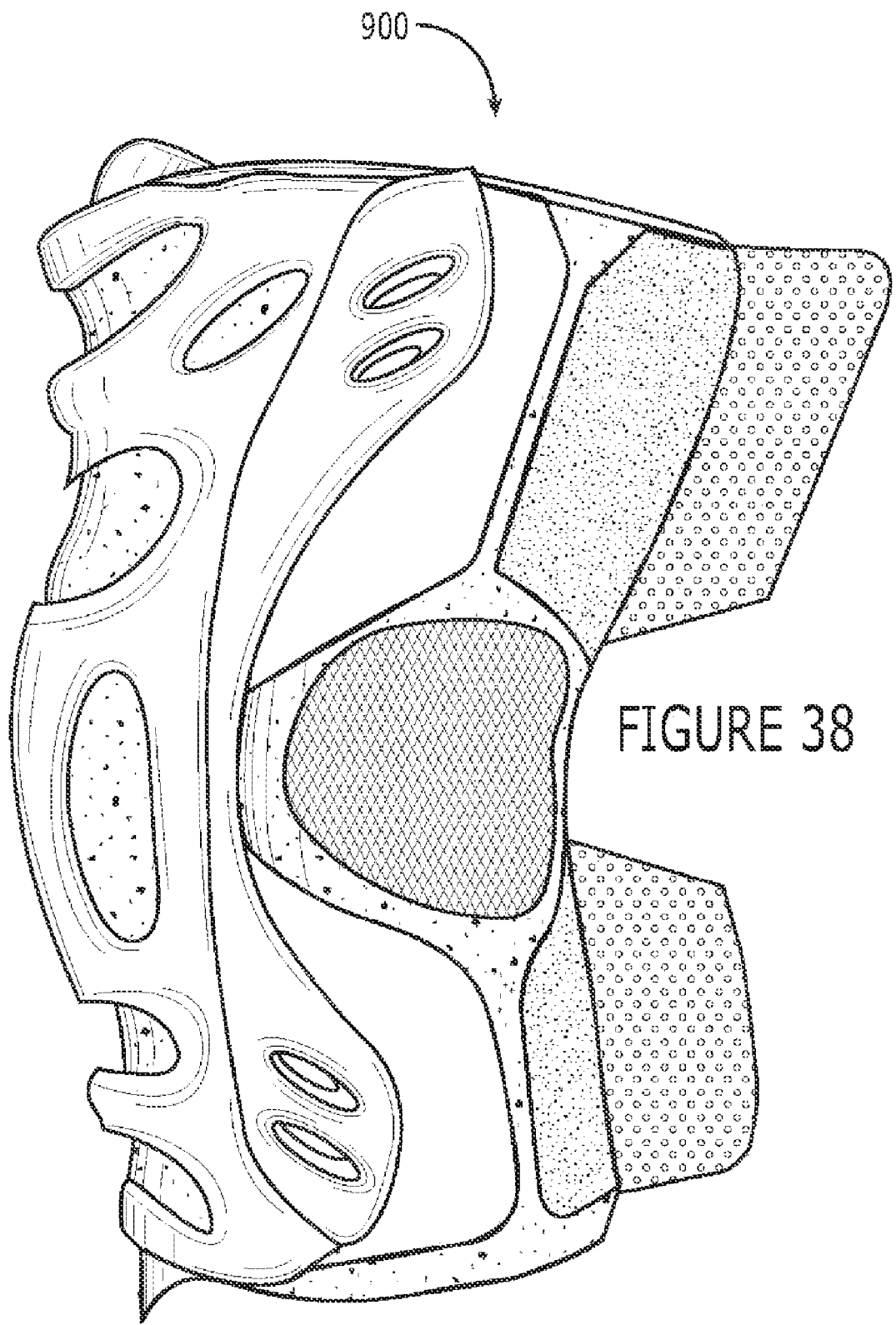
FIG. 38 is another front elevational view of the ninth support of FIG. 37.
Figure 39:
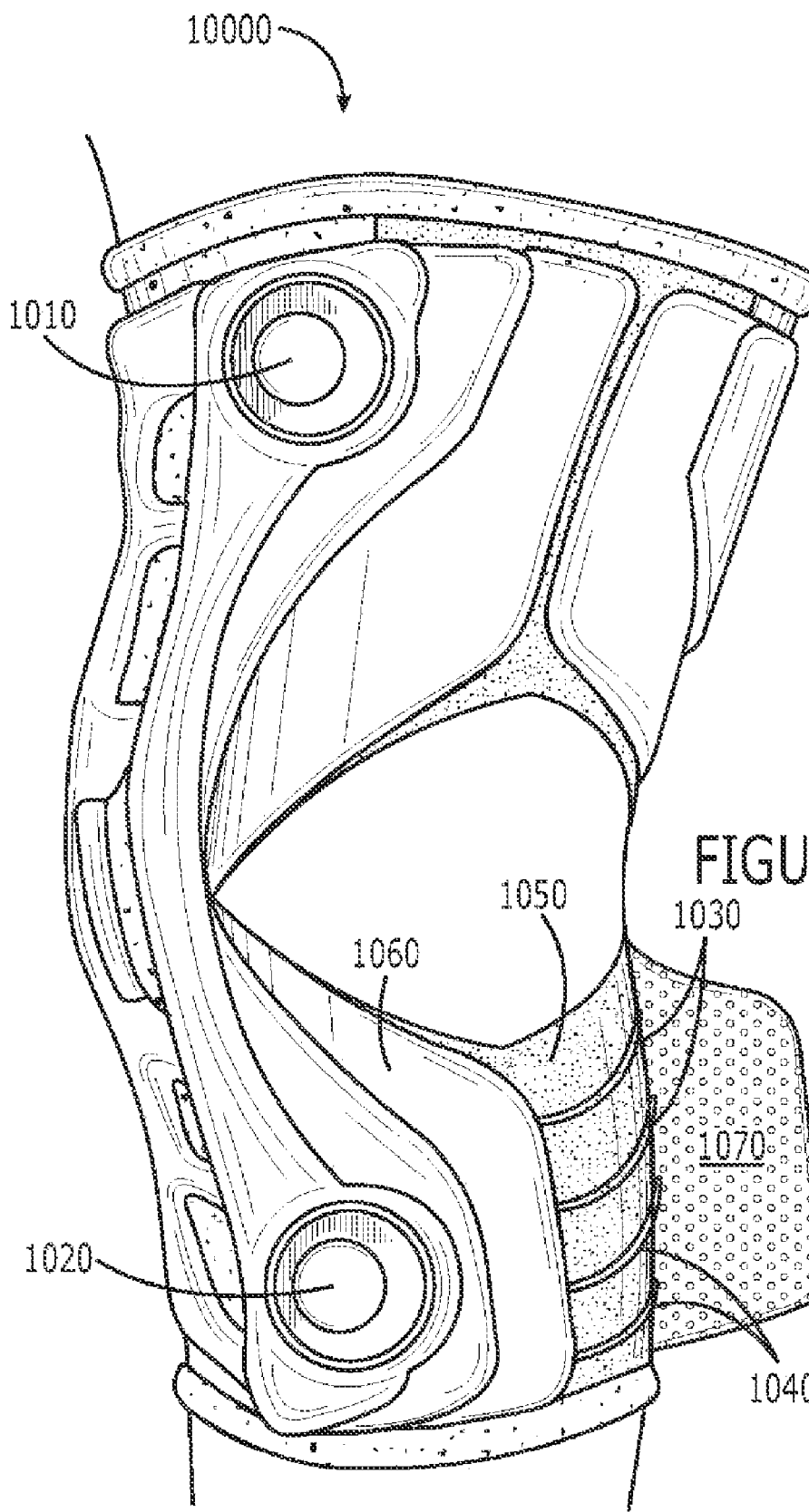
FIG. 39 is a rear elevational view of a tenth support in accordance with an aspect of the invention.
Figure 40:
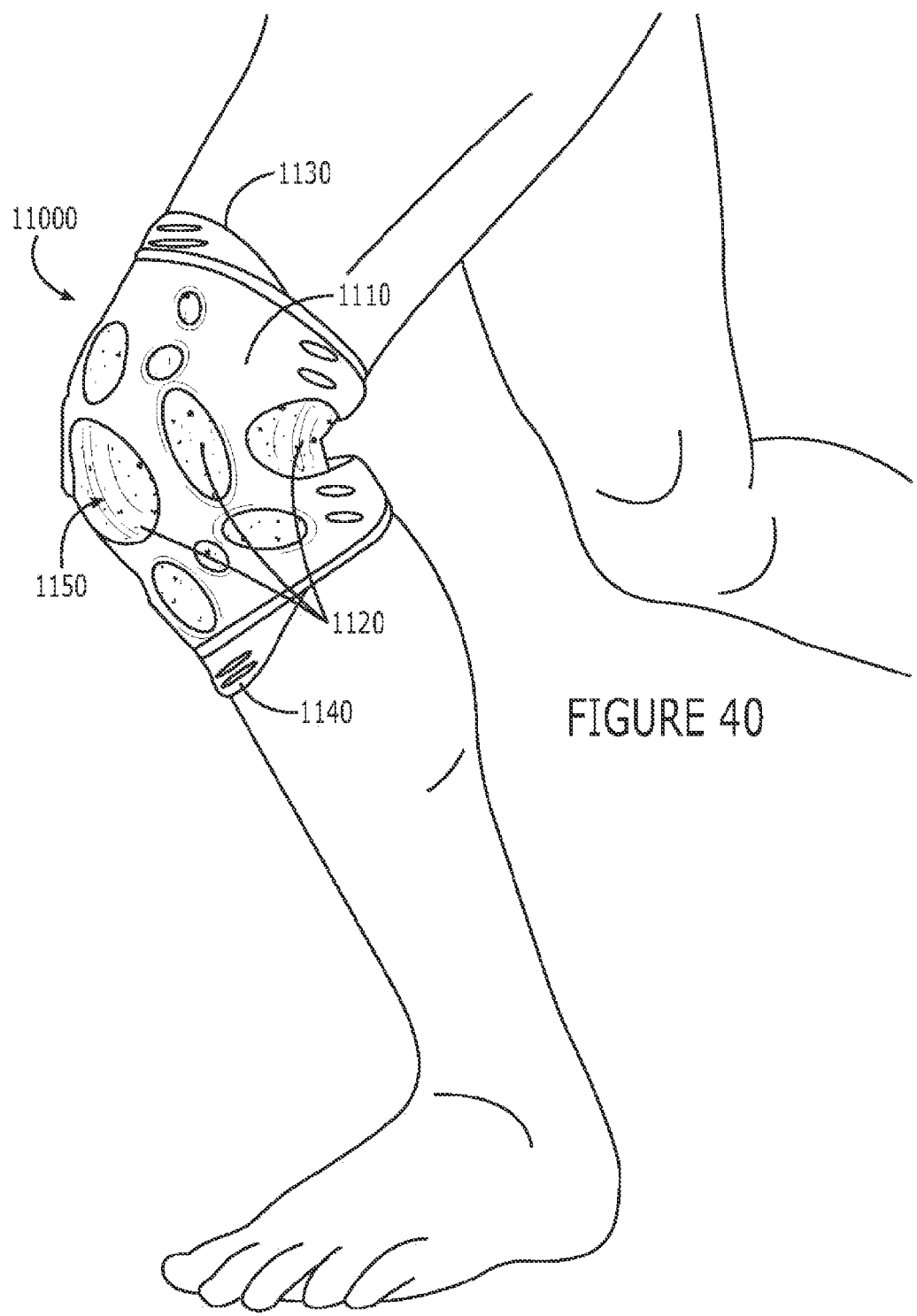
FIG. 40 is a front elevational view of an eleventh support in accordance with an aspect of the invention.
Figures 41, 42:
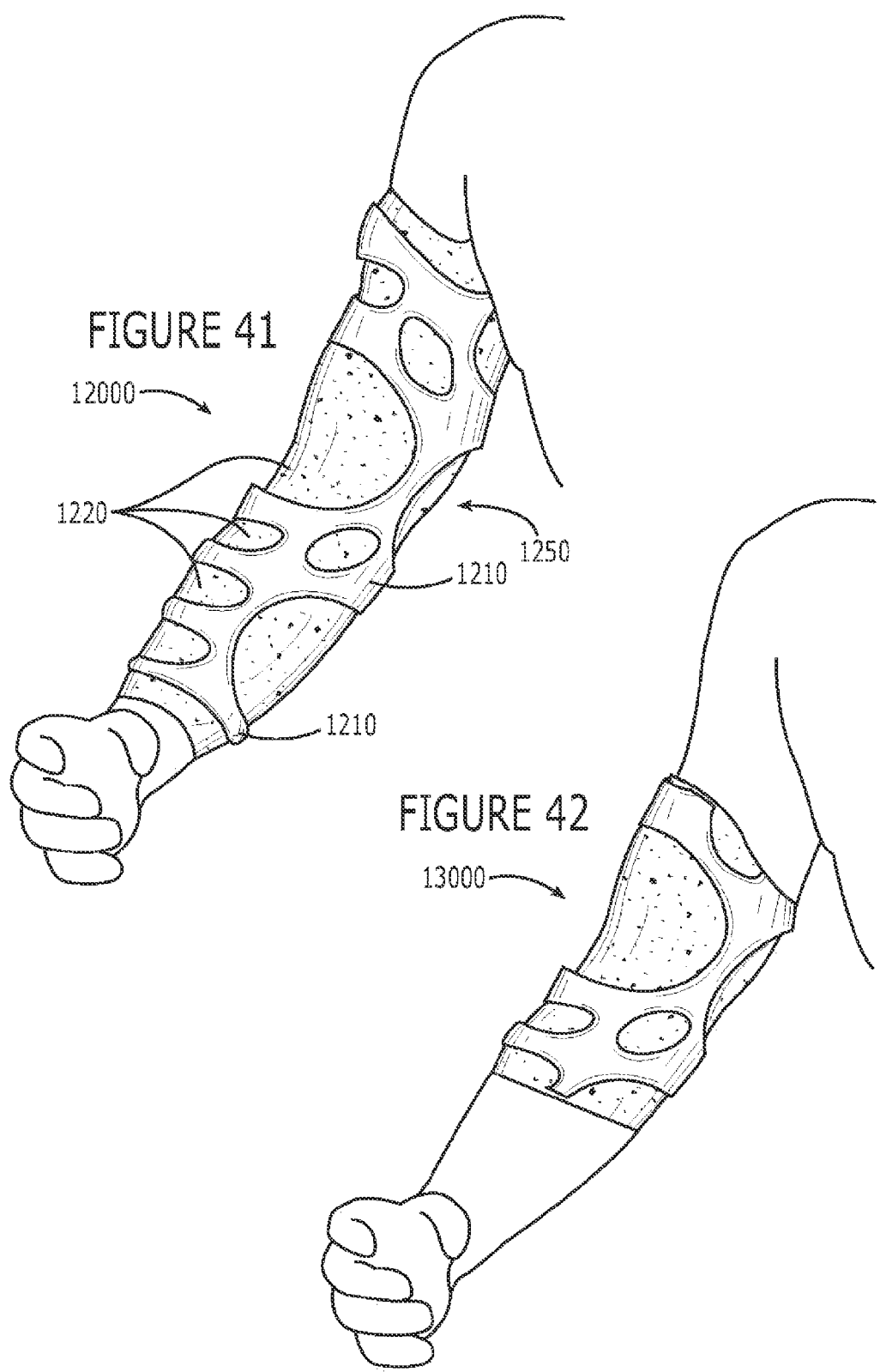
FIG. 41 is a perspective view of a twelfth support in accordance with an aspect of the invention.
FIG. 42 is a perspective view of a thirteenth support in accordance with an aspect of the invention.
Figure 43:
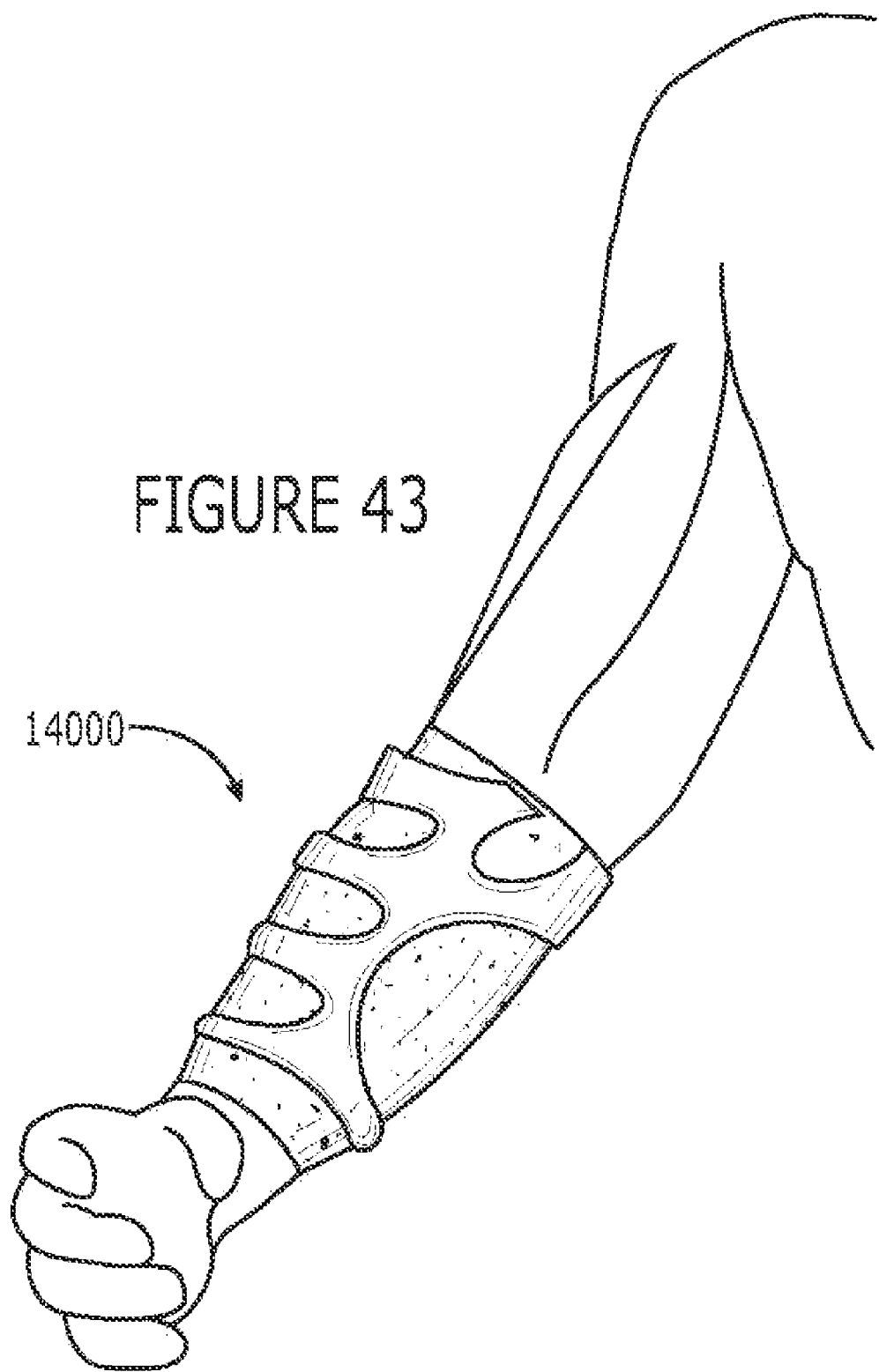
FIG. 43 is a perspective view of a fourteenth support in accordance with an aspect of the invention.
Figure 44:
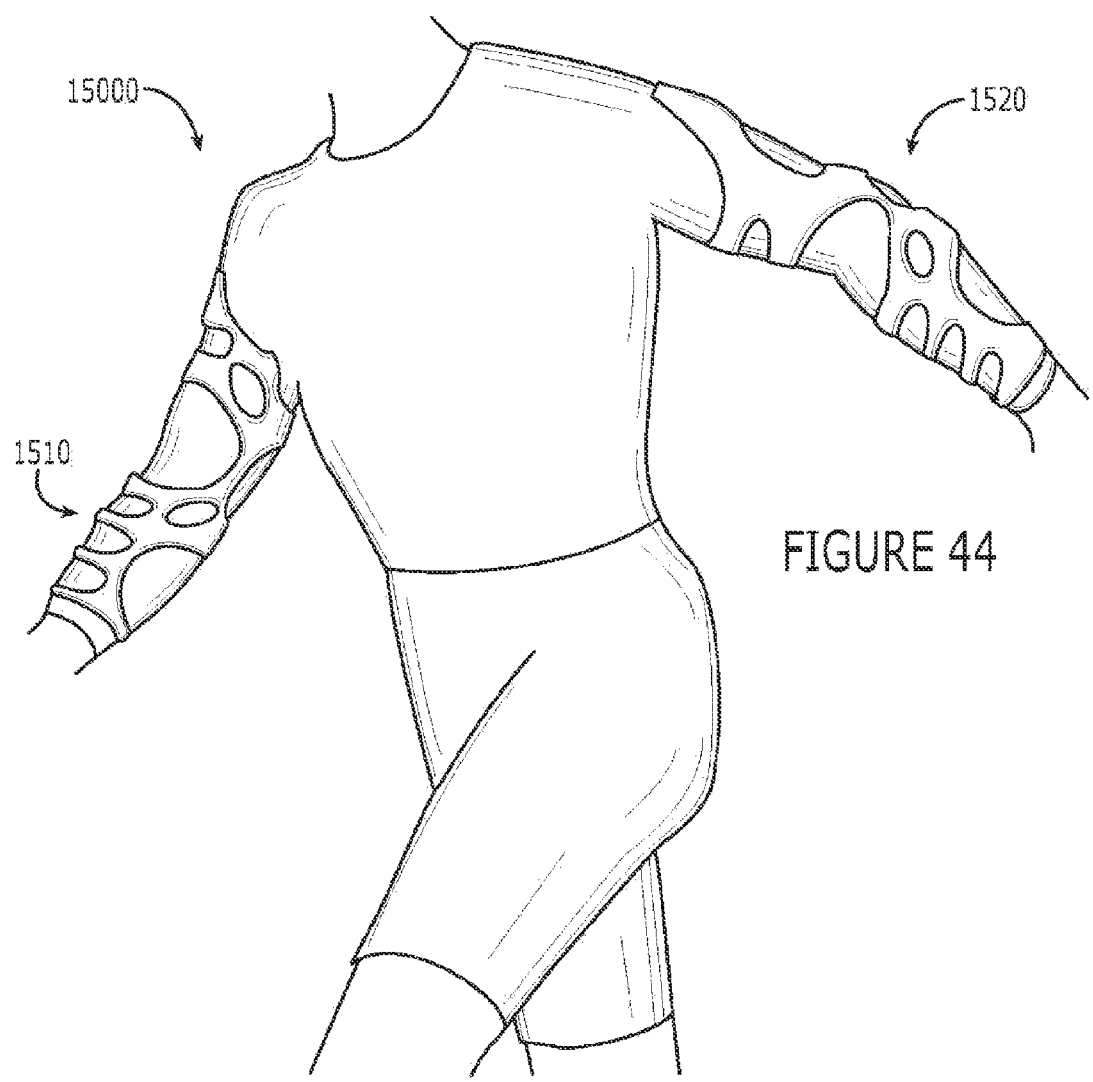
FIG. 44 is a perspective view of a fifteenth support in accordance with an aspect of the invention.
Figure 45:
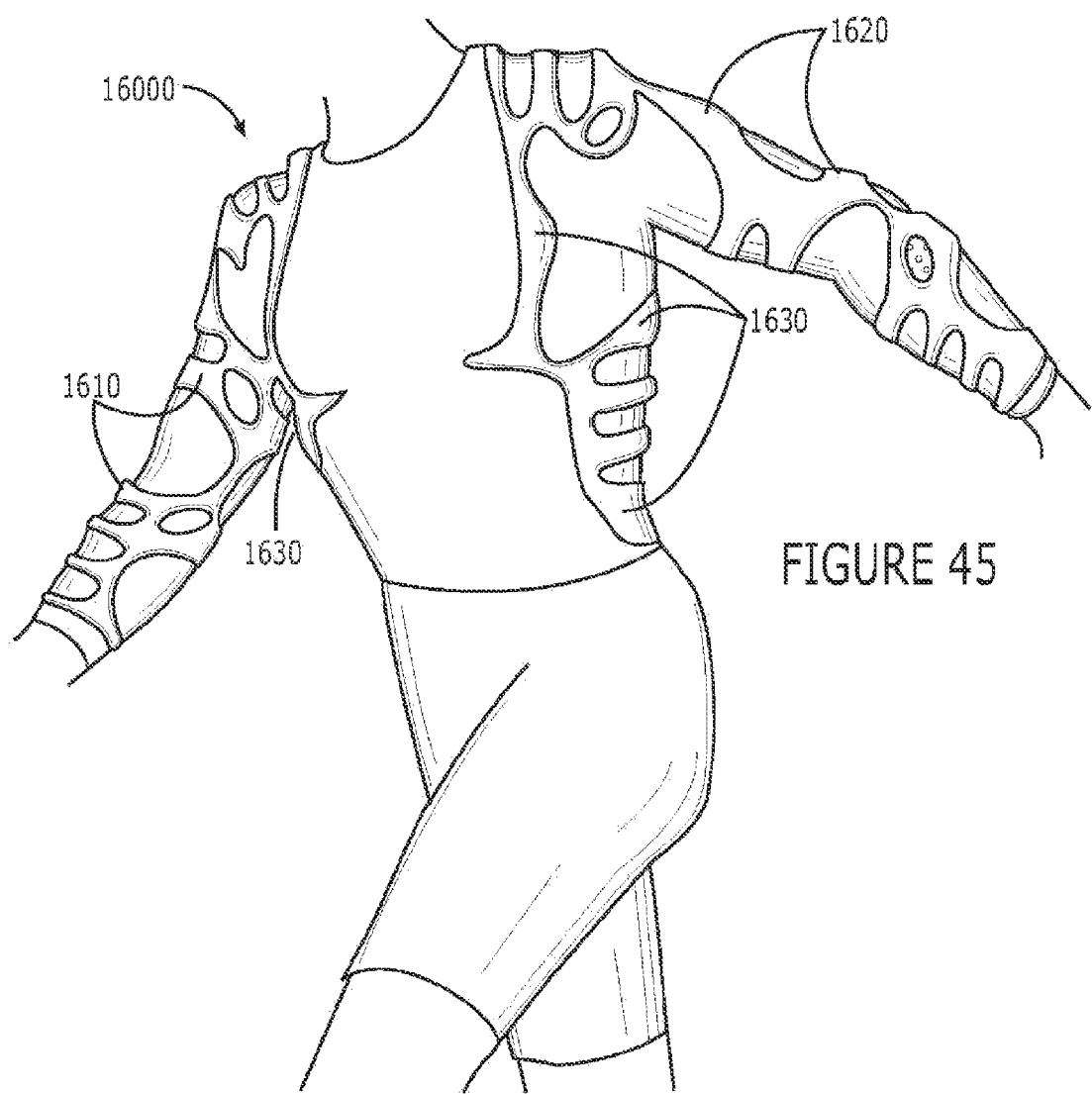
FIG. 45 is a perspective view of a sixteenth support in accordance with an aspect of the invention.
Figure 46:
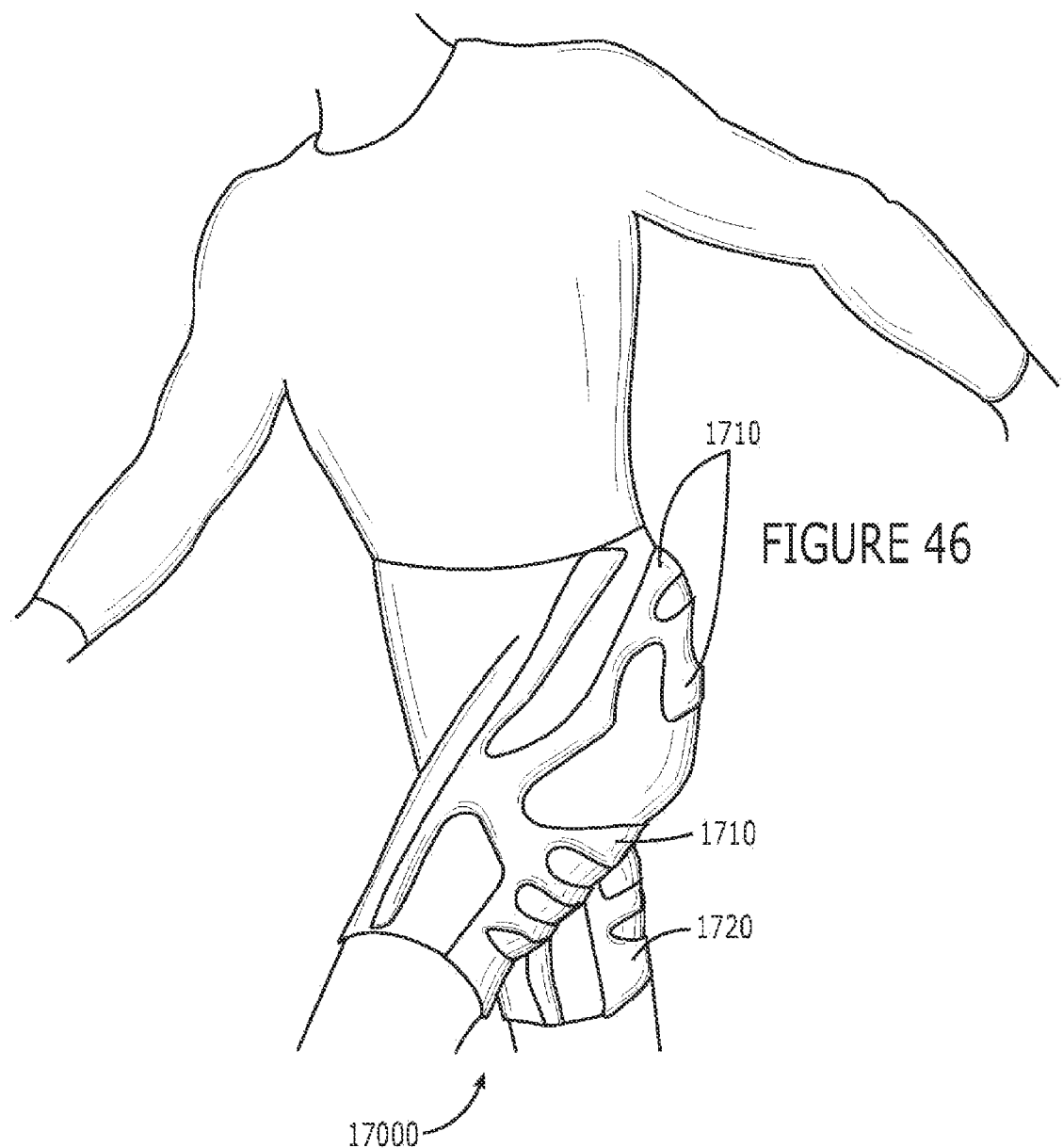
FIG. 46 is a perspective view of a seventeenth support in accordance with an aspect of the invention.
Figure 47:
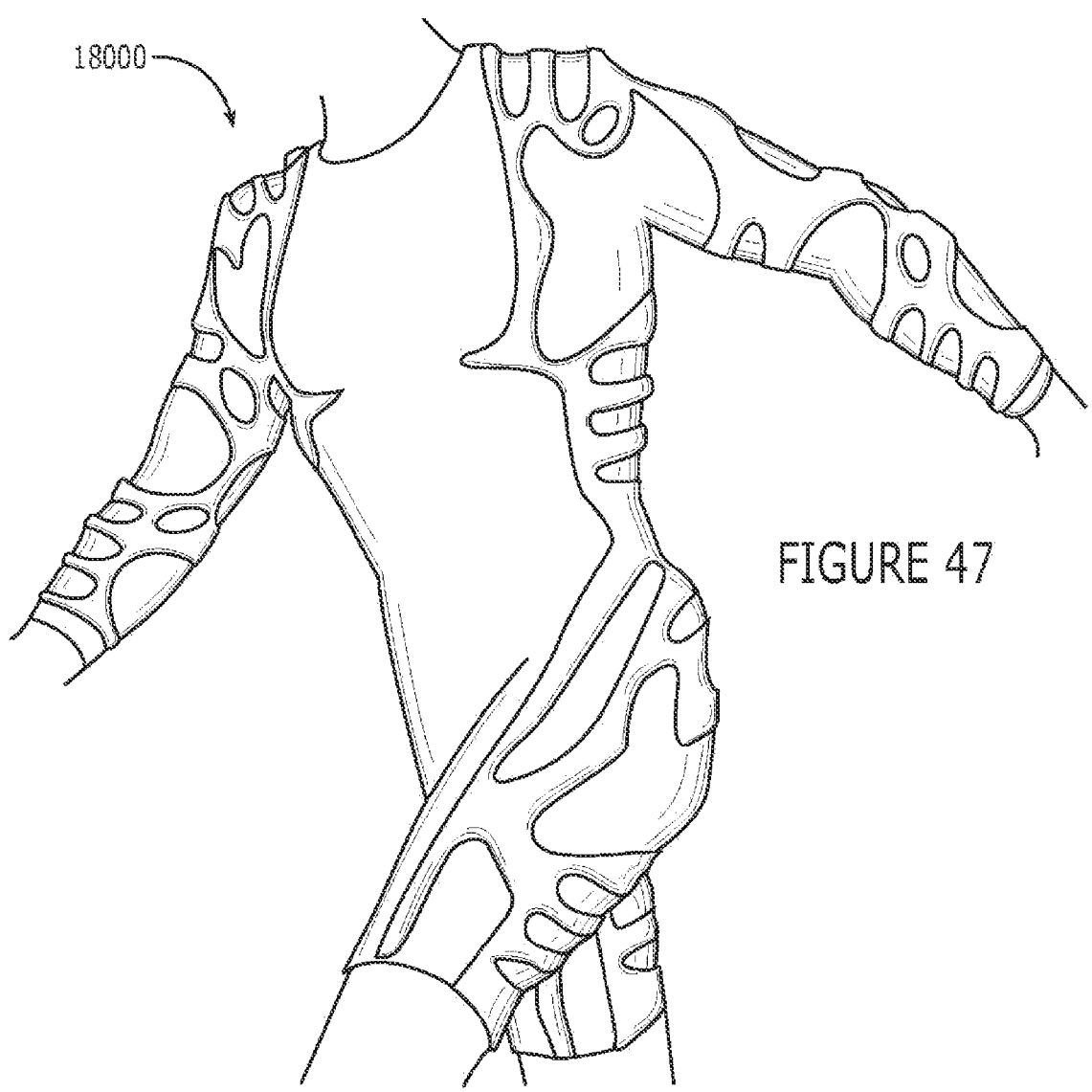
FIG. 47 is a perspective view of an eighteenth support in accordance with an aspect of the invention.
Figure 53:
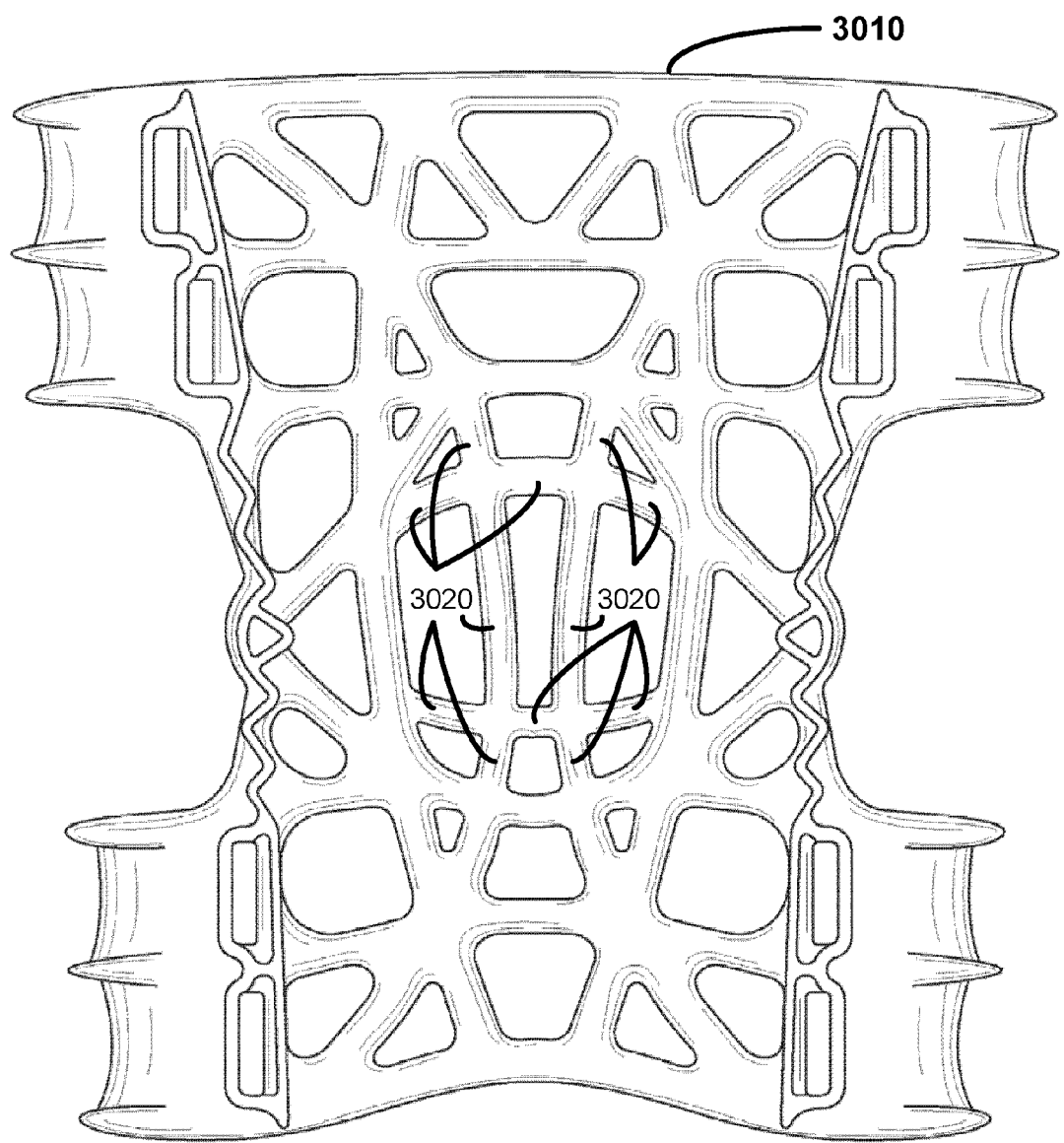
FIG. 53 is a front elevational view of a variation of the framework of FIG. 48.

In this regard, FIGS. 1-6 collectively illustrate a first embodiment of a support and components thereof in accordance with one or more aspects of the invention; FIGS. 7-9 collectively illustrate a second embodiment of a support and components thereof in accordance with one or more aspects of the invention; FIGS. 10-17 collectively illustrate a third embodiment of a support and components thereof in accordance with one or more aspects of the invention; FIGS. 18-21 and 22A collectively illustrate a fourth embodiment of a support in accordance with one or more aspects of the invention while FIG. 22B illustrates a fastening mechanism varied from that of FIG. 22A; FIGS. 23-25 collectively illustrate a fifth embodiment of a support and components thereof in accordance with one or more aspects of the invention; FIGS. 26-33 collectively illustrate a sixth embodiment of a support and components thereof in accordance with one or more aspects of the invention; FIG. 34 illustrates a seventh embodiment of a support in accordance with one or more aspects of the invention; FIGS. 35-36 collectively illustrate an eighth embodiment of a support in accordance with one or more aspects of the invention; FIGS. 37-38 collectively illustrate a ninth embodiment of a support in accordance with one or more aspects of the invention; FIG. 39 illustrates a tenth embodiment of a support in accordance with one or more aspects of the invention; FIG. 40 illustrates an eleventh embodiment of a support in accordance with one or more aspects of the invention; FIG. 41 illustrates a twelfth embodiment of a support in accordance with one or more aspects of the invention; FIG. 42 illustrates a thirteenth embodiment of a support in accordance with one or more aspects of the invention; FIG. 43 illustrates a fourteenth embodiment of a support in accordance with one or more aspects of the invention; FIG. 44 illustrates a fifteenth embodiment of a support in accordance with one or more aspects of the invention; FIG. 45 illustrates a sixteenth embodiment of a support in accordance with one or more aspects of the invention; FIG. 46 illustrates a seventeenth embodiment of a support in accordance with one or more aspects of the invention; FIG. 47 illustrates an eighteenth embodiment of a support in accordance with one or more aspects of the invention; FIGS. 48-52 and 54 collectively illustrate a nineteenth embodiment of a support and components thereof in accordance with one or more aspects of the invention; and FIG. 53 illustrates a variation of a component (the framework) of the support of FIG. 54.

The First Embodiment of a Support

With regard to the first embodiment of a support for an area of a body, a flexible and elastically stretchable framework 110 thereof is shown in FIG. 1. The framework 110 comprises generally linear segments or members 118 interconnected to define a plurality of permanent openings 120 that extend completely through the framework. Furthermore, some of these openings 120 are completely bounded by the interconnected members 118, and the interconnected members 118 defining such an opening constitute a portion of the framework 110 that is stretchable and recoverable about the entire boundary of the opening with the framework 110. Moreover, the openings 120 are permanent and exist regardless of whether the framework 110 actually is disposed in abutment with the body due to the permanent interconnection of the members 118 defining the openings 120. The framework 110 preferably is formed from an elastomeric material in a conventional molding process and, in this particular embodiment, the framework 110 resembles a web. Furthermore, the framework preferably includes no internal cavities or pockets of either fluid or gas.

An alignment opening 122 defined and bounded completely by interconnected members 118 is dimensioned and shaped specifically to receive a joint protuberance of the body. For example, insofar as the framework 110 is adapted to abut a lower thigh and upper calf of a human leg, the alignment opening 122 is shaped to receive the patella of the knee of the leg. For further example, insofar as a framework of the present invention is adapted for the surface thereof to abut an upper arm and forearm, an alignment opening thereof is shaped to receive an elbow. The alignment opening 122 is symmetrically disposed about an axis 124 and is disposed generally equidistant from opposite sides 126,128 of the framework 110, which sides extend generally parallel to axis 124.

Figure 2:
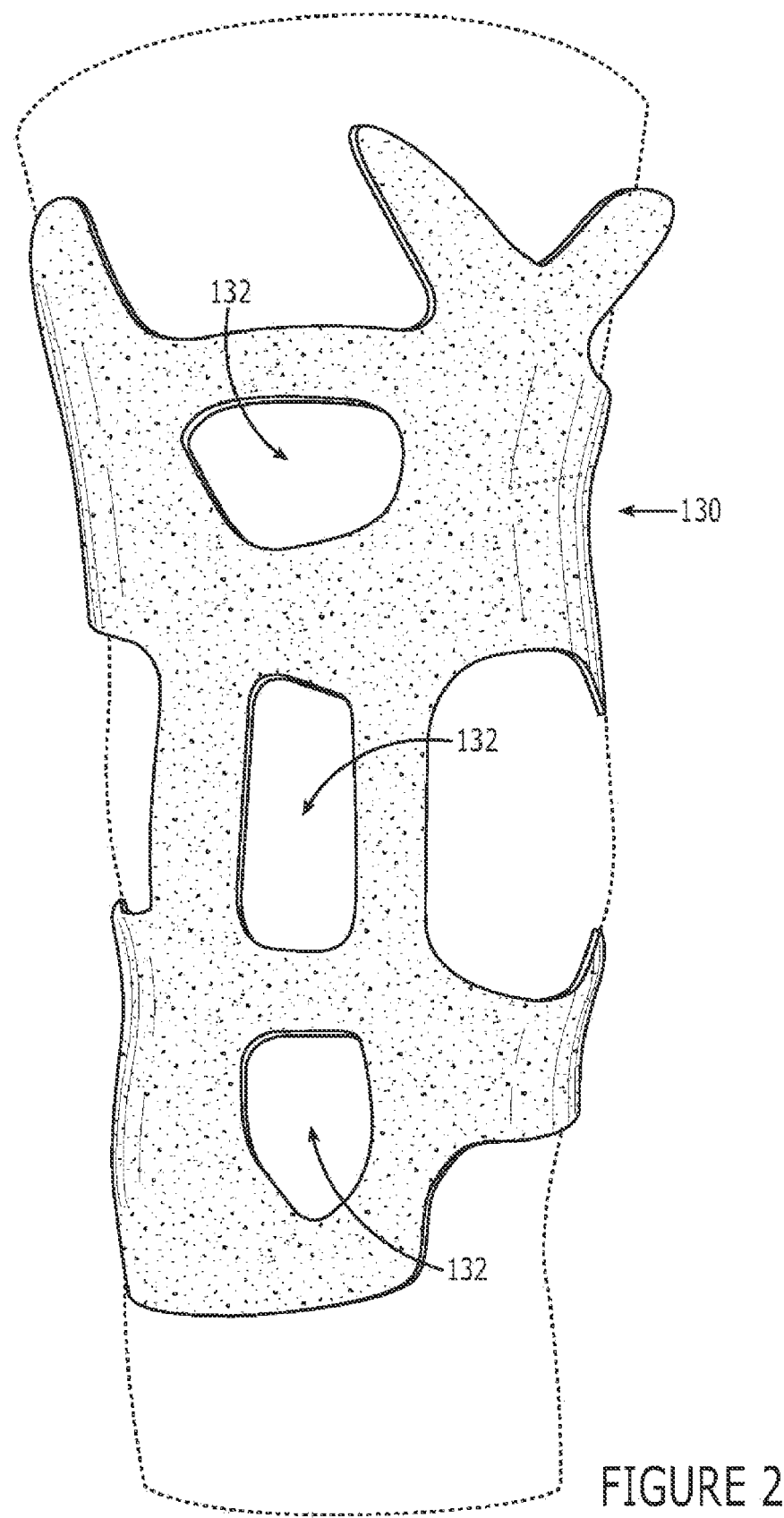
FIG. 2 is a front elevational view of a component of the first support in accordance with an aspect of the invention.
Figure 3:
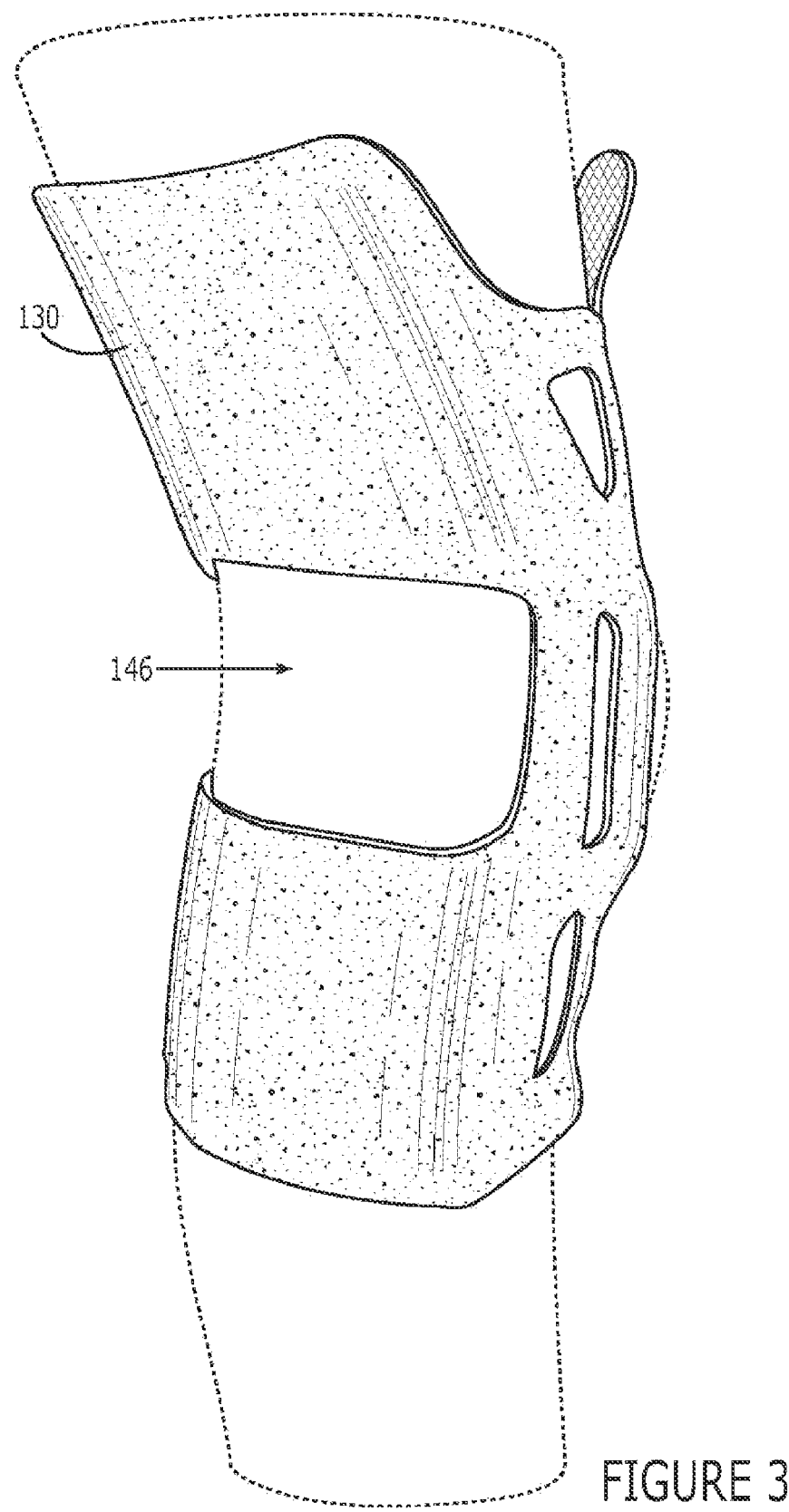
FIG. 3 is a rear elevational view of the component of FIG. 2.

Another component of the first embodiment of the support is shown in FIGS. 2-3 and comprises a sleeve 130 having a open-ended tubular structure. In this regard, it will be noted that the sleeve 130 extends around and completely encircles the leg. The sleeve 130 further defines a number of openings 132 that generally register with openings 120 of the framework 110 (FIG. 1) when the sleeve 130 is disposed between the framework and the area of the body to be supported. The sleeve 130 preferably is constructed of a flexible soft planar material. Exemplary materials include synthetic and natural fabrics, monolayer and multi-layered textiles, woven and non-woven planar materials, neoprene bonded to fabric, spandex and elastane, felt, and natural and synthetic chamois.

Figure 4:
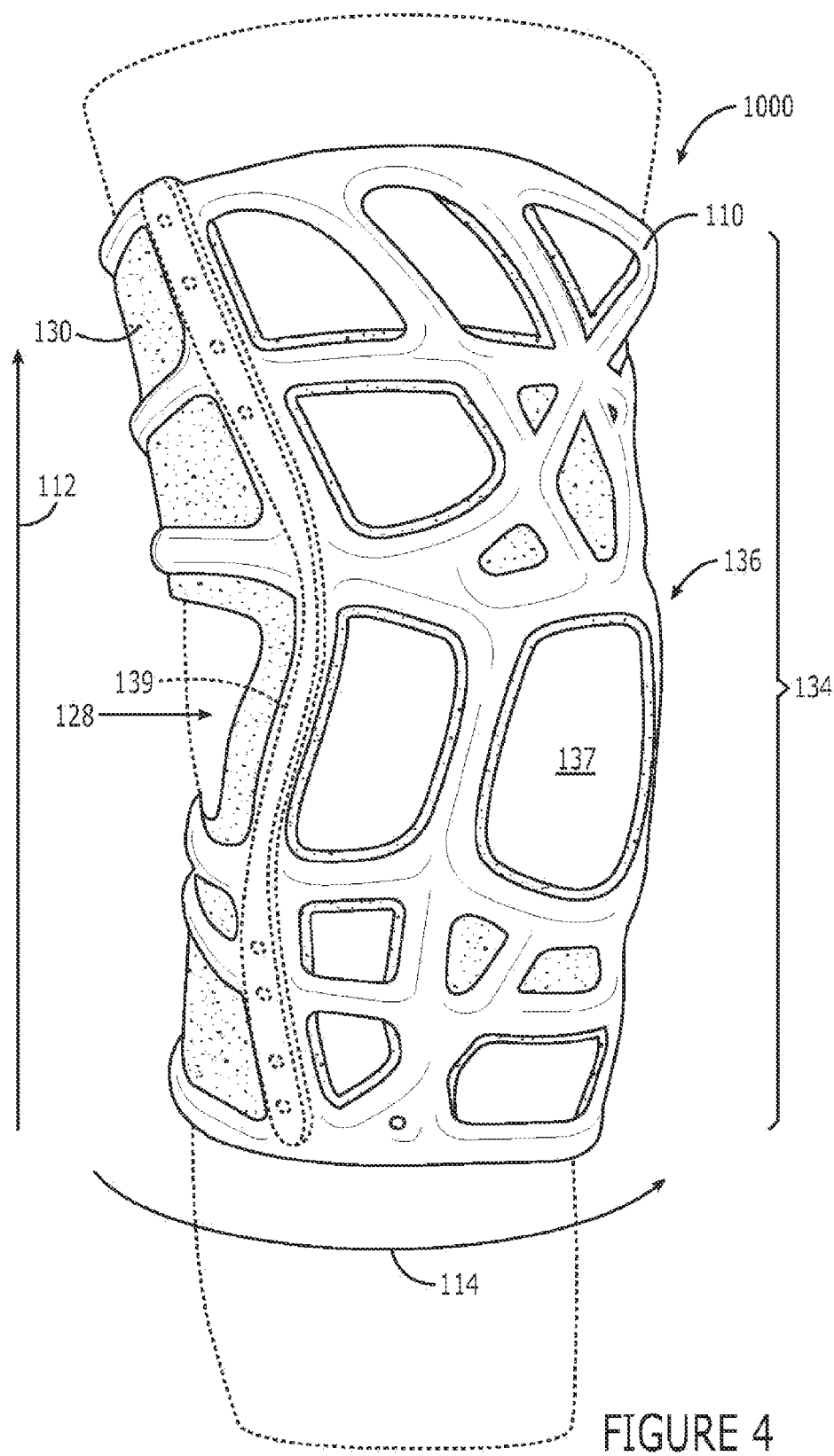
FIG. 4 is a front elevational view of the first support.
Figure 5:
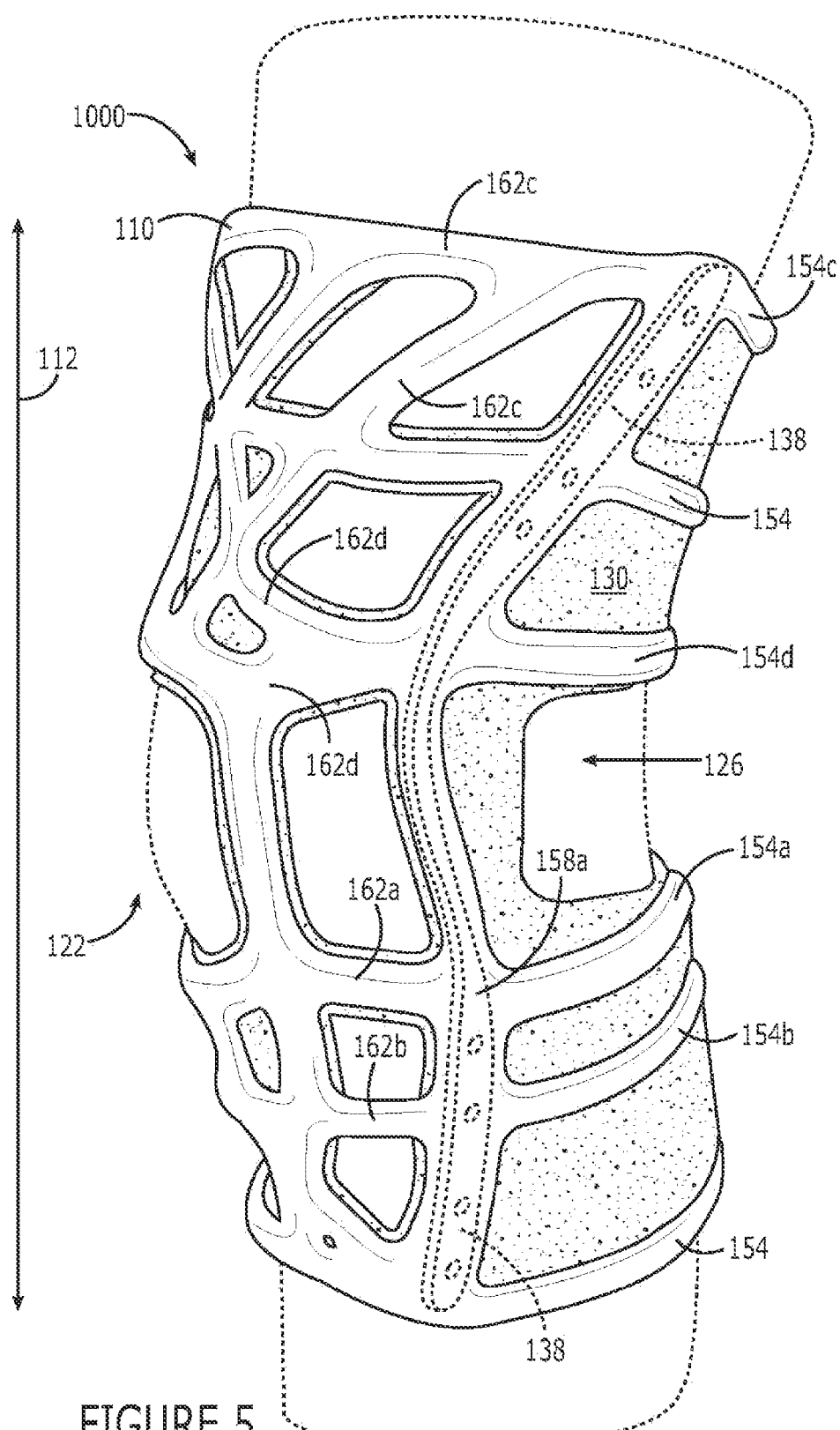
FIG. 5 is a side elevational view of the support of FIG. 4.
Figure 6:
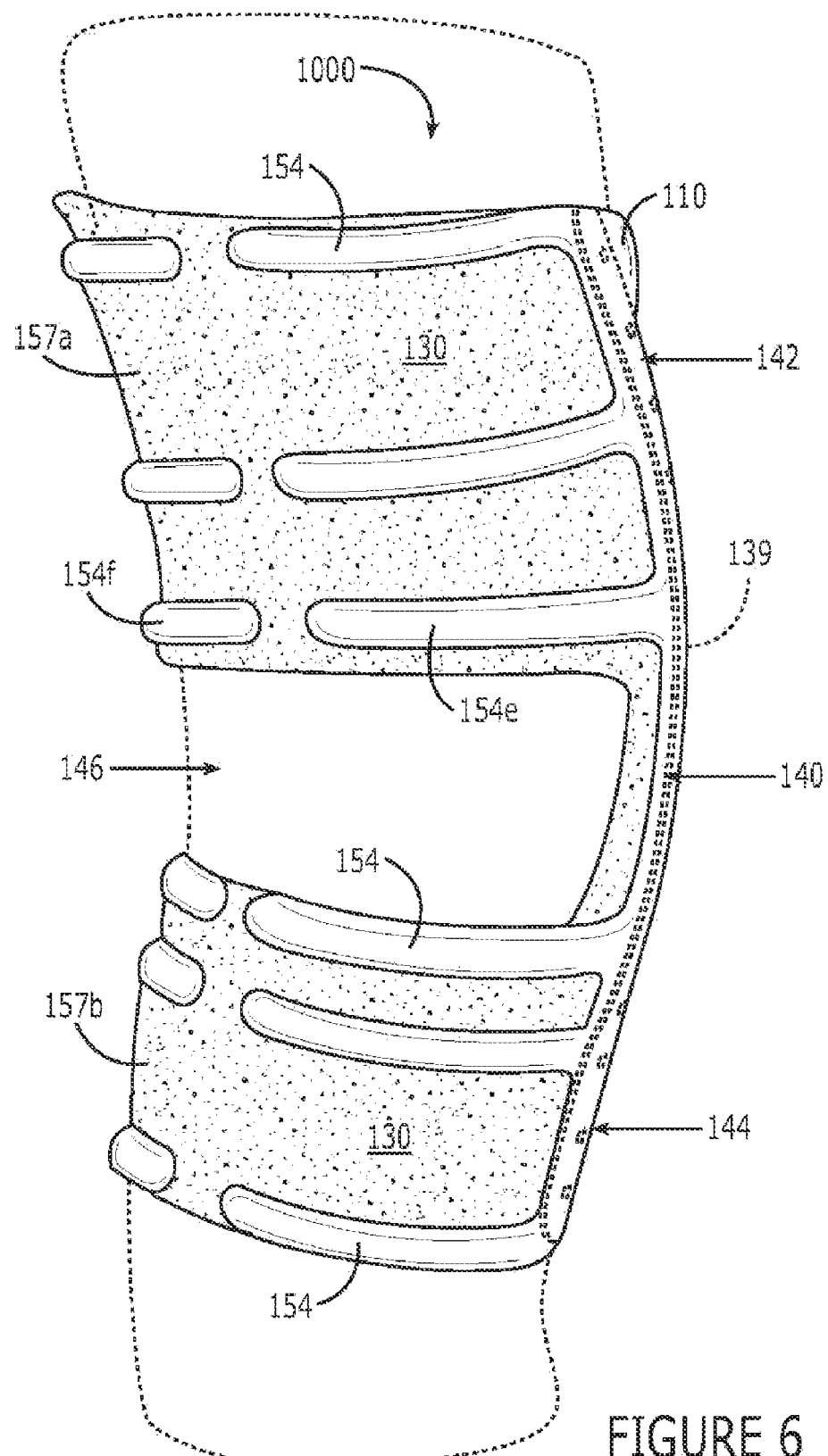
FIG. 6 is a rear elevational view of the support of FIG. 4.

The first embodiment 1000 of a support is shown assembled in FIGS. 4-6 and includes an exposed framework 110 of FIG. 1 and the sleeve 130 of FIGS. 2-3. As will be appreciated from these figures, the framework is positioned to span a knee joint of the body. Furthermore, because at least portions of the framework 110 are elastically stretchable, flexing of the knee from a straightened position results in the expansion of the framework 110 and storage of potential energy therein that is released as kinetic energy when the knee is returned to the straightened position. In this regard, the embodiment 1000 is not an immobilizing support but, instead, is a potentiating support for the area of the body including the knee joint.

In FIG. 4, a portion of the sleeve 130 is disposed between the framework 110 and a leg portion 134 proximate a knee 136 and serves as a liner for the framework 110. Also as shown in FIG. 4, the alignment opening 122 receives there through the patella 137 of the knee. As further shown in FIG. 4, the support includes a surface 116 (FIG. 1) of the framework 110 for abutment with the leg portion that generally extends in a first axial direction 112 and a second circumferential direction 114 (with reference to a cylindrical coordinate system). Moreover, the first direction 112 extends generally along the length of the leg portion and the second direction extends generally circumferentially about the leg portion with the first and second directions being generally orthogonal to one another.

As shown in FIGS. 4-5, strut members 138,139 extend generally along the first direction 112 adjacent respective, opposite sides 126,128 of the framework 110. Each strut member 138,139 is formed integrally with and embedded within the framework 110 and, preferably, is molded from an elastomeric material having a greater degree of rigidity than the elastomeric material from which the framework is molded. Furthermore, in this regard, the framework 110 preferably is molded about and encompasses the strut members 138,139. Each strut member 138,139 thereby serves to provide a degree of rigidity to two sides of the four-sided perimeter of the framework 110, i.e., provides a measure of rigidity along the perimeter sides extending in the direction of the length of the strut member. Furthermore, strut member 139 includes a cross-sectional dimension that varies along the strut member such that the strut member includes a middle portion 140 that joins opposite end portions 142,144 (FIG. 6). The cross-sectional area of the middle portion 140 is less than the respective cross-sectional areas of the end portions 142, 144, whereby the strut member 139 is more flexible in the middle portion 140 than in the end portions 142,144, during bending of the knee. Furthermore, the strut member optionally includes a density that varies along the first direction 112 such that the density of the middle portion 140 is less than the respective densities of the end portions 142,144, whereby the middle portion 140 may be more susceptible to hinging movement than the other portions of the strut member 139. Strut member 138 disposed at side 126 (FIG. 5) of the framework 110 preferably mirrors the construction of the strut member 139, and the strut members are symmetrically disposed about an axis of symmetry of the framework 110. Furthermore, patterns (not shown) may be imprinted in the strut members that further alter the elastic properties. Similarly, patterns may be imprinted or formed in portions of the framework to alter the elastic stretchability of the framework.

As will be evident from FIGS. 4-6, each strut member 139,140 is located along the axial extent at opposite sides 126,128 of the framework 110 so as to span the hinge joint of the knee, with the middle portion of each strut member being disposed proximate the hinge axis of the knee. Each strut member and, in particular, its middle portion, preferably is expandable and recoverable between a first initial state and extended states wherein, when expanded to an extended state during flexing of the knee joint, the strut member stores potential energy that is released as kinetic energy upon return of the strut member to the initial state. Thus, the embodiment 1000 further comprises a potentiating support for the area of the body, including the knee joint, for this reason as well.

In further regard to flexing of the knee and the hinging movement of the strut members, an opening 146 is defined by the sleeve 130 to accommodate flexing of the knee about the middle portions of the strut members (as shown by middle portion 140 of strut member 139 in FIG. 6). This opening 146 minimizes bunching or gathering of the sleeve 130 in the bend or fold of a flexed joint in order to promote comfort of the wearer of the support. Additional openings 132 in the sleeve 130 (FIG. 2) further may be provided in this respect and, as shown in FIGS. 4-5, such openings also may generally register with openings of the framework 110, thereby promoting ventilation of the area of the body covered by the support and providing an increased level of comfort to the wearer of the support.

With regard to donning the support, the support is merely wrapped about the area of the body to be supported and either fully or partially encircles the body. Furthermore, as will be appreciated from the drawings, the framework 110 of the support does not overlap itself. A fastening mechanism, now described in detail, is then affixed to the sleeve 130, which presumably has already been donned, for securing the support in abutment with the area of the body to be supported.

The support is removably attachable to the sleeve 130 by way of a fastening mechanism comprising strip-fasteners 150 and spot-fasteners 152 (FIG. 1). Furthermore, each strip fastener 150 and spot-fastener 152 itself is attached to the surface 116 of the framework 110, preferably by being adhered to the surface 116. For example, insofar as the outer surface of the sleeve 130 (FIGS. 2-3) provides loops for engaging hooks, the fasteners 150,152 (FIG. 1) comprise hooks for engaging the loops of the sleeve in hook-and-loop couplings. Such hook-and-loop couplings fastening mechanisms are commonly sold and known by the trademark VELCRO. Furthermore, in this regard, preferably most of the entire outer surface of the sleeve is provided with loops such that disposition of the framework in abutment with the sleeve 130 as shown in FIGS. 4-5 readily effects hook-and-loop coupling of the strip-fasteners 150 and spot-fasteners 152 (FIG. 1) of the framework 110 with the outer surface of the sleeve 130. Moreover, the orientation of such attachment preferably maintains general overlapping of the openings of the sleeve with those of the framework and prevents collapsing, creeping, or bunching of the sleeve as the support is worn throughout flexing of the knee joint.

In addition to the foregoing strip-fasteners 150 and spot-fasteners 152, the fastening mechanism of the support further comprises additional fastening components, namely, fastening straps 154 having fasteners 156 (FIG. 1). Furthermore, as shown in FIG. 1, the fastening straps 154 are attached to the framework 110 at points of attachment 158 along opposite sides 126,128 of the framework 110. The fasteners 156 are adapted to removably fasten to the sleeve 130 and, specifically, to the portions of the sleeve 130 that are attached to and that extend between the opposite sides 126,128 of the framework 110, such portions of the sleeve 130 defining bands 157a,157b (FIG. 6). For example, insofar as the outer surface of the sleeve provides loops for engaging hooks, the fasteners 156 comprise hooks for engaging the loops in hook-and-loop couplings. In FIG. 1, the fastening straps 154 are formed integrally with the framework 110 and are unitary therewith though, in other embodiments, the fastening mechanism is removably attached to the framework 110 such as, for example, through D-rings. The D-rings may be formed integrally with the framework or with strut members attached to the framework.

Utilizing the fastening mechanism of the support, the framework 110 can be tensioned in its abutment with the body and, moreover, the tension with which the surface of the framework is disposed in abutment with the area of the body to be supported can be adjusted as desired. When donned, the support serves as an exoskeleton of the body, at least in the supported area of the body. In this regard, with the support donned as shown in FIG. 5, the fastening straps 154 are grasped and manually pulled at the desired level of tension. During this tensioning, the fasteners 156 then are fastened to the bands 157 (FIG. 6) to secure the tensioned straps 154. For example, as shown in FIG. 6, opposed, tensioned fastening straps 154e,154f are removably fastened to the band 157a. Tensional forces are applied by all of the fastening straps 154 at multiple points of attachment along the opposite sides of the framework 110, whereby these tensioned straps are elastically stretched, the framework 110 consequently is elastically stretched, and the surface thereof is shaped to fit the abutted area of the body.

Additionally, it will further be appreciated by the Ordinary Artisan that, as shown for example in FIG. 5, a particular fastening strap 154a may apply tension to a point of attachment 158a along side 126 of the framework 110 and that, while the integral construction of the framework 110 generally conveys tensional forces from any one portion of the framework to the other portions, tension of a particular member 162a is correlated with that of the fastening strap 154a due to their shared proximity to the point of attachment 158a and their substantially mutually collinear arrangement. Thus, insofar as the amount of tension applied to fastening strap 154a is different from the amount of tension applied to fastening strap 154b, the amount of tension in member 162a is likewise different than the amount of tension in member 162b. Furthermore, insofar as the amount of tension applied to fastening strap 154c is different from the amount of tension in 154d, the tensions in members 162c are likewise different from the tensions in members 162d. Thus, the framework is capable of being adjustably stretched and its shape thereby conformed to the abutted area of the body to provide the desired level of support.

The Second Embodiment of a Support

With regard to the second embodiment 2000 of a support for an area of a body, the second embodiment 2000 includes a framework that is the same as the framework 110 of the first embodiment 1000. The second embodiment 2000 further is considered to include, as part thereof, sleeve 168 (FIGS. 7-8) that is generally the same as sleeve 130 of FIGS. 2-3, except that the sleeve 168 is continuous and does not define openings therein that would register with corresponding openings of the framework 110. As shown in FIG. 7, sleeve 168 includes fasteners covering most of the entire outer surface of the sleeve. Alternatively, as shown in FIG. 8, the sleeve 168 includes certain discrete areas 172 that comprise loop fasteners for receiving the hook fasteners 156 of fastening straps 154 (FIG. 1) and, thus, does not include loop fasteners covering most of the entire outer surface of the sleeve as shown in FIG. 7. FIG. 9 illustrates the second embodiment 2000 including the framework 110 of FIG. 1 and the sleeve 168 of FIG. 8.

The Third Embodiment of a Support

The third embodiment 3000 of a support is shown in FIGS. 10-17 and is the same as the first embodiment 1000 except for the following noted differences.

First, the embodiment 3000 includes a liner 198 (FIG. 16) that is attached directly to the framework 182 such as, for example, by plasticized welding, elastomeric welding, adhesive attachment, or by sewing. The support further includes two bands 199a, 199b (FIG. 16) extending between and directly attached to the two opposite sides of the framework 182.

Figure 10:
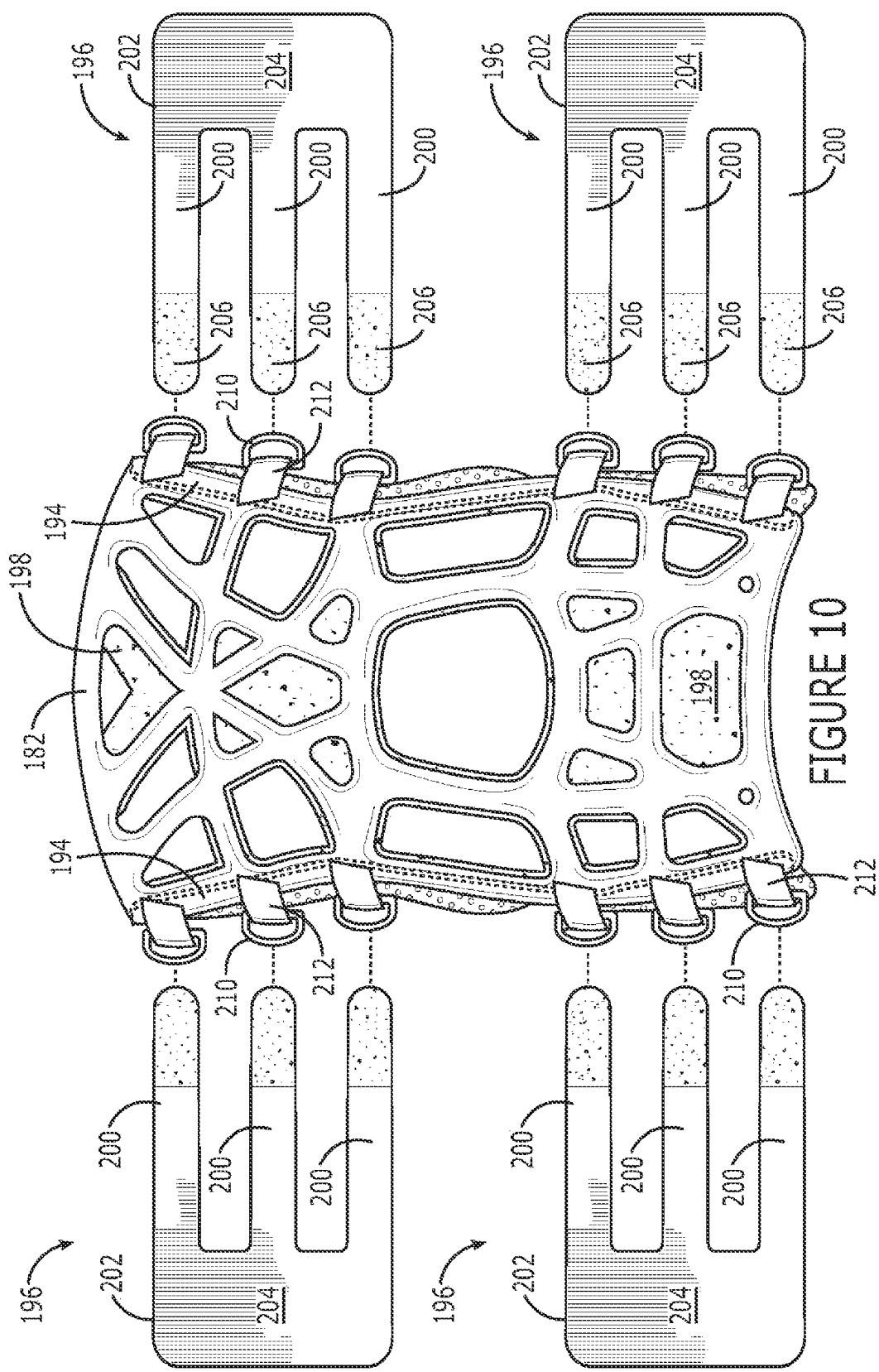
FIG. 10 is top plan view of components of a third support in accordance with an aspect of the invention.
Figure 11:
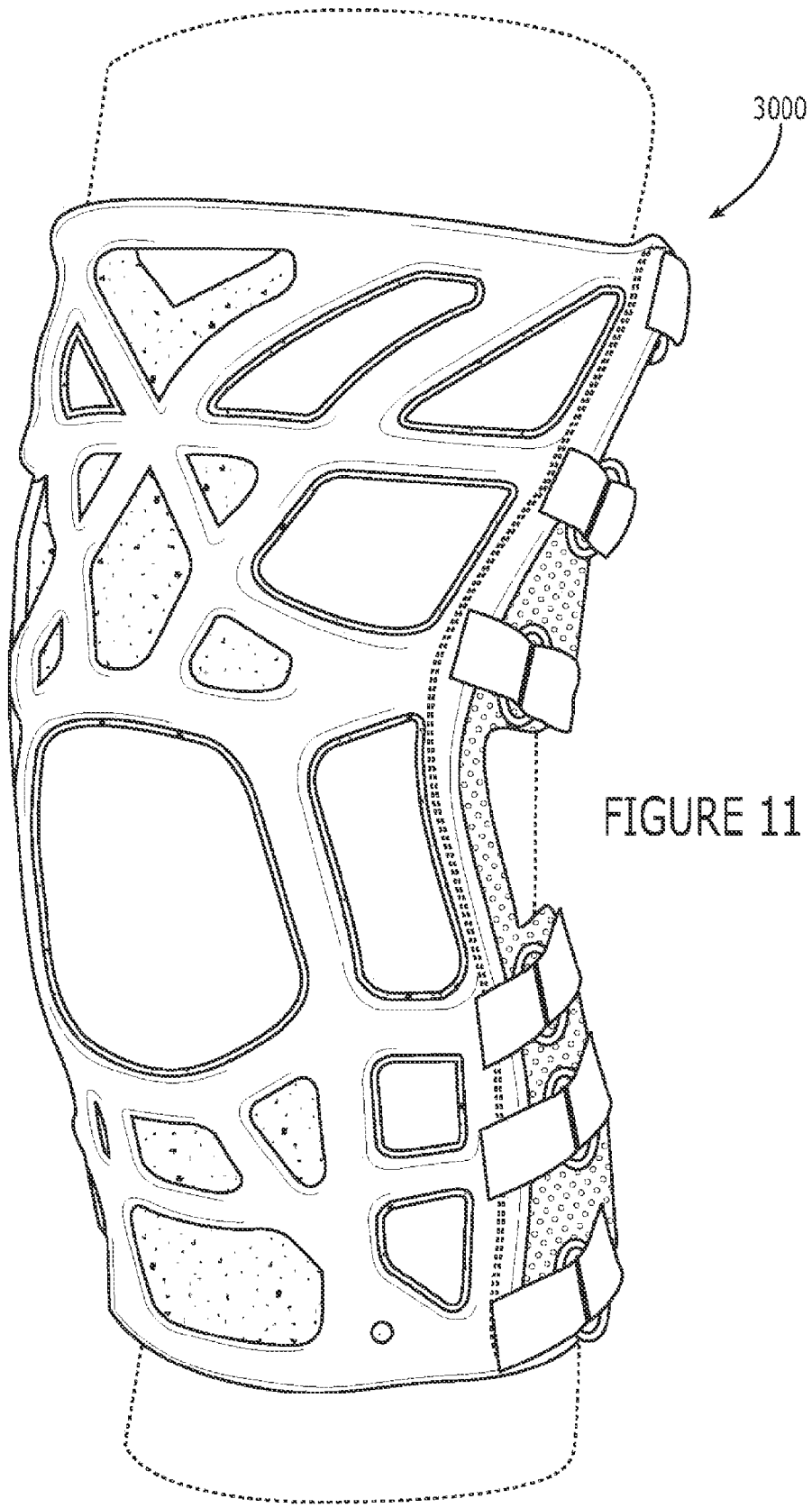
FIG. 11 is a front elevational view of the third support.
Figure 12:
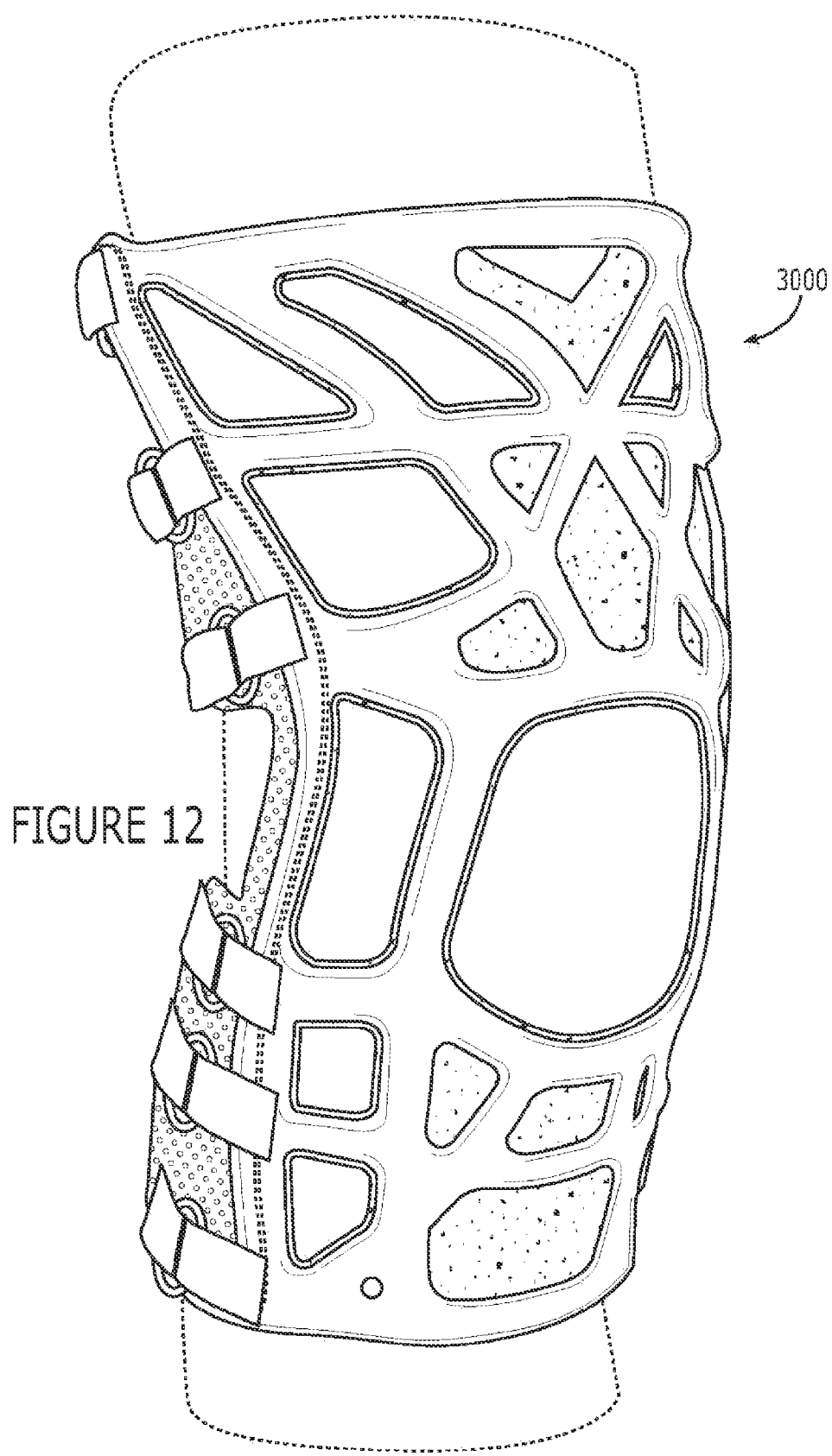
FIG. 12 is another front elevational view of the third support.

Second, the fastening mechanism includes four fastening components, each of which comprises a claw member 196 that is removable from (FIG. 10) and attachable to (FIG. 16) the framework 182. As shown in FIG. 10, each claw member 196 includes a number of fastening belts 200 joined by a fastening pad 202. First faces 204 of the claw members 196 have adjustment-fasteners 206 attached to the fastening belts 200 as shown in FIG. 10. The adjustment-fasteners 206 are adapted for engaging bands 199a,199b. For example, insofar as the outer surface 208 (FIG. 16) of the bands 199a,199b provides loops for engaging hooks, the adjustment-fasteners 206 comprise hooks for engaging the loops in hook-and-loop couplings. Each fastening belt 200 is thereby removably and adjustably disposed in engagement with the bands 199a, 199b. Furthermore, each fastening belt 200 is passed (FIG. 16) through a respective D-ring 210 (FIG. 10). Each D-ring 210 is attached to the framework 182 proximate the strut members 194 through a respective anchor strap 212 that also passes through the D-ring 210. Accordingly, prior to tensioning of the fastening belts 200 (discussed in the following), the claw members 196 are removably and adjustably attached to the framework 182 and bands 199a, 199b by way of the passing of the fastening belts 200 through the D-rings 210 and the engaging of the adjustment-fasteners 206 with the bands 199a,199b. Moreover, second faces 214 of the claw members 196 provide tension-fasteners 216 of the fastening pads 202 for engaging the bands 199a,199b. For example, insofar as the outer surface 208 (FIG. 16) of the bands 199a,199b provides loops for engaging hooks, the fasteners 206 and fasteners 216 of the fastening pads 202 comprise hooks for engaging the loops in hook-and-loop couplings. Furthermore, belts 200 (FIG. 16) of the claw members optionally have secondary fasteners 218, such as loop-fabric areas, for engaging the tension-fasteners 216 of the fastening pads 202. Thus, the tension-fasteners 216 of the fastening pads 202 are capable of removably and adjustably engaging bands 199a,199b directly and indirectly by way of the secondary fasteners 218 of the belts 200.

Figure 13:
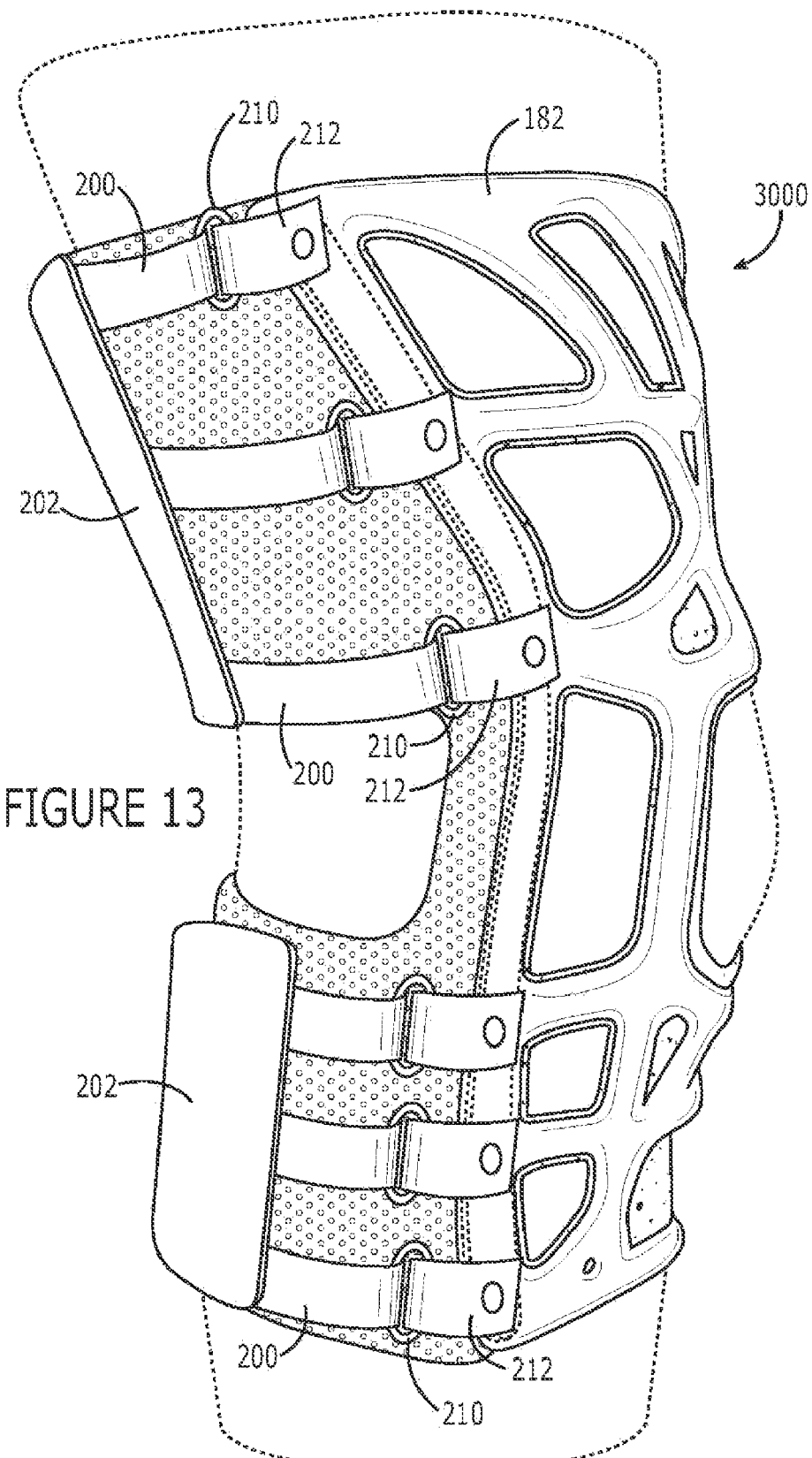
FIG. 13 is a side elevational view of the third support.
Figure 14:
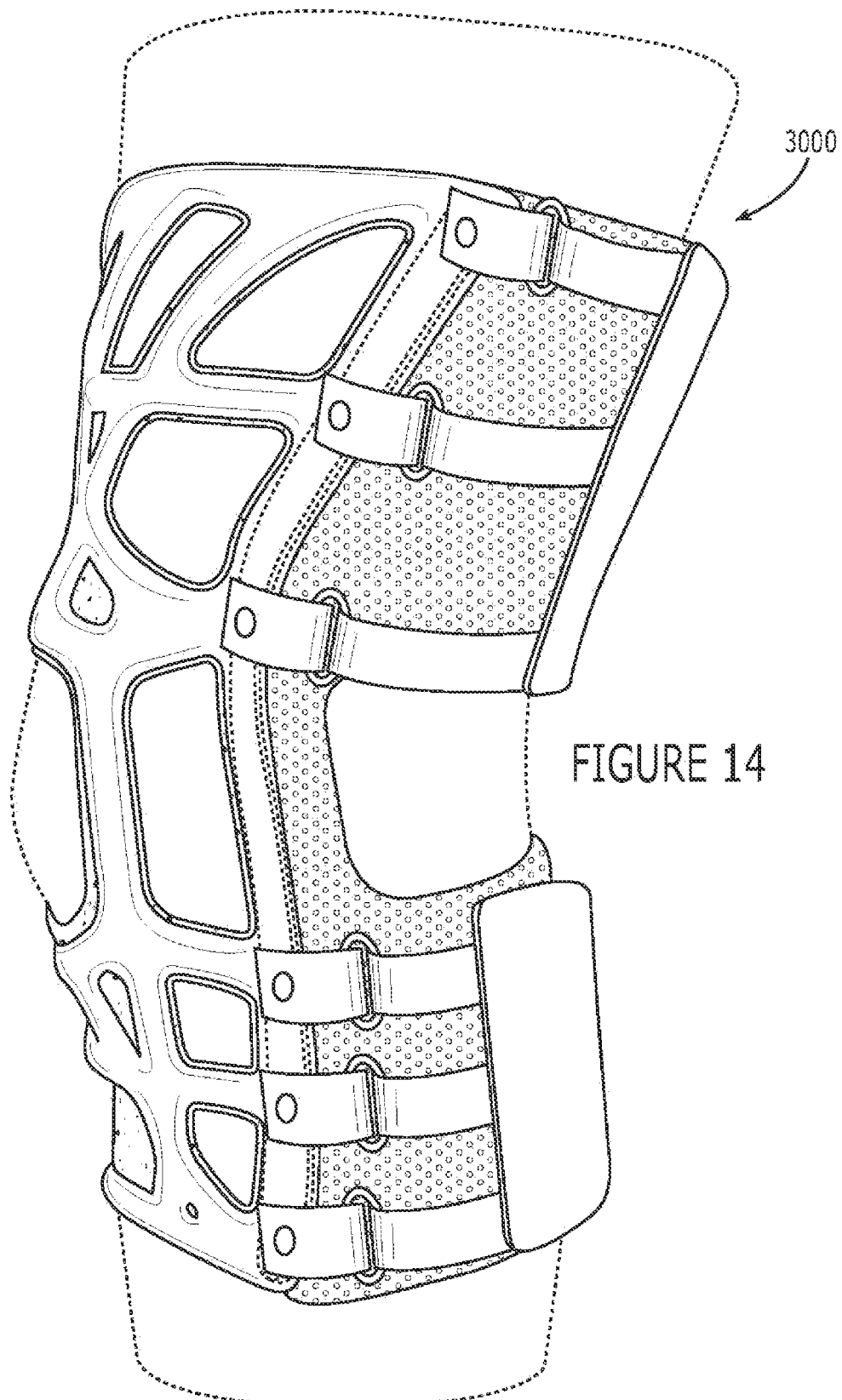
FIG. 14 is another side elevational view of the third support.
Figure 15:
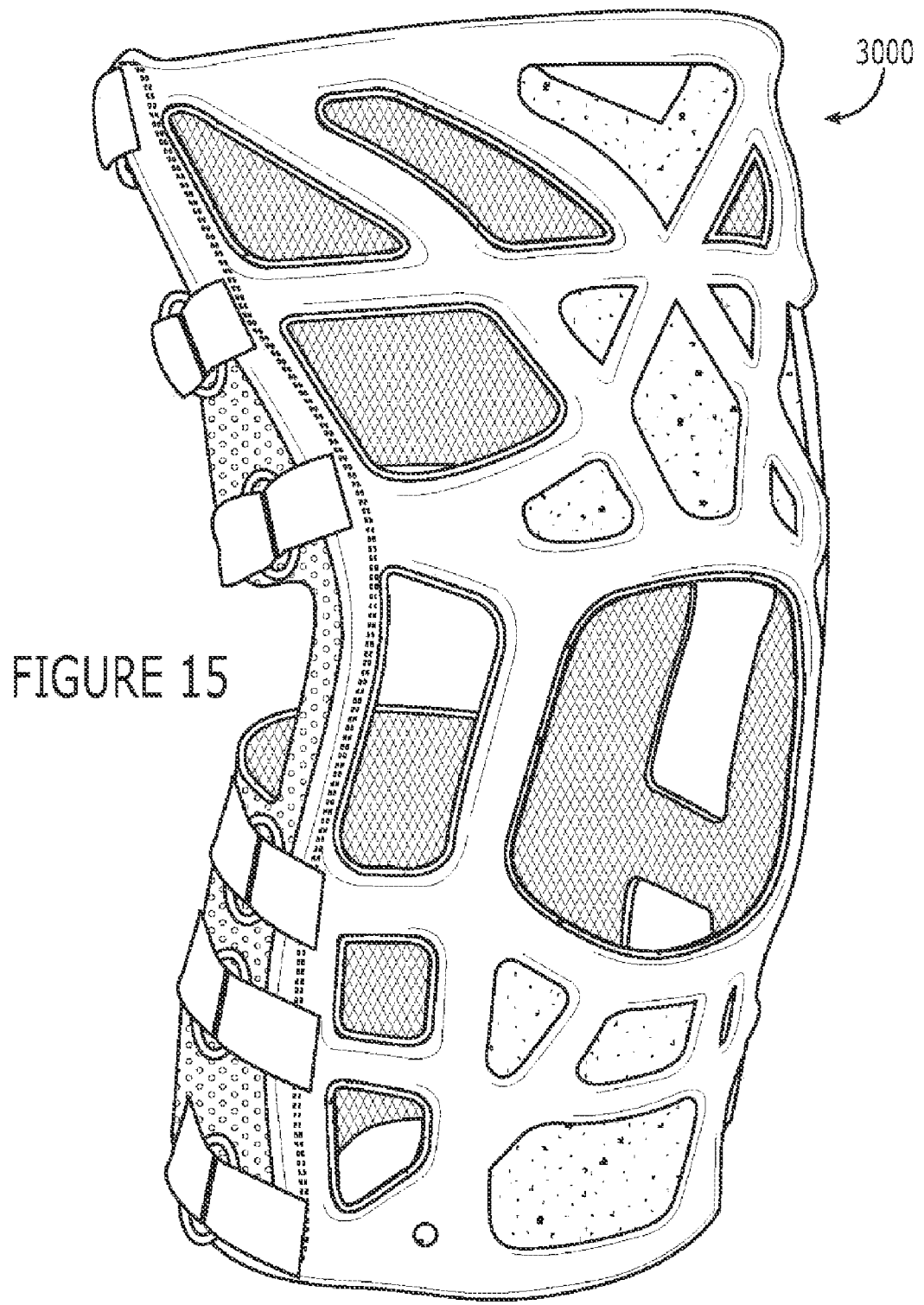
FIG. 15 is a side elevational view of the third support when not donned.
Figure 16:
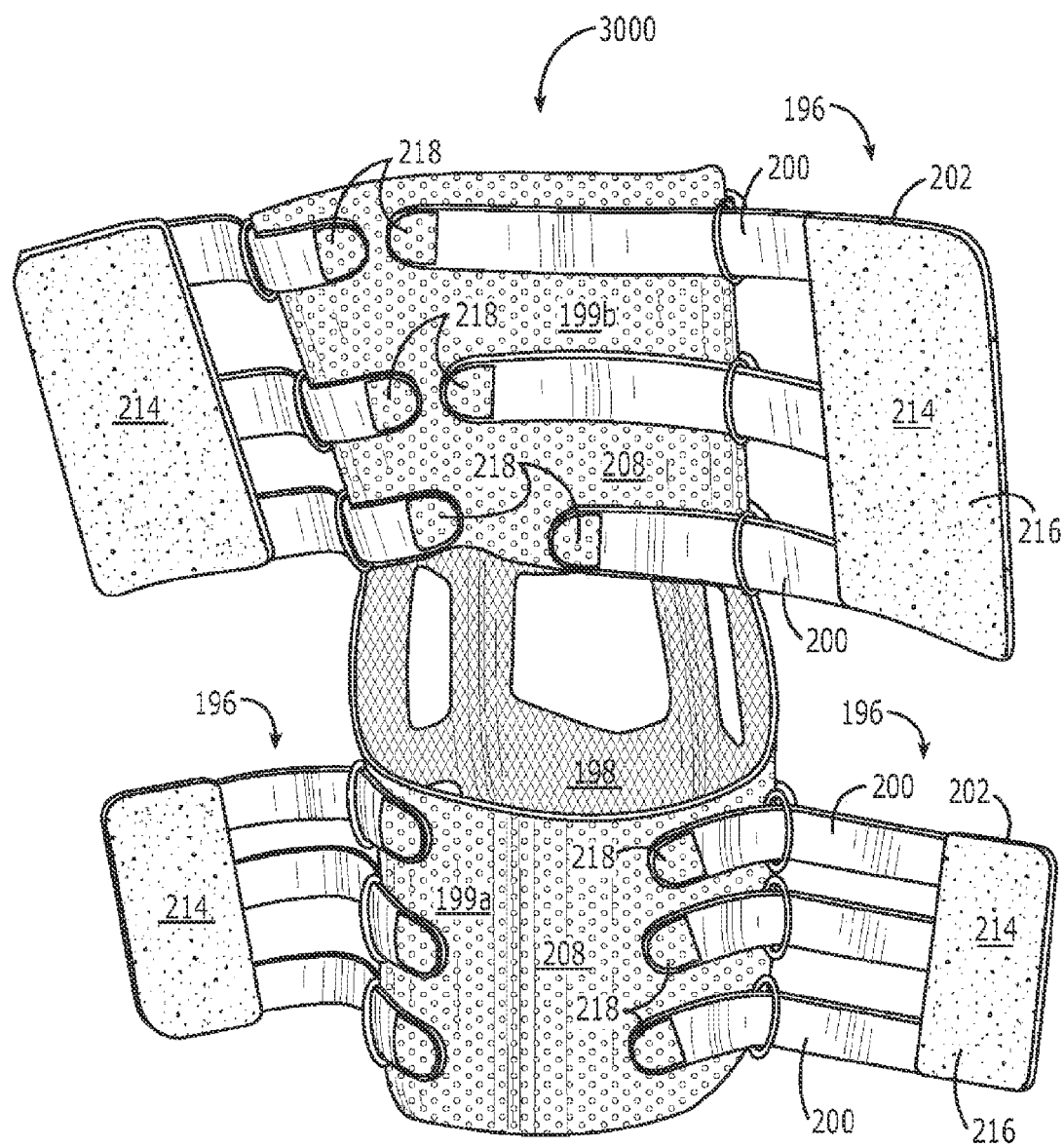
FIG. 16 is a back elevational view of the third support when not donned.
Figure 17:
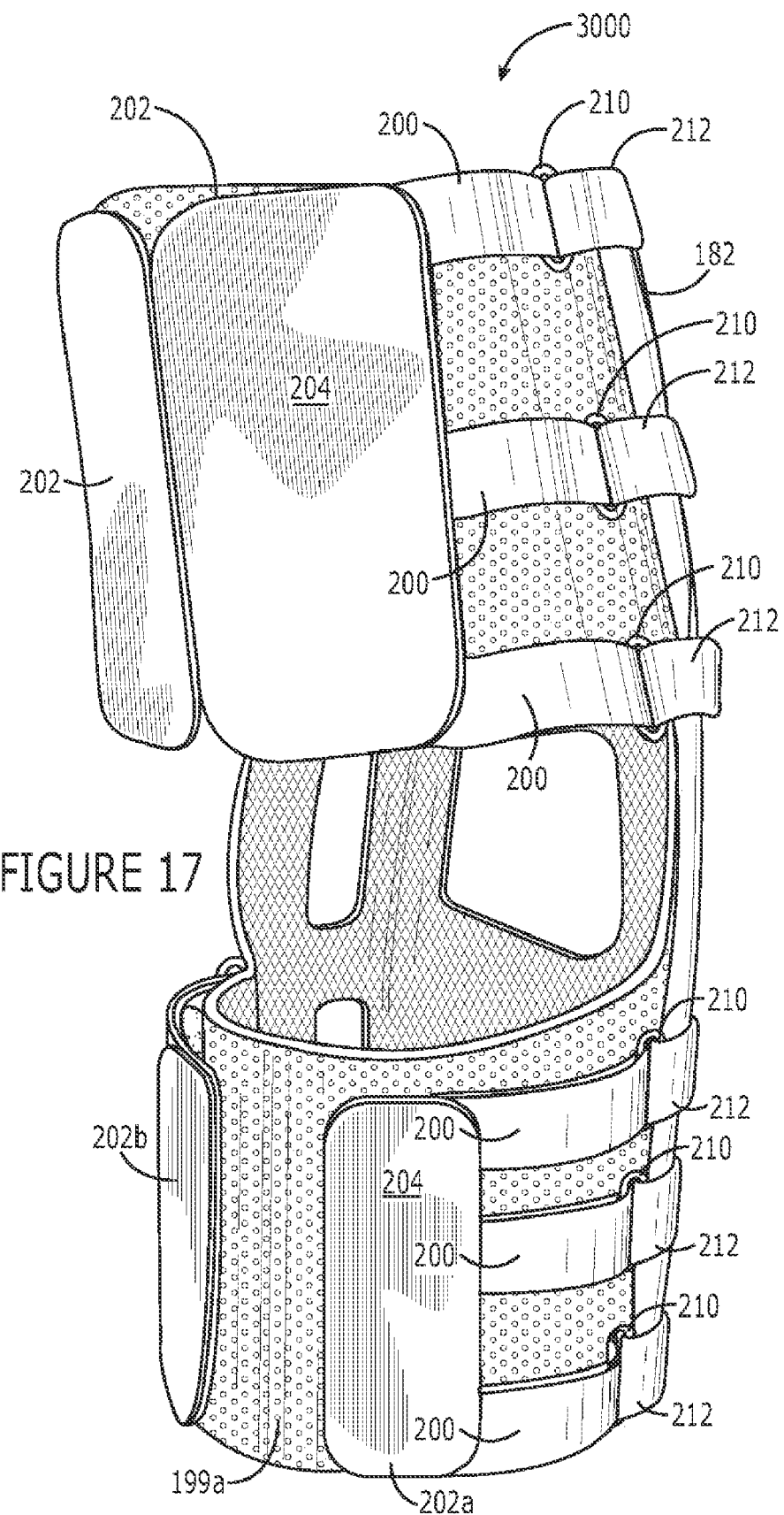
FIG. 17 is another back elevational view of the third support when not donned.

The third embodiment 3000 further provides for adjustably tensioning the framework 182 with the support donned. In this regard, the fastening pads 202 of the claw members 196 are grasped and tension is manually applied while the pads are in open positions as shown in FIG. 16, thereby tensioning the fastening belts 200. The fastening pads 202 are then disposed into abutment with the bands 199a,199b in closure positions to engage the bands 199a,199b as shown in FIG. 17. In such closure positions, the fastening pads 202 engage the bands 199a,199b to maintain tensional forces in the fastening belts 200 and, optionally, engage the secondary fasteners 218 (FIG. 16) for further supporting the maintenance of the tensional forces. Tensional forces in the fastening belts 200 are conveyed by way of the respective D-rings 210 and anchor straps 212 to the framework 182 (FIGS. 13, 14). Thus, the belts of any particular claw member are together adjustably tensioned according to the adjustable disposition of the fastening pad abutting and engaging the bands 199a,199b.

Note that though the belts of any particular claw member are together tensioned according to the disposition of the pad engaging the bands (FIG. 17), each particular belt is adjustable separately from each other belt of the same claw according to the disposition of the particular belt engaging the bands 199a,199b (FIG. 16). Thus, different portions of the framework 182 are capable of being adjustably stretched whereby the shape and contour of the framework 182 may conform to the area of the body with which it abuts.

With regard to donning the embodiment 3000 of the support, as shown in FIGS. 11-14, an area of a body such as an appendage is passed axially through the support, such as when an arm is passed into a shirt sleeve or a leg is passed into a pants sleeve. In other words, the support must be pulled over an appendage due to the attachment of the bands 199a,199b to the opposite sides of the framework 182, and cannot simply be wrapped around the area of the body to be supported.

The Fourth Embodiment of a Support

Another embodiment of a support 240 is shown in FIG. 18-22A, wherein a framework 242 extends generally in a first direction 244 and a second direction 246 thereby defining a surface for abutment with an area of a body spanning a hinge joint, such as the area of the knee or elbow. The framework 242, shown as a unitary construction of interconnected portions or members 260 forming a web, defines permanent openings 250 regardless of whether the surface is in abutment with an area of a body. Strut members 252 of the support extend generally along the first direction 244 and are attached to the framework 242 along opposite sides 254 thereof. Tensioning flaps 256 are each attached to the framework 242 along the opposite sides 254.

In this embodiment 240, the framework 242 of the support 240 is permanently attached to a sleeve 266. Examples by which the framework can be attached to the sleeve include, for example, plasticized welding, elastomeric welding, adhesive attachment, and sewing. The framework preferably is attached to the sleeve along the opposite sides 254 of the framework and, additionally, at least at some areas intermediate the opposite sides 254 of the framework so as to prevent creeping of the sleeve relative to the framework. In this respect, the portion of the sleeve extending between and at the opposite sides 254 serves as and defines a liner of the framework. Furthermore, as shown in FIG. 21, the sleeve extends between and beyond opposite sides 254 of the framework to define bands 262a,262b for receipt and engagement with tension-fasteners 264 of the tensioning flaps 256. For example, insofar as the tension-fasteners 264 are hook-fabric areas for engaging loops, the bands 262a,262b include loop fabric areas for engaging the hooks in hook-and-loop couplings.

With regard to donning the support 240, an area of a body such as an appendage is passed axially through the liner 266 such as when an arm is passed into a shirt sleeve or a leg into a pants sleeve. For example, an appendage such as a leg or an arm can be passed axially through the support such that a joint protuberance of a knee or an elbow is received in an opening 268 (FIG. 18-19) defined in and bounded by the framework.

With regard to tensioning the support, and particularly tensioning the framework 242, the tensioning flaps 256 are grasped and tensional forces are manually applied while the tensioning flaps are in open positions. The tensioning flaps 256 are then moved into closed positions in abutment with the bands 262a,262b such that the tension-fasteners 264 of the tensioning flaps 256 fasten to the bands 262a,262b. For example, in FIG. 21, tensioning flaps 256a and 256c are shown in open positions and tensioning flaps 256b and 256d are shown in closed positions. In FIGS. 20,22A tensioning flaps 256 are in closed positions engaging the bands and maintaining tensional forces in the tensioning flaps. Such tensional forces are conveyed to the framework 242 by way of the integral attachment of the tensioning flaps 256 to the framework 242.

In FIG. 22A, opposing pairs of tensioning flaps are removably fastened to the bands 262a,262b that extend there between. For example, fastening pads 256a and 256b (FIG. 22A) each removably fasten to band 262a, while fastening pads 256c and 256d each removably fasten to band 262b. The framework is thereby secured in tensioned abutment with an area of a body.

In FIG. 22B, an alternative fastening mechanism is shown and includes a first fastening component 272a and a second fastening component 272b each connected to a first distal side 274 of a framework, and a third component 272c and a fourth component 272d each connected to a second distal side 276 of the framework. With this alternative fastening mechanism, the framework engages an area of the body without an intervening liner or garment (not shown) being disposed between the framework and the body. Thus, without a garment or, in particular, a band, being present, first component 272a and third component 272c adjustably and removably fasten together, and second component 272b and fourth component 272d adjustably and removably fasten together. The components are shown as fastening together in overlapping arrangements, though other exemplary arrangements that are possible include end-to-end abutments and various other spaced arrangements of fastening by elongate fasteners such as laces, straps, or extended hook members.

Figure 18:
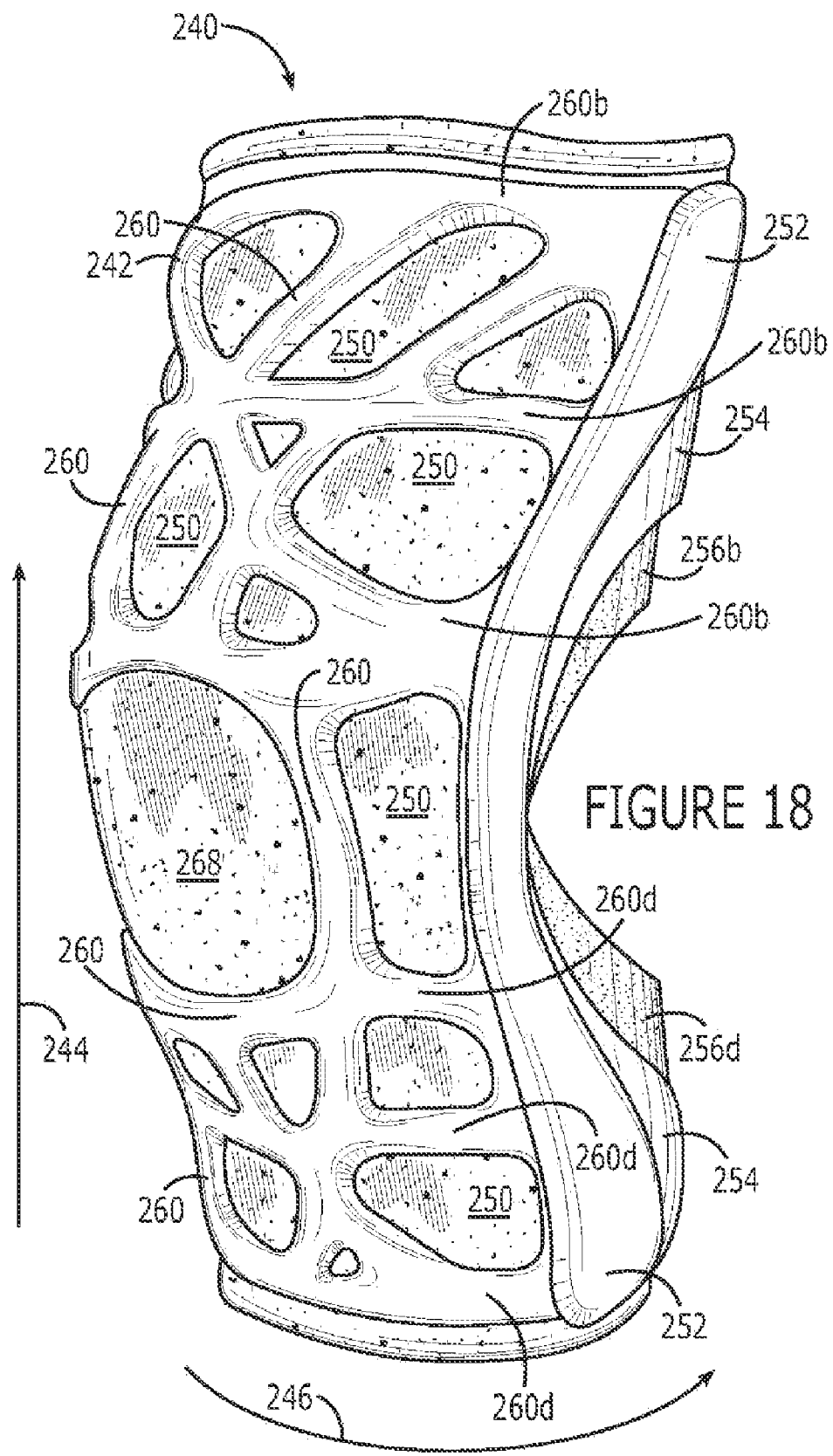
FIG. 18 is a front elevational view of a fourth support in accordance with an aspect of the invention.
Figure 19:
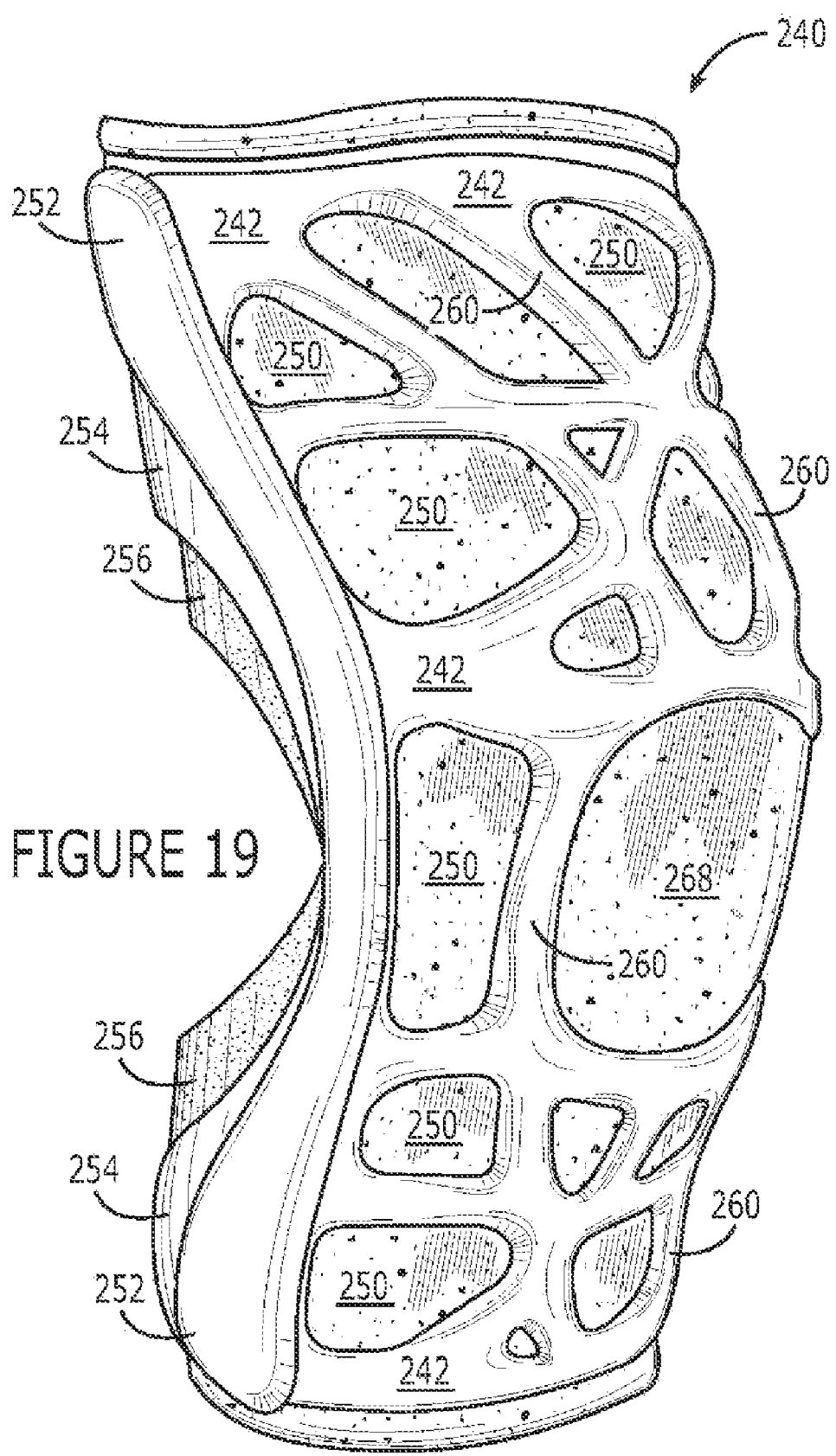
FIG. 19 is another front elevational view of the fourth support.

Returning to the embodiment 240 of FIGS. 1-22A, a first tensioning flap 256b (FIG. 21) applies first tensional forces along a first extent of a side of the framework 242, which first extent is adjacent members 260b of the framework (FIG. 18). A second tensioning flap 256d (FIG. 21) applies second tensional forces along a second extent of the side of the framework 242, which second extent is adjacent members 260d of the framework (FIG. 18). Furthermore, it will be appreciated to the Ordinary Artisan that, while the interconnected construction of members 260 of the framework 242 generally conveys tensional forces from any one member of the framework to the other members, tensional forces of particular members are correlated with tensional forces of particular tensioning flaps due to proximity and directional arrangement of the members. For example, second members 260d are arranged closer to the second tensioning flap 256d than any other tensioning flap. Furthermore, second members 260d are formed as generally liner segments along the line of extent of the second tensioning flap 256d. Thus, the tensional forces in the second members 260d are particularly correlated with the tensional forces of the second tensioning flap 256d. Moreover, insofar as the tensional forces applied to the framework 242 by the first tensioning flap 256b are different from the tensional forces applied by the second tensioning flap 256d, the tensional forces of the first members 260b are different from the tensional forces of the second members 260d. Thus, the framework 242 is capable of being adjustably stretched and its shape thereby conformed to the abutted area of the body.

It will be appreciated by the Ordinary Artisan that, due to the elastically stretchable nature of the framework, the support allows flexing of a hinge joint of the body and, in fact, contributes to such flexing. In this regard, the framework is capable of dynamically biasing a joint toward a particular state of extension or flexion. For example, the framework is capable of storing energy as a joint is bent and of releasing the stored energy as the joint is subsequently extended. In this example, one or more elastically stretchable members of the framework are increasingly tensioned and lengthen, storing kinetic energy as potential energy, as the joint is increasingly flexed and, subsequently, the elastically stretchable members are decreasingly tensioned and shorten, releasing the stored potential energy, as the joint is extended. The released energy is thereby made available as kinetic energy in movement of the knee or elbow.

In addition to the elastically stretchable framework providing joint potentiating in the embodiment 240 of the support of FIGS. 18-22A, the strut members 252 that extend generally along the first direction 244 and that are attached to the framework 242 along opposite sides 254 thereof further contribute to potentiation. In this regard, the strut members 252 are preferably formed from an elastomeric material having an elasticity that is different from the elastomeric material from which the framework is formed, whereby the side struts provide a degree of rigidity to the framework 340. Furthermore, each strut member preferably has a cross-sectional dimension that varies along the strut member such that the strut member includes a middle portion intermediate the end portions that has a cross-sectional area that is less than the respective cross-sectional areas of the end portions, whereby each strut member is more flexible in the middle portion than at the end portions. Each strut member also may have a density that varies along the first direction, wherein the density along the middle portion is less than the respective densities along the end portions, thereby making the middle portion more susceptible to hinging movement than the end portions of the strut member.

Side struts further may be removably attached to the support, if not integrally formed therewith. Advantages of such side struts include substitution of side struts having different ranges of elasticity and flexing properties for providing the desired degrees of flexibility at the hinge joint combined with degrees of rigidity in the first direction along the opposite sides of the framework. The rigidity provided preferably is focused in directions other than the direction of motion of the hinge joint. Furthermore, struts made available can allow a full range of motion of a joint or can permit motion of the joint in only a more limited range. For instance, resistance to flexing may be directly proportional to the bending displacement. A side struts also or alternatively may be formed with a channel for receiving a removable strut insert, whereby the degree of rigidity of the side strut may be varied. The rigidity of the side strut thus may be determined according to the rigidity of the removable strut insert received therein.

In further regard to this, a range of struts or strut inserts may be provided that permits a user a variety of elastic properties according to the choice, comfort and intention of the user. Thus, selective brace elasticity may range from very stretchable, thereby allowing full ranges of motion of a joint, to semirigid, thereby limiting the ranges of motion of the joint. In facilitating this, a range of struts or strut inserts may be categorized and indexed by elasticity ratings that are correlated with intended uses such as walking, running, squatting, and lifting. Furthermore, the range of struts or strut members may be categorized and indexed by elasticity ratings that are correlated with human body weights and sizes. Furthermore, the range of struts or strut members may even be categorized and indexed according to the dictates or suggestions of prescriptions prepared by health care professionals. Furthermore, patterns may be imprinted in the strut members or strut inserts that further alter the elastic properties.

The Fifth Embodiment of a Support

In FIGS. 23-25, another embodiment 340 of a support is shown that is substantially similar to the embodiment 240 of the support of FIGS. 18-22A. In this regard, for example, the framework 342 of FIGS. 23-25 is capable of storing energy as a joint is bent (FIG. 23) and of releasing the stored energy as the joint is subsequently extended (FIG. 24). In this example, one or more elastically stretchable members 360 of the framework 342 are increasingly tensioned and lengthen, storing kinetic energy as potential energy, as the joint is increasingly flexed (FIG. 23) and, subsequently, the elastically stretchable members 360 are decreasingly tensioned and shorten, releasing the stored potential energy as kinetic energy, as the joint is extended (FIG. 24).

Similarly, strut members extend generally along and are attached to the framework along opposite sides thereof and contribute to joint potentiation of the support. In this regard, for example, a strut member (comprising end portions 352*a,c* and intermediate portion 352*b*) preferably is elastically stretchable and is formed from an elastomeric material having an elasticity that is different from the elastomeric material from which the framework 342 is formed, whereby the side strut provides some degree of rigidity along the side of the framework 342. As shown in FIG. 23-24, the strut member has a cross-sectional dimension that varies along the strut member such that the cross-sectional area of the intermediate portion 352*b* is less than the respective cross-sectional areas of the end portions 352*a*,352*c*. The reduced cross-sectional area in this example permits the strut member to be more flexible in the middle portion than at the end portions thereof.

Different from the embodiment of the support 240, the embodiment 340 of the support of FIGS. 23-25 includes a removable member 370 that is positionable proximate to a permanent opening 372 defined and completely bounded by the framework 342. When positioned as shown in FIGS. 23-25, the removable member 370 is disposed between the permanent opening 372 of the framework and an area of the body to be supported. Moreover, a posterior face (not shown) of the removable member 370 is contoured to receive a joint protuberance of the body. For example, insofar as the support 340 is adapted to receive an appendage such as a leg or arm, the removable member 370, particularly the posterior face thereof, is contoured to receive a protuberance of the knee or elbow, respectively.

With the removable member 370 positioned proximate the permanent opening 372 and disposed between the opening and an area of a body, the removable member 370 surrounds a joint protuberance and preferably comprises an alignment ring that applies pressure along a perimeter of the ring to each side of the protuberance and that promote proper positioning of the protuberance and healthy joint function. Furthermore, as a consequence of the adjustable tensioning of the framework, the pressure applied by the removable member is adjustable. In one embodiment, the removable member comprises a patellar ring shaped for receiving, surrounding and supporting the patella (kneecap) to promote maintenance of the kneecap in its proper position and to prevent the kneecap from dislodging from the femoral groove.

In addition to the permanent opening 372, other permanent openings 374 are defined between interconnected members of the framework 342. As shown in FIGS. 23-25, an anterior face of the removable member 370 is contoured to receive interconnected members of the framework 342 for securing the removable member relative to the permanent opening 372. Likewise, the removable member extends within the permanent opening 372 and may further extend within an additional opening 374 to effect an interlocking engagement of the removable member with the framework 342.

The removable member 370 is semirigid to support a joint protuberance but is also flexible and extensible to allow for joint motion. The removable member also preferably is resilient and, thus, is capable of repeated compression and recovery to allow for its placement into the support 340 and removal therefrom. For example, the removable member 370 and framework 342 are optionally adapted to permit forced passage of the removable member through the first opening 372 for manual placement and removal of the removable member 370 even after the support is donned. Also as shown, the framework includes a liner that does not include an opening registering with the permanent opening 372 in the framework 342, and the removable member 370 is positioned through the permanent opening 372 for disposition between the framework and the liner. Alternatively, the removable member may be positionable between the liner and the body; in this case, the liner preferably is sufficiently flexible to permit extension of the removable member within the opening and engagement of a contour of the removable member with one or more portions of the framework. The liner additionally may include a pocket for receiving the removable member and retention of the removable member between the framework and the joint at the permanent opening 372.

Examples of materials of which the removable member can be constructed include, but are not limited to, plastics, rubber, and various other materials.

The Sixth Embodiment of a Support

Figure 26:
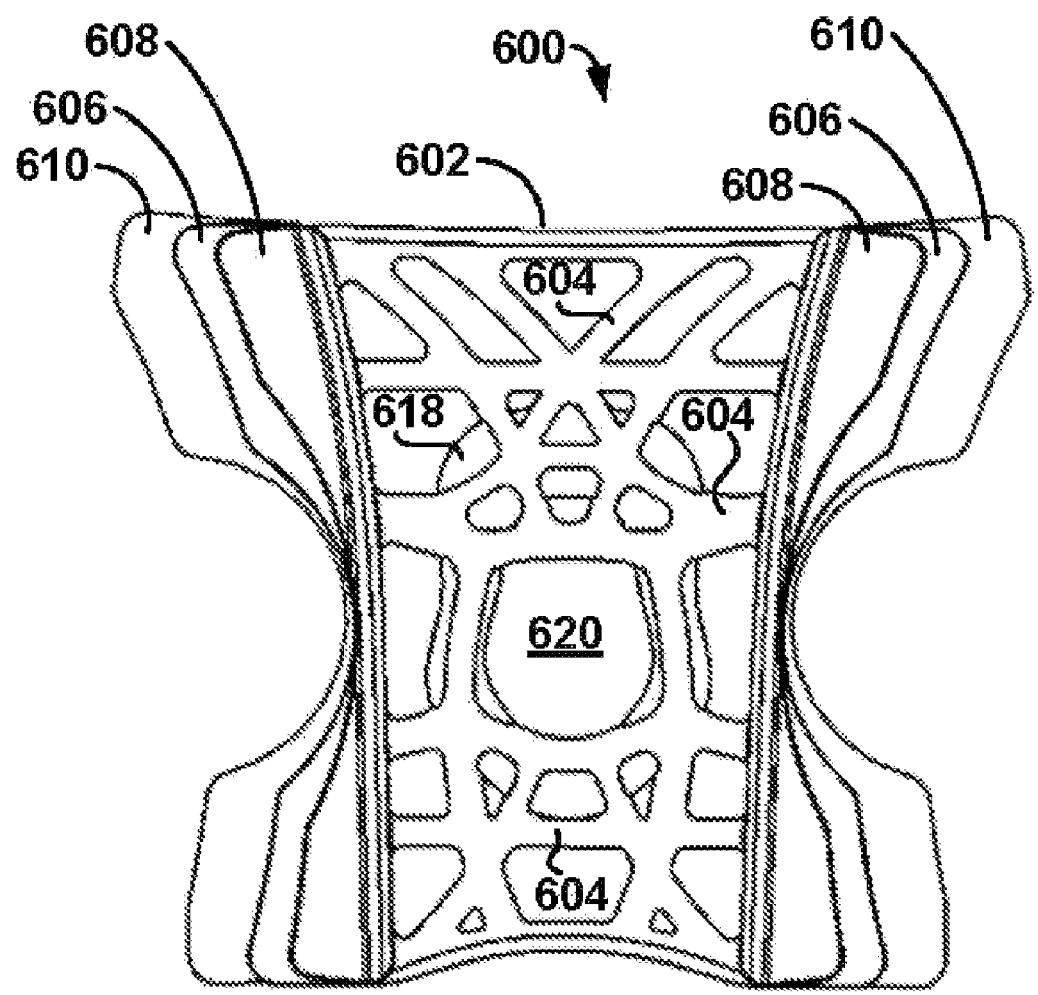
FIG. 26 is a front plan view of a sixth support in accordance with an aspect of the invention.
Figure 27:
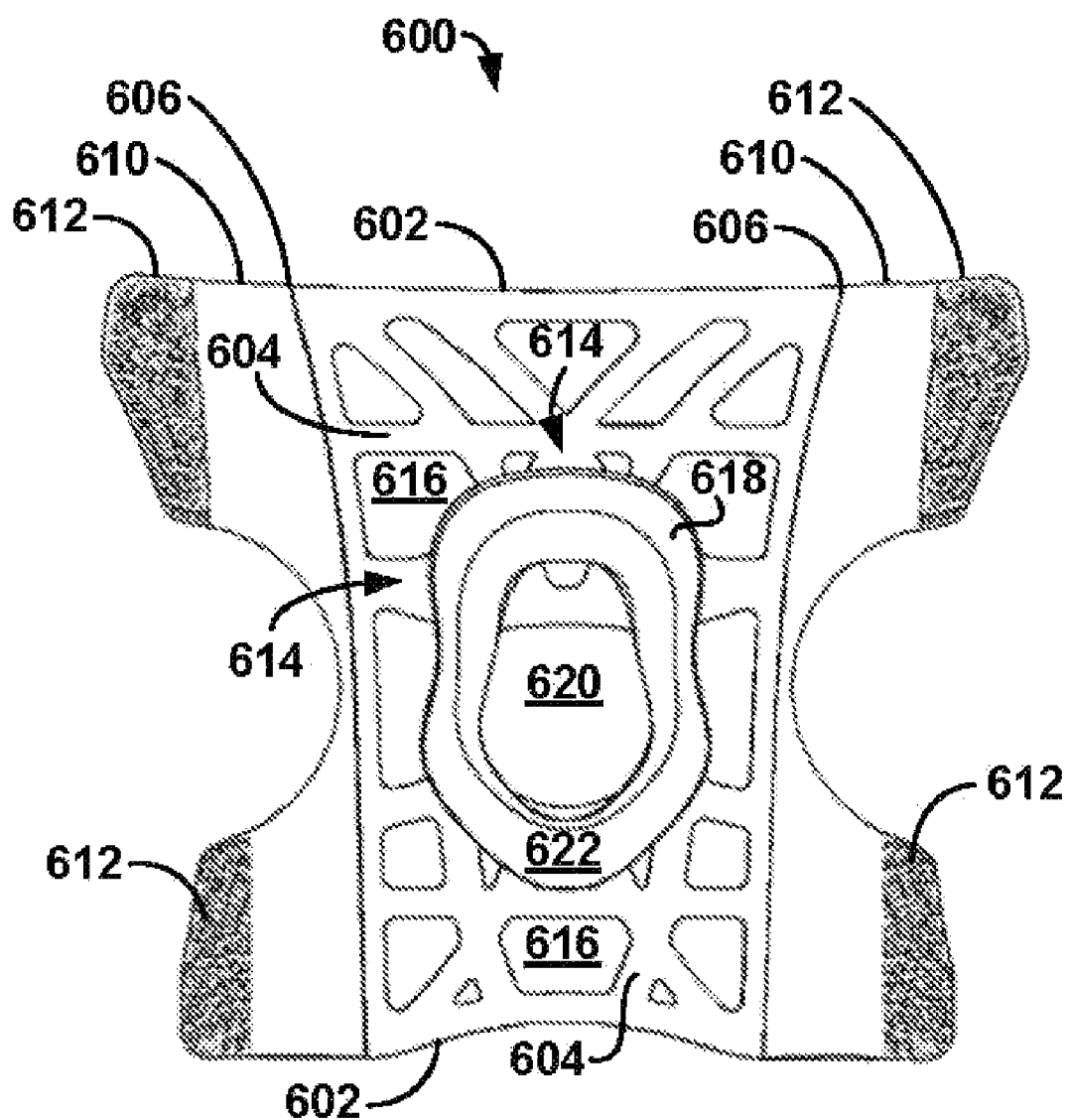
FIG. 27 is a back plan view of the sixth support.

In a sixth embodiment as illustrated in anterior view in FIG. 26 and posterior view in FIG. 27, an embodiment 600 of a support includes a framework 602 of interconnected, elastically stretchable members 604 forming a web. The framework 602 is joined adjacent distal margins or opposite sides 606 thereof to side strut members 608 (FIG. 26) and a tensioning mechanism such as tensioning flaps 610. Tension-fasteners 612 (FIG. 27) of the tensioning flaps 610 are for removably fastening the support into abutment with an area of the body such that the area is abutted by the surface 614 of the framework. Specifically, the tension-fasteners 612 are adapted for fastening to a garment or band. For example, insofar as a garment provides loop-fabric, the tension-fasteners 612 provide hook-fabric for engaging the garment in hook-and-loop couplings. The interconnected members 604 of the framework define permanent openings 616 in the framework 602 regardless of whether the surface 614 is secured in abutment with an area of a body.

Figure 30:
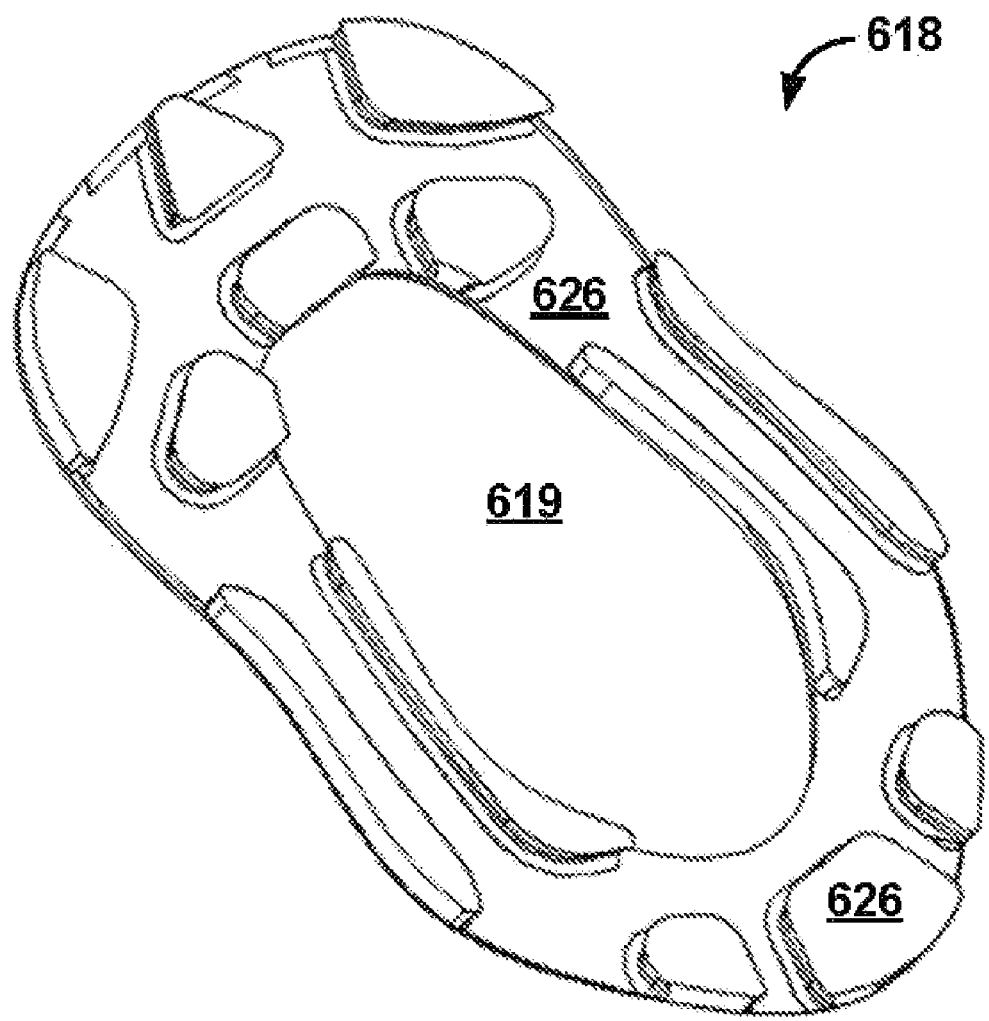
FIG. 30 is a perspective view of an anterior side of a component of the sixth support.
Figure 31:
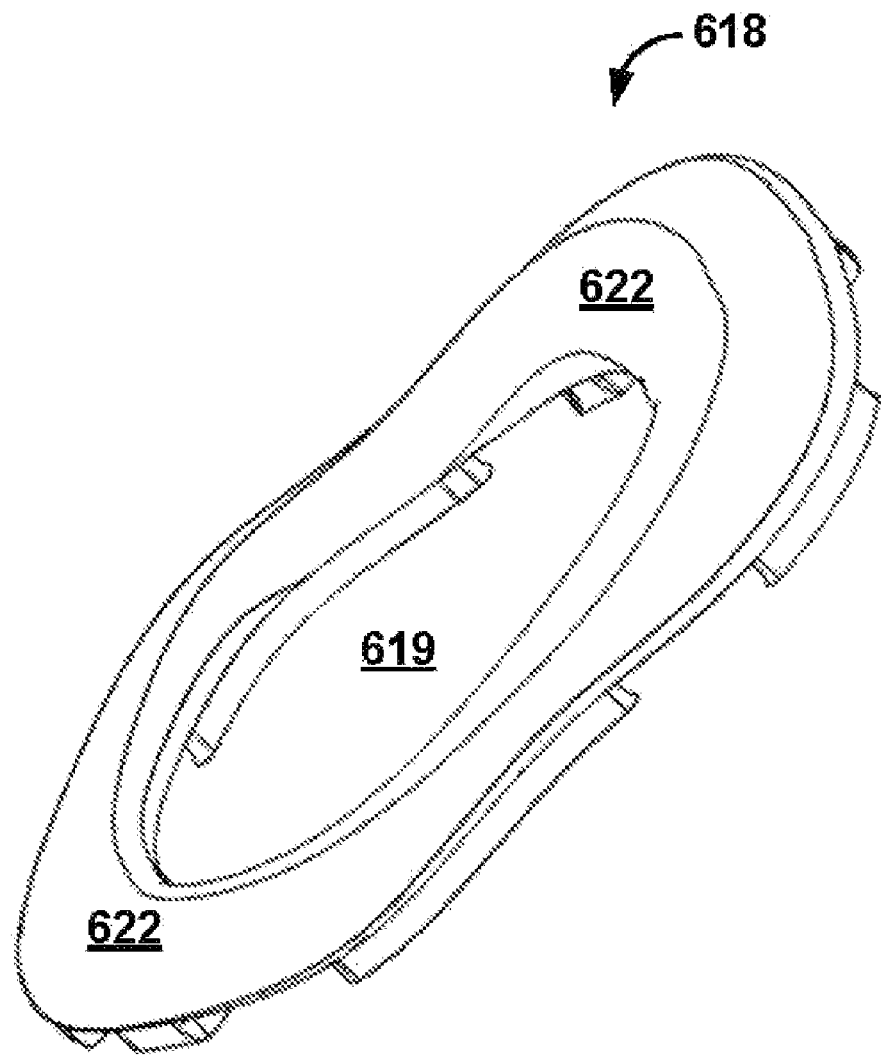
FIG. 31 is a perspective view of a posterior side of the component of FIG. 30.

A removable member 618 is shown in FIGS. 26-27 positioned proximate to a permanent opening 620 defined in the framework 602. When so positioned, the removable member is disposed between the permanent opening 620 of the framework 602 and an area of a body to be supported. As shown in FIGS. 27, 31, 33, a posterior face 622 of the removable member 618, defining an opening 619 (FIGS. 30-33), is contoured to receive a joint protuberance of the body. For example, insofar as the support 600 is adapted for the surface 614 (FIG. 27) to abut an appendage such as a leg or arm, the removable member is contoured to receive a protuberance of a knee or elbow, respectively.

Figure 28:
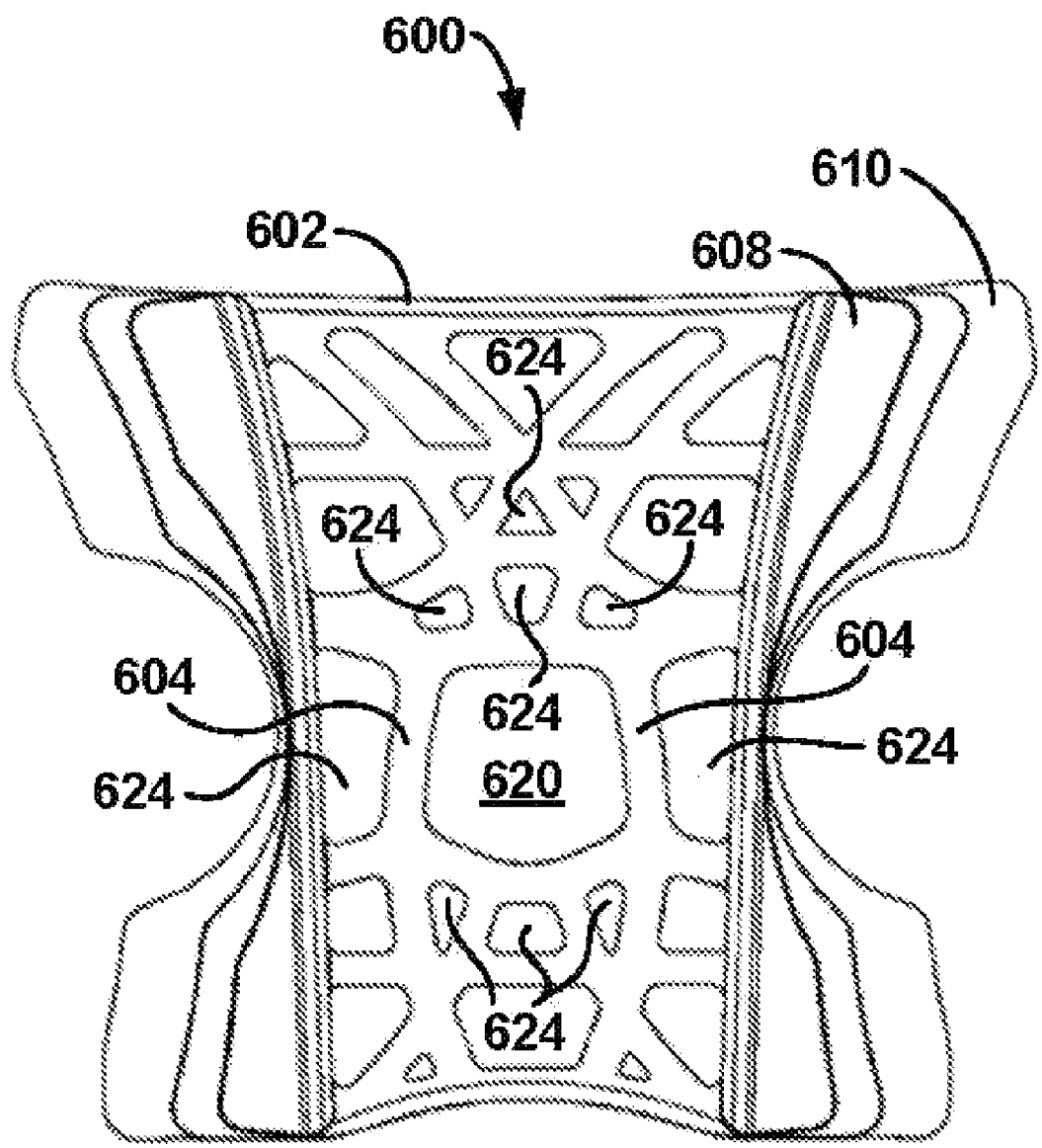
FIG. 28 is a front plan view of components of the sixth support.

Additionally to the permanent opening 620, permanent openings 624 are defined between the interconnected members 604 of the framework 602 as shown in FIG. 28. As shown in FIGS. 30-32, an anterior face 626 of the removable member 618 is contoured to receive interconnected members of the framework for securing the removable member 618 relative to the permanent opening 620. Likewise, the removable member 618 extends within the permanent opening 620 and permanent openings 624 to effect an interlocking engagement of the removable member 618 with the framework 602 as shown in FIG. 26.

A particular arrangement of elastomeric segments of the framework 602 is perhaps best illustrated with reference to FIG. 29A. As shown in FIG. 29A, the framework 602 includes a first exterior lateral segment (1EL); second exterior lateral segment (2EL); first exterior transverse segment (1ET); second exterior transverse segment (2ET); first interior transverse segment (1IT); second interior transverse segment (2IT); third interior transverse segment (3IT); fourth interior transverse segment (4IT); first interior lateral segment (1IL); second interior lateral segment (2IL); third interior lateral segment (3IL); and fourth interior lateral segment (4IL); fifth interior lateral segment (5IL); sixth interior lateral segment (6IL); seventh interior lateral segment (7IL); and eighth interior lateral segment (8IL).

As illustrated, the four exterior segments (1EL,2EL,1ET,2ET) collectively define a perimeter of the framework 602. Additionally, each of the first, second, third, and fourth interior transverse segments (1IT,2IT,3IT,4IT) extends between and interconnects the first and second exterior lateral segments (1EL,2EL); each of the first, second, fifth, and sixth interior lateral segments (1IL,2IL,5IL,6IL) extends between and interconnects the first exterior transverse segment (1ET) and the second interior transverse segment (2IT), and intersects and interconnects the first interior transverse segment (1IT); each of the third and fourth interior lateral segments (3IL,4IL) extends between and interconnects the second exterior transverse segment (2ET) and the second interior transverse segment (2IT), and intersects and interconnects the third and fourth interior transverse segments (3IT,4IT); and each of the seventh and eighth interior lateral segments (7IL,8IL) extends between and interconnects the second exterior transverse segment (2ET) and the third interior transverse segment (3IT), and intersects and interconnects the fourth interior transverse segment (4IT).

Moreover, as further illustrated in FIG. 29A, an alignment opening is defined by the second interior transverse segment (2IT), which extends along and bounds a top of the alignment opening; the third interior transverse segment (3IT), which extends along and bounds a bottom of the alignment opening; the third interior lateral segment (3IL), which extends along and bounds a first side of the alignment opening; and the fourth interior lateral segment (4IL), which extends along and bounds a second side of the alignment opening.

This particular arrangement of elastomeric segments of the framework further is representative of, for example, the framework of FIGS. 26-29, as well as the frameworks of FIGS. 1, 10, 23, 48, and 53.

It further is explicitly recognized that left and right sides and top and bottom sides of the framework collectively define a perimeter of the framework that the left and right sides of the perimeter of the framework comprise first and second exterior lateral segments and that the top and bottom sides of the perimeter of the framework comprise first and second exterior transverse segments.

Additionally, it is explicitly recognized that a particular segment itself may be characterized as comprising a plurality of segments joined in series. As such, each of the foregoing interior segments, for example, may be characterized as a subset of segments, with such subset comprising one or more segments.

Figure 29:
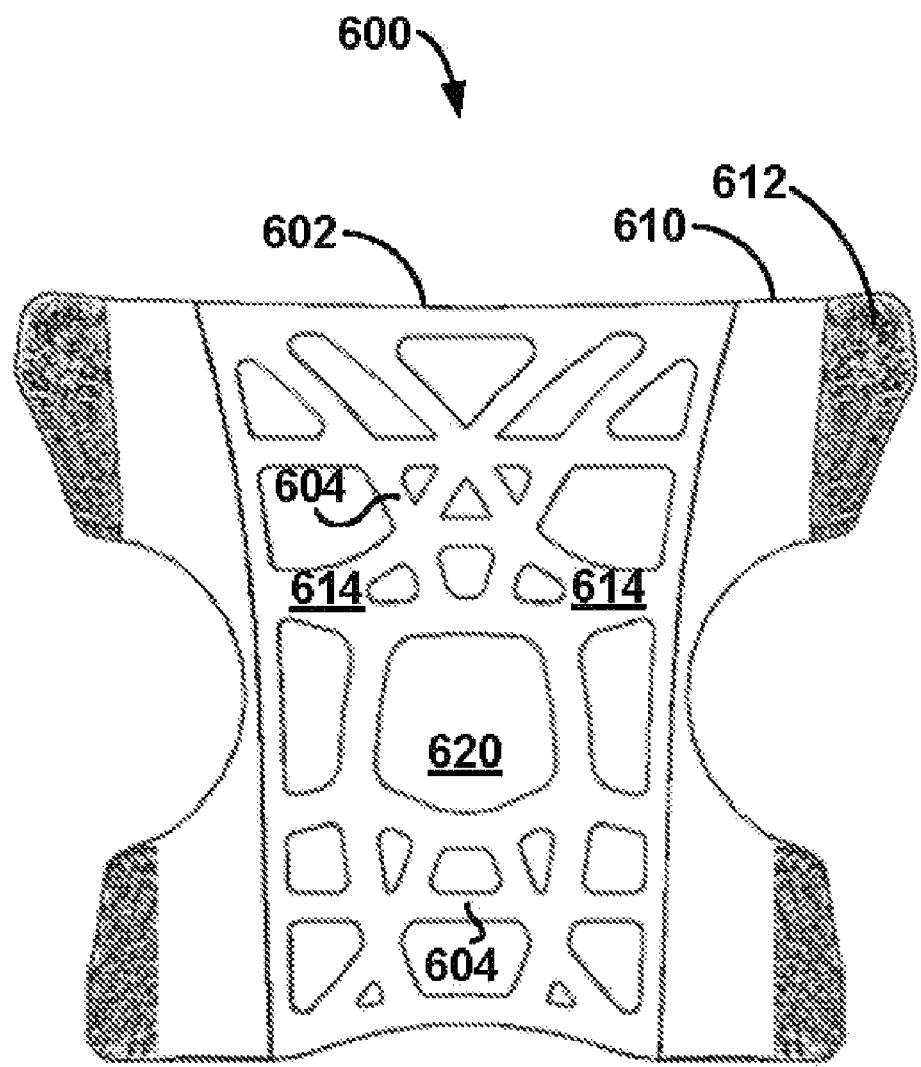
FIG. 29 is a back plan view of components of the sixth support.
Figure 29A:
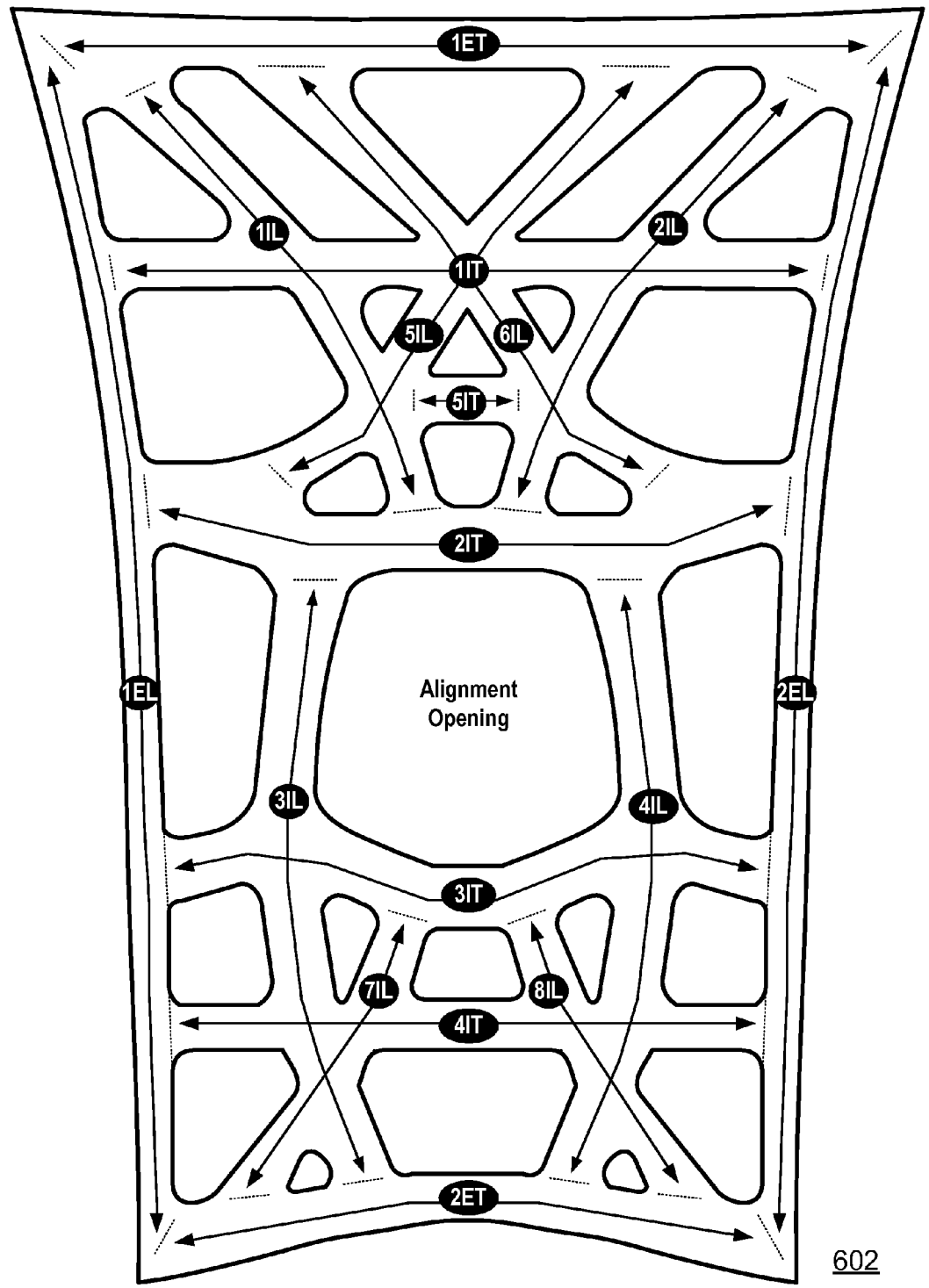
FIG. 29A is a schematic view of a particular arrangement of elastomeric segments of a framework in accordance with one or more preferred embodiment of the invention.

The support also is shown without the removable member 618 in anterior view and posterior view in FIGS. 28 and 29, respectively, in order to illustrate that the support can be utilized without the removable member 618, as desired.

The Seventh Embodiment of a Support

In a seventh embodiment 700 as illustrated in posterior view in FIG. 34, a support includes a framework 702 of interconnected, elastically stretchable members 704 forming a web. The framework 702 is joined adjacent distal margins or opposite sides 706 thereof to a tensioning mechanism, such as tensioning flaps 710 having tension-fasteners 712 for removably fastening the support into abutment with an area of a body. Embodiment 700 of the support of FIG. 34 is to be understood as similar to that of the support of FIGS. 26-27. In a prominent difference between these two embodiments, however, embodiment 700 includes two tensioning flaps 710 and two tension-fasteners 712 (FIG. 34), each of which extends along the entire length of the framework in the first direction, while embodiment 600 includes four tensioning flaps 610 and four tension-fasteners 612 (FIG. 27), pairs of which are spaced along the length of the framework in the first direction.

The Eighth Embodiment of a Support

In an eighth embodiment 800 as illustrated in posterior view in FIG. 35 and anterior view in FIG. 36, a support includes a framework 802 of interconnected, elastically stretchable members 804 forming a web. The framework is joined adjacent distal margins or opposite sides 806a,806b thereof to a tensioning mechanism, such as respective tensioning flaps 810a,810b. The tensioning flaps adjustably and removably fasten together for maintaining the support 800 in abutment with an area of a body, by encircling the body without regard to any garment or band. When the support 800 is fully encircled about the body (not shown), the tensioning flap 810b overlaps the tensioning flap 810a such that the tension-fastener 812b (FIG. 35) overlaps and engages the tension-fastener 812a (FIG. 36). For example, insofar as the tension-fastener 812a is a loop-fabric area for engaging hooks, the tension-fastener 812b is a hook-fabric area for engaging the loops in hook-and-loop couplings. In this regard, the support 800 of FIGS. 35-36 is to be understood as similar to the support 270 of FIG. 22B. A prominent difference between these embodiments is understood by noting that tensioning flaps 810a,810b and tension-fasteners 812a,812b (FIG. 35, FIG. 36) are each continuous and uninterrupted while the fastening components 272a,272b (FIG. 22A) are spaced by arcuate cutouts.

The Ninth Embodiment of a Support

A ninth embodiment 900 is illustrated in FIGS. 37-38, wherein the support is to be understood as similar to the support 340 of FIGS. 23-25. A prominent difference between these embodiments is understood by noting that the permanent openings 372,374 of embodiment 340 (FIG. 18) are defined between elastically stretchable portions or members that are formed as generally linear segments, whereas the permanent openings 902 of embodiment 900 (FIGS. 37-38) are defined between elastically stretchable portions that are more arcuately formed such that the openings 902 defined in the framework are generally elliptical and circular in shape. Embodiment 900 further includes a removable member 904 disposed in interlocking engagement with the framework 906 that includes a surface 908 for bearing a marking, such as, for example, the trademark BIKE. Other examples of markings include personal names and preferences; identifications or depictions of popular characters, such as particular athletes; and indications of left and right for differentiating supports for different sides of the body.

The Tenth Embodiment of a Support

A tenth embodiment 10000 of a support is illustrated in FIG. 39, wherein the support is to be understood as similar to the support 340 of FIGS. 23-25. The tenth embodiment 10000 differs in that the support includes additional tensioning members in the form of rotary closure devices 1010,1020. Such closure devices are utilized for additionally tensioning the framework in its abutment with the supported area of the body. Such general closure devices 1010,1020 further include ratcheting mechanisms and are well known in general for other applications outside of the present invention, and are disclosed, for example, in U.S. Pat. No. 5,042,177 to Schoch, titled "Rotary Closure for a Sports Shoe, Especially a Ski Shoe," which patent is hereby incorporated herein by reference. Each closure device 1010,1020 is similar to the other, and each includes two tensioning lines that extend from one side of the framework to the other. Thus, for example, as shown in FIG. 39, tension line 1030 extends over and back across band 1050, and tension line 1040 extends over and back across band 1050 (which includes Velcro™ fasteners for fastening of the flaps 1060,1070). Each tension line extends through a loop secured to the other side of the framework, and anchors back at the side of the closure devices 1010,1020. Accordingly, by ratcheting the closure devices and selectively drawing the tension lines therein, the opposite sides of the framework are drawn toward one another in defined increments for micro adjustment of the support. Closure device 1010 includes a corresponding arrangement (not shown).

The Eleventh Embodiment of a Support

An eleventh embodiment 11000 of a support is illustrated in FIG. 40 and includes an exposed, elastically stretchable framework 1110, which is similar to the frameworks discussed above with the other embodiments. Unlike the embodiments discussed in detail to this point, however, the framework 1110 is directly and permanently attached to a sleeve 1120 (portions of which are seen through the framework openings in FIG. 40), and the framework 1110 itself completely encircles the body. The embodiment 11000 further does not include a fastening mechanism that removably fastens to a garment for adjustably tensioning of the framework. In this regard, the embodiment 11000 of the support is simpler to use. The sleeve 1120 also preferably is air permeable for ventilation of the covered area of the body.

To don this support, one need only pull the support over one's foot and up one's leg and position the knee protuberance within the protuberance opening 1150 of the framework. To assist in pulling (both on and off), the support includes pull tab 1130 (generally for pulling the support on) and pull tab 1140 (generally for pulling the support off).

The Twelfth Embodiment of a Support

A twelfth embodiment 12000 of a support is illustrated in FIG. 41 and includes an elastically stretchable framework 1210 like the one of FIG. 40. Framework 1210 is permanently attached to a sleeve 1220 (portions of which are seen through the framework openings in FIG. 41), and the framework 1210 itself completely encircles the body. The embodiment 12000 further does not include a fastening mechanism that removably fastens to a garment for adjustably tensioning of the framework. In this regard, the embodiment 12000 of the support is simpler to use. The sleeve 1220 also preferably is air permeable for ventilating of the covered area of the body.

To don this support, one need only pull the support over one's hand and up one's arm and position the elbow protuberance within the protuberance opening 1250 of the framework.

The Thirteenth Embodiment of a Support

A thirteenth embodiment 13000 of a support is illustrated in FIG. 42 and is the same in overall construction as the twelfth embodiment 12000. Indeed, the thirteenth embodiment 13000 differs principally only in that the axial length of the support is less than that of the twelfth embodiment 12000, as is readily apparent from a comparison of FIG. 41 and FIG. 42.

The Fourteenth Embodiment of a Support

A fourteenth embodiment 14000 of a support is illustrated in FIG. 43 and represents a forearm sleeve in accordance with the invention. This embodiment 14000 is similar to the embodiments of FIGS. 41-42 with the notable exception that the forearm sleeve does not span the elbow of the body but, rather, simply spans an extent covering the forearm below the elbow. As such, the elastically stretchable framework 1410 does not include a protuberance opening, but framework 1410 does include the plurality of permanent openings and is permanently attached to the sleeve. A similar, additional embodiment somewhat shorter in length (not shown) comprises a shin sleeve that is dimensioned to be worn just below the knee.

The Fifteenth Embodiment of a Support

A fifteenth embodiment 15000 of a support is illustrated in FIG. 44 and includes a shirt with sleeves, each of which includes an elastically stretchable framework 1510,1520. Moreover, each framework 1510,1520 corresponds to the framework 1210 of the twelfth embodiment 12000 described above and disclosed in FIG. 41.

The Sixteenth Embodiment of a Support

A sixteenth embodiment 16000 of a support is illustrated in FIG. 45 and is the same as the shirt of FIG. 44 except that the frameworks 1610,1620 of the sleeves are joined by an intermediate framework 1630 that extends across the midsection of the shirt and that abuts an area of the torso of the body. This intermediate framework 1630 serves not only to aesthetically join the frameworks 1610,1620 of the sleeves together, but further serves to support areas of the shoulders and torso of the body, as well. Furthermore, intermediate framework 1630 preferably defines permanent openings therein and is formed from elastically stretchable portions, just as frameworks 1610,1620.

The Seventeenth Embodiment of a Support

A seventeenth embodiment 17000 of a support is illustrated in FIG. 46 and includes an elastically stretchable framework 1710,1720, each of which is permanently attached to a respective sleeve of the pants. Furthermore, this embodiment 17000 includes an intermediate framework 1730 that extends between the sleeves of the pants to join to two frameworks 1710,1720 together. The intermediate framework further serves to support additional areas of the body, including areas of the hips and buttocks. Framework 1730 also preferably defines permanent openings therein, and is formed from elastically stretchable portions, just as frameworks 1710,1720.

The Eighteenth Embodiment of a Support

An eighteenth embodiment 18000 of a support is illustrated in FIG. 47 and represents the embodiment of FIG. 45 and the embodiment of FIG. 46, wherein the frameworks of these two embodiments are joined together and the shirt and pants are integrally manufactured to form a jumpsuit.

The Nineteenth Embodiment of a Support

Figure 48:
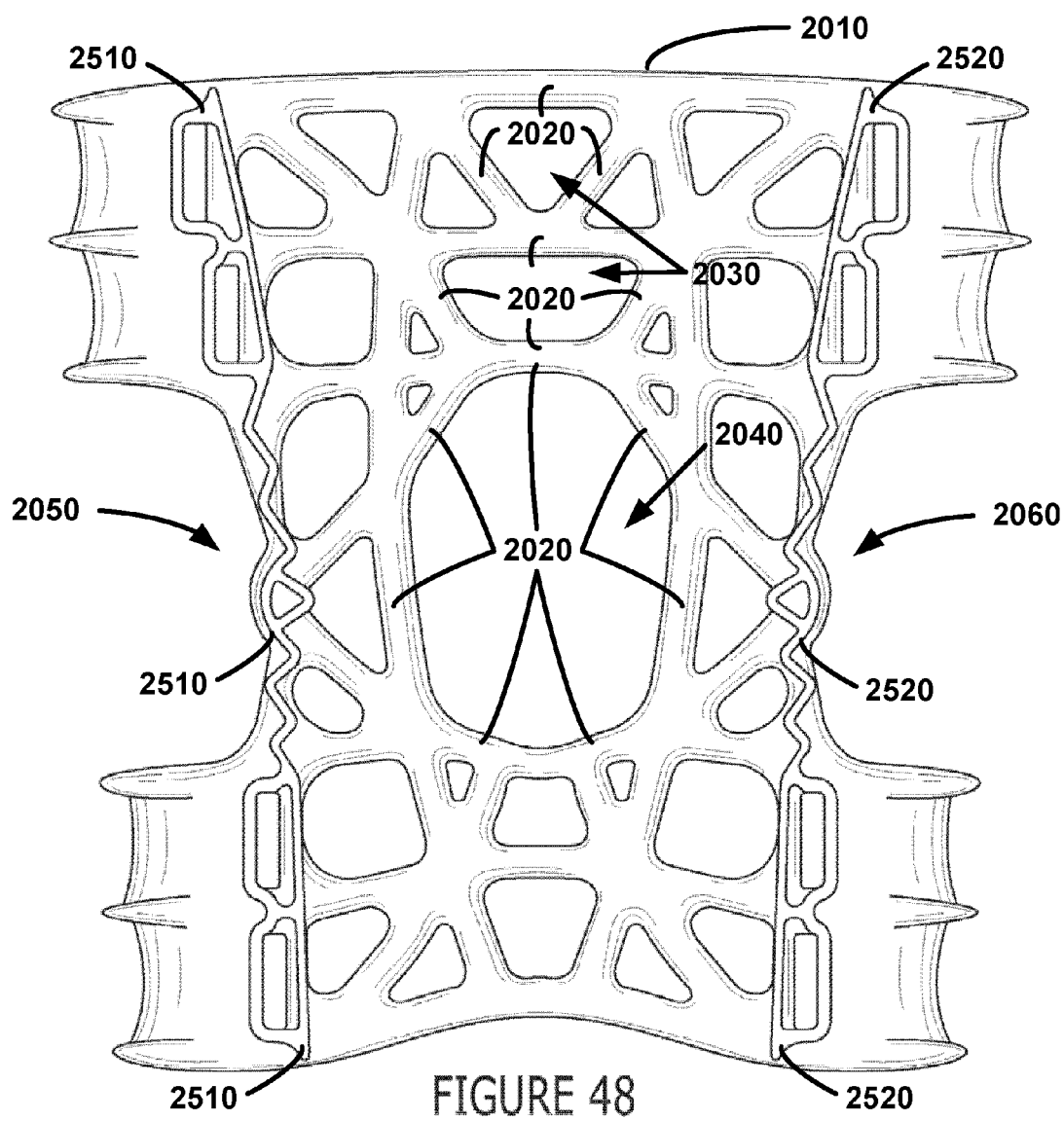
FIG. 48 is a front elevational view of a framework of a nineteenth support in accordance with an aspect of the invention, which nineteenth support is shown in FIG. 54.
Figure 49:
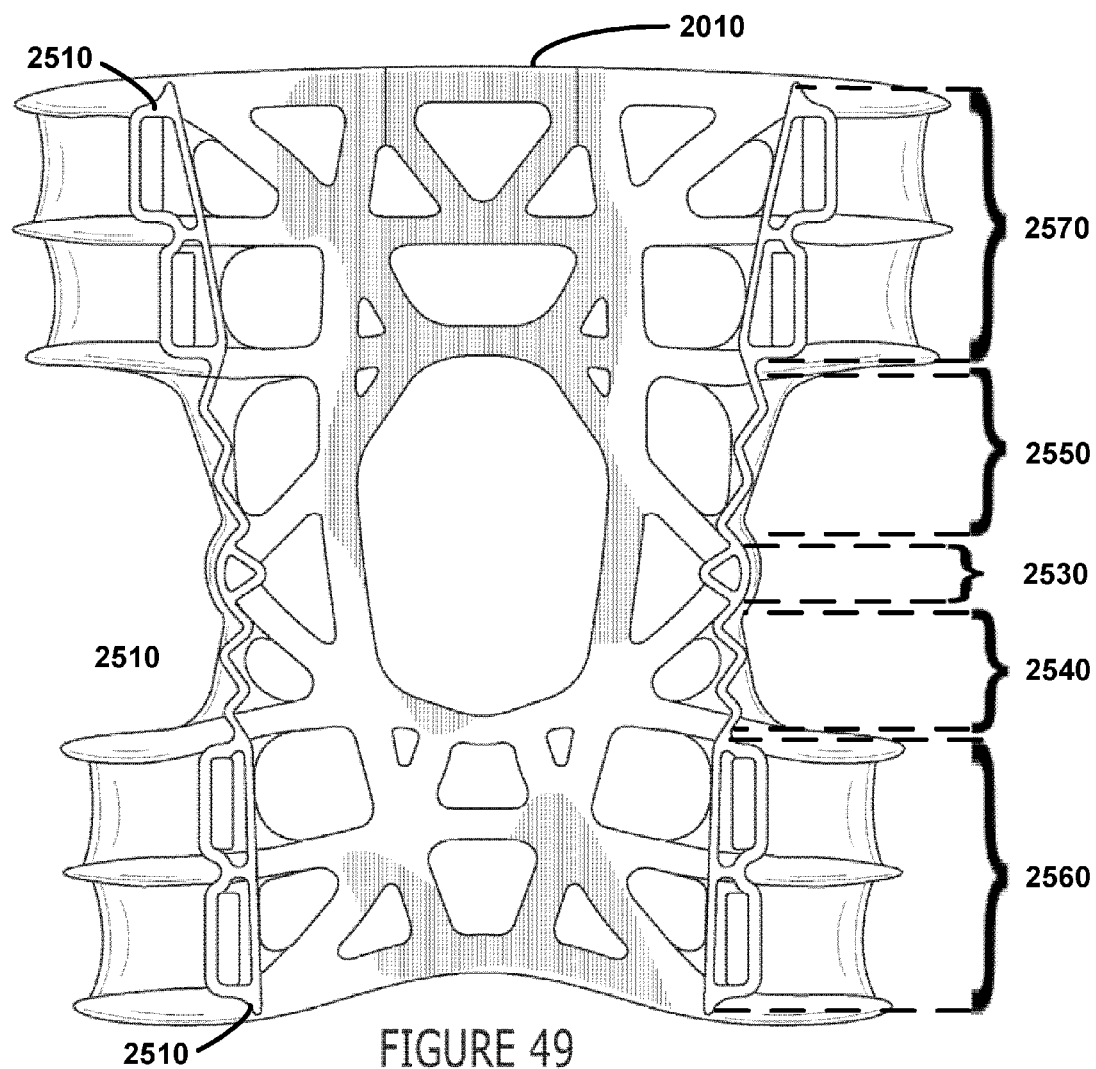
FIG. 49 is a rear elevational view of the framework of FIG. 48.
Figure 50:
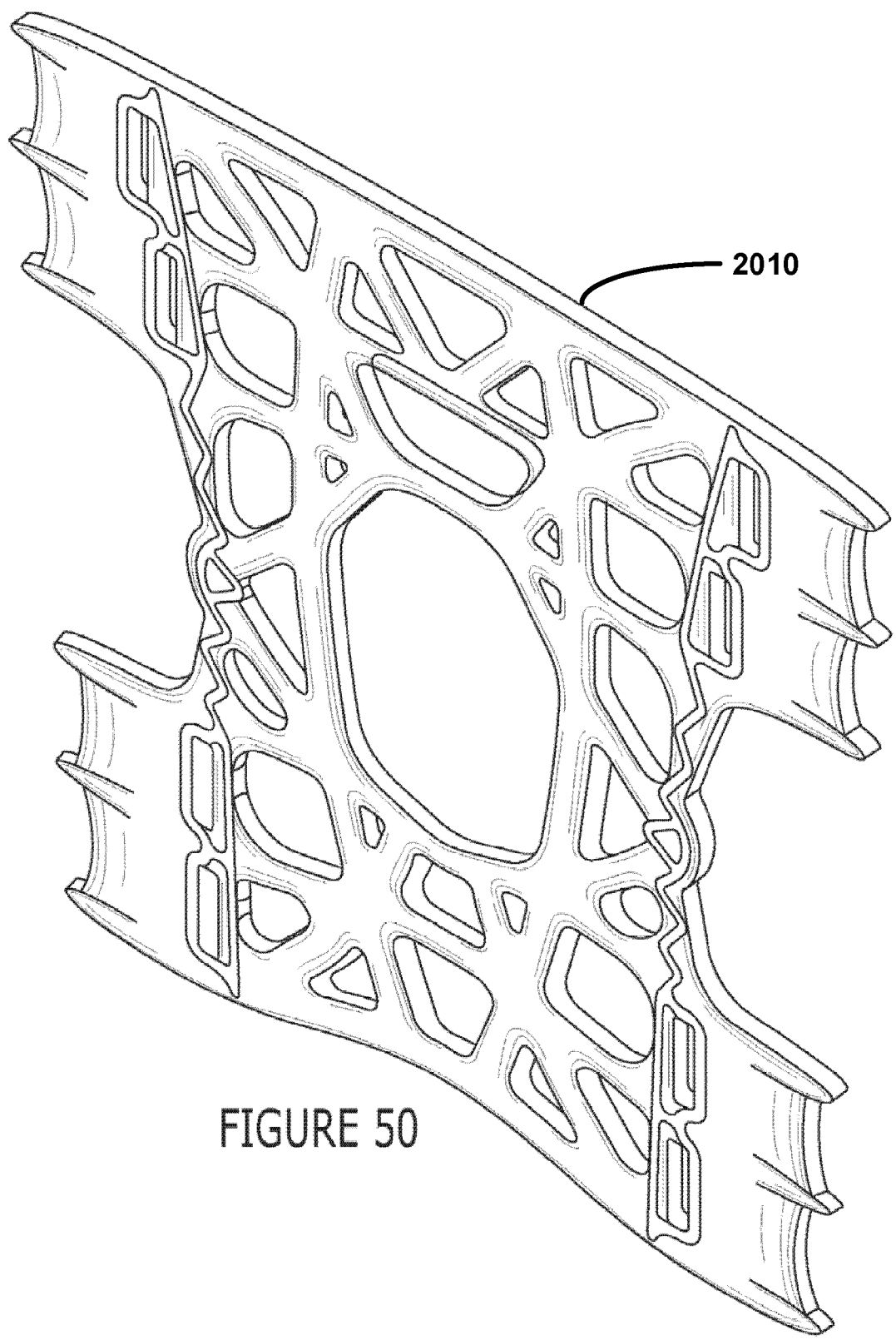
FIG. 50 is an isometric view of the front of the framework of FIG. 48.
Figure 51:
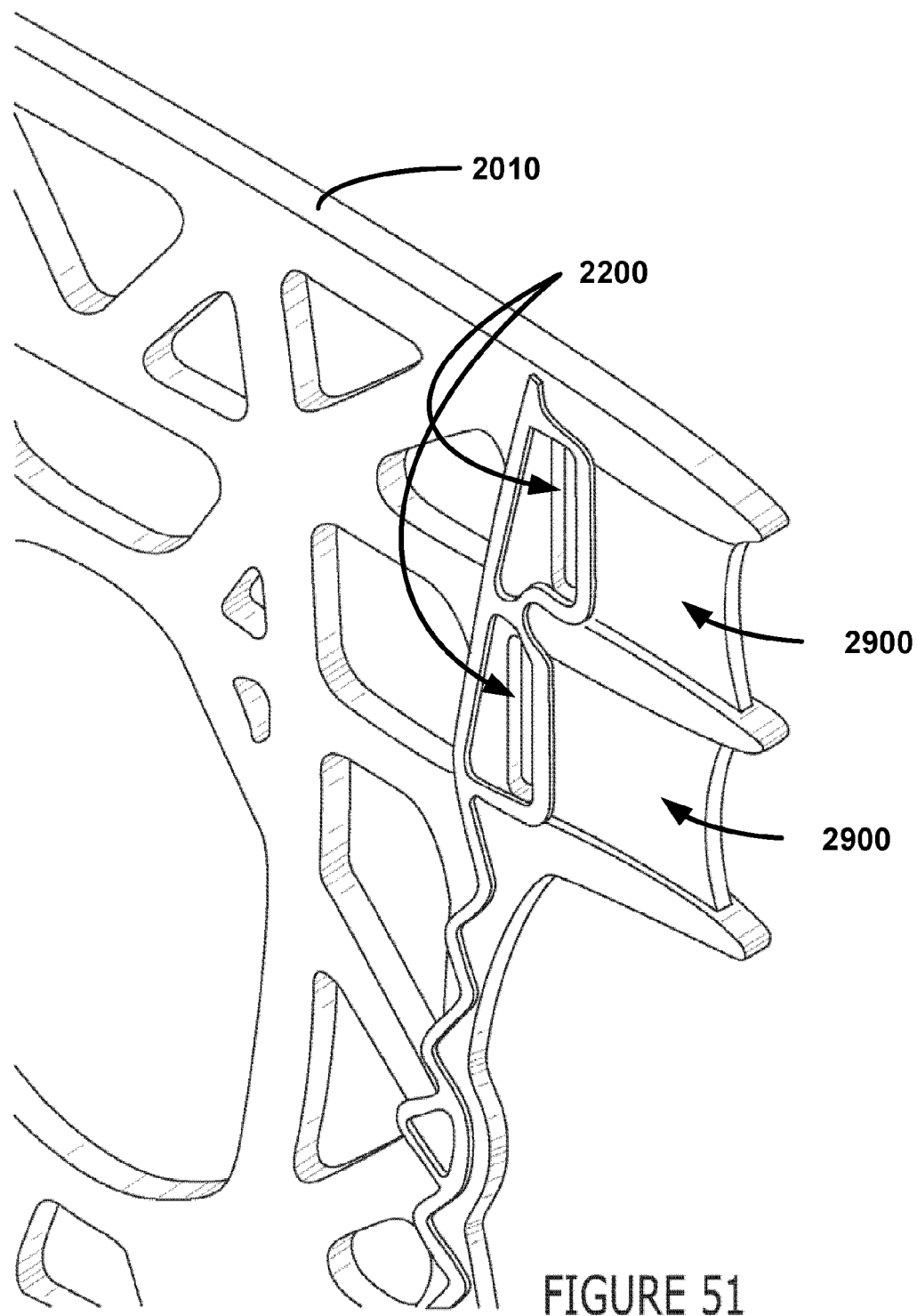
FIG. 51 is an enlarged view of a portion of the front of the framework of FIG. 48.
Figure 52:
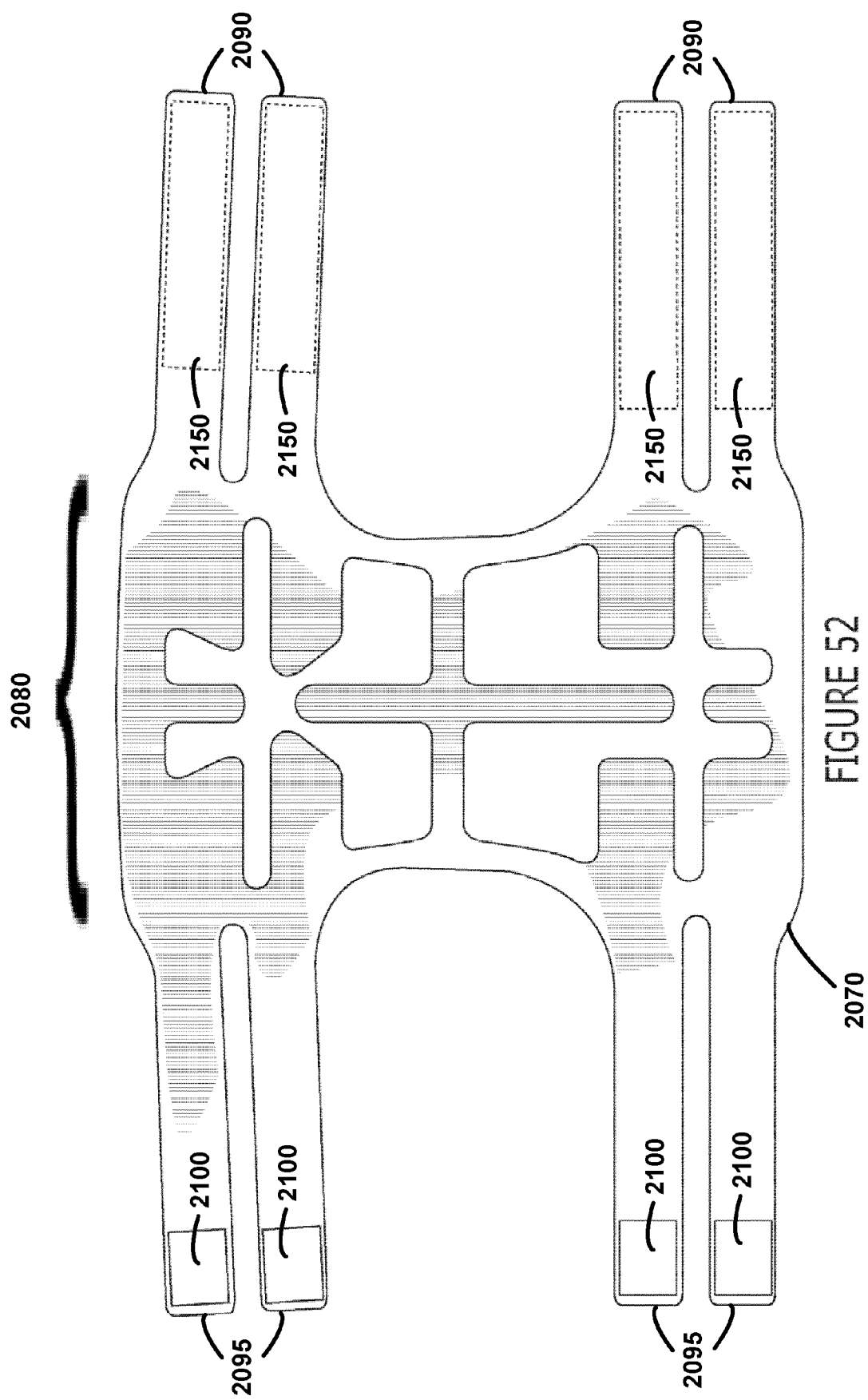
FIG. 52 is an elevational view of the front of a fastening mechanism of the nineteenth support shown in FIG. 54.

With regard to the nineteenth embodiment of a support for an area of a body as shown in FIG. 54, a component thereof comprising a flexible and elastically stretchable framework 2010 is shown in further detail in FIGS. 48-51. With reference to FIG. 48, the framework 2010 comprises generally linear segments or members that are interconnected to define a plurality of permanent openings that extend completely through the framework. Exemplary interconnected members 2020 and permanent openings 2030 defined thereby are illustrated in FIG. 48.

Furthermore, some of these openings 2030 are completely bounded by the interconnected members 2020, and the interconnected members 2020 defining such an opening constitute a portion of the framework 2010 that is stretchable and recoverable about the entire boundary of the opening with the framework 2010. Moreover, the openings 2030 are permanent and exist regardless of whether the framework 2010 actually is disposed in abutment with the body due to the permanent interconnection of the members 2020 defining the openings 2030.

The framework 2010 preferably is formed from an elastomeric material in a conventional molding process and, in this particular embodiment, the framework 2010 resembles a web. Furthermore, the framework preferably includes no internal cavities or pockets of either fluid or gas, i.e., the interconnected members 2020 of the framework 2010 preferably have solid cross-sections.

An alignment opening 2040 defined and bounded completely by interconnected members 2020 of the framework 2010 is dimensioned and shaped specifically to receive a joint protuberance of the body. For example, insofar as the framework 2010 is adapted to abut a lower thigh and upper calf of a human leg, the alignment opening 2040 is shaped to receive the patella of the knee of the leg. For further example, insofar as a framework of the present invention is adapted for the surface thereof to abut an upper arm and forearm, an alignment opening thereof is shaped to receive an elbow. The alignment opening 2040 is symmetrically disposed about an axis of the framework 2010 and is disposed generally equidistant from opposite sides 2050,2060 of the framework 2010, which sides extend generally parallel to the axis.

As will be appreciated from these figures, the framework 2010 is positioned to span a knee joint of the body. Furthermore, because at least portions of the framework 2010 are elastically stretchable, flexing of the knee from a straightened position results in the expansion of the framework 2010 and storage of potential energy therein that is released as kinetic energy when the knee is returned to the straightened position. In this regard, the nineteenth embodiment of the support of the present invention is not an immobilizing support but, instead, is a potentiating support for the area of the body including the knee joint.

As further illustrated with reference to FIG. 48, the nineteenth embodiment of the support of the present invention further includes strut members 2510,2520 that extend generally along adjacent respective, opposite sides 2050,2060 of the framework 2010. Each strut member 2510,2520 is formed integrally with and embedded within the framework 2010 and, preferably, is molded from an elastomeric material having a greater degree of rigidity than the elastomeric material from which the framework 2010 is molded. As further illustrated in FIG. 49, the strut members 2510,2520 extend through the framework 2010 and are visible from both the front and rear views of the framework 2010, the framework 2010 preferably having been molded about preformed strut members 2050,2060 in a multi-step injection molding process. Each strut member 2510,2520 thereby serves to provide a degree of rigidity to the two sides 2050,2060 of the framework 2010, i.e., provides a measure of rigidity along the perimeter sides 2050,2060 extending in the direction of the length of the strut members. Furthermore, each strut member 2510,2520 preferably includes a configuration that varies along the respective strut member for providing varying degrees of flexibility and rigidity to the framework 2010.

In this regard, each strut member preferably includes a middle portion 2530 having a triangular configuration that is more rigid, respectively, than adjacent portions 2540,2550 of the strut member, whereby a double-hinge is formed at the junctions of the middle portion 2530 with the adjacent portions 2540,2550. Moreover, the middle portion 2530 is located proximate the intended location of a hinge joint when the support is donned whereby the double-hinge operates adjacent the body's hinge joint. The design of the double-hinge in the strut member is believed to better enable the support to remain correctly positioned with respect to the body's hinge joint during extension and contraction thereof.

In order to increase the relative differences in rigidity between the middle portion 2530 and the adjacent portions 2540,2550 of each strut member, the configuration of the adjacent portions 2540,2550 includes a zig-zag configuration that promotes bending of the sides of the support in the direction of bending movement of the hinge joint of the body that is spanned, but that resists bending in a direction transverse thereto. Furthermore, these adjacent portions 2540,2550 of each strut member preferably do not extend to the ends of the strut members but, rather, only serve to connect end portions 2560,2570 of each strut member to the middle portion of the strut member, and the end portions 2560,2570 preferably exhibit yet even greater resistance to bending in all directions than the adjacent portions 2540, 2550. Moreover, as shown, the end portions 2560,2570 of each strut members encircle and further define openings through which the fastening mechanism extends for tensioning of the framework 2010, as discussed in greater detail below.

As will be evident from the drawings, each strut member 2510,2520 is located along the axial extent at opposite sides 2050,2060 of the framework 2010 so as to span the hinge joint of the knee, with the middle portion of each strut member being disposed proximate the hinge axis of the knee. Each strut member 2510,2520 and, in particular, the adjacent portions 2540,2550 on either side of the middle portion 2530, preferably is expandable and recoverable between a first initial state and extended states wherein, when expanded to an extended state during flexing of the knee joint, the strut member stores potential energy that is released as kinetic energy upon return of the strut member to the initial state. Thus, the nineteenth embodiment of the support of the present invention further comprises a potentiating support for the area of the body, including the knee joint, for this reason as well.

Another component of the nineteenth embodiment of the support as shown in FIG. 54 comprises a fastening mechanism 2070. The fastening mechanism is illustrated in greater detail in FIG. 52 and includes a middle portion 2080 that is designed for disposition between the framework 2010 and the body when the support is donned to thereby serve as a liner for the framework 2010. The fastening mechanism further includes fastening straps 2090,2095 that are integrally formed with the middle portion 2080. Straps 2090 include areas of loops 2150 for engaging hooks, and straps 2095 include areas of hooks for engaging the area of the loops 2150 in hook-and-loop couplings. Accordingly, the fastening mechanism may be securely attached to a portion of a body by completely encircling the body with the straps 2090,2095 and the coupling of the straps 2090,2095 in hook-and-look engagements.

Moreover, the framework 2010 of the support is securely attached to the portion of the body in this manner by first passing of the straps 2090,2095 through openings 2200 (FIG. 51) defined by the framework 2010 and end portions of the strut members as show in FIG. 54. Additionally, grooves 2900 are provided that are integrally formed with the framework 2010 for receiving the straps in their extension immediately from these openings 2200. It further will be appreciated that by utilizing the fastening mechanism 2070 of the support, the framework 2010 can be tensioned in its abutment with the body and, moreover, the tension with which the surface of the framework is disposed in abutment with the area of the body to be supported can be adjusted as desired.

When donned, the support serves as an exoskeleton of the body, at least in the supported area of the body. In this regard, with the support donned, each of the fastening straps 2090, 2095 may be individually grasped and manually pulled at desired levels of tension. Alternatively, the fastening mechanism shown with regard to the third embodiment of the support of the present invention may be utilized with the framework 2010, with the simple modification that each claw member include only two fastening belts rather than three fastening belts as shown in FIG. 10.

A variation of the framework 2010 also is shown in FIG. 53. The framework 3010 of FIG. 53 is substantially the same as the framework 2010 except for interconnected members 3020 that span what otherwise would be the alignment opening 2040 of framework 2010. These interconnected members preferably are stretchable and recoverable and substantially the same as the interconnected members defining framework 2010, e.g., interconnected members 2020.

Preferred Manufacturing Method

The supports of the invention and, in particular, the embodiments collectively shown in FIGS. 1-39 and 48-54, preferably are manufactured in injection molding processes, whereby the various components of each embodiment of the support, including, inter alia, the framework and strut members, are integrally formed from elastomeric materials. The injection molding processes preferably comprise, for each support, multi-step injection molding, whereby each component can be formed from different elastomeric materials having different elastic stretchability even though the components are integrally constructed. In particular, the strut members can be formed through injection molding of a first elastomeric material, and then the framework can be formed through injection molding of a second elastomeric material about the strut members. This is particularly useful in manufacturing embodiments having strut members that are intended to provide a degree of rigidity to side areas of the framework. This process further results in the appearance of a singularly molded framework having the aforementioned aspects of the invention that can be readily made in efficient and cost effective manner.

What is claimed is:

1. A support for an area of a body that includes a hinge joint, comprising:
   (a) a flexible, elastically stretchable framework configured to extend across the hinge joint of the area of the body, wherein said framework comprises an integrally molded network of interconnected, elongate elastomeric segments, and includes:
      (i) left and right sides comprising first and second exterior lateral segments and top and bottom sides comprising first and second exterior transverse segments, which left, right, bottom and top sides collectively define a perimeter of the framework, (ii) first, second, third, and fourth interior, mutually exclusive subsets of transverse segments, each of which extends between and interconnects the left and right sides of the perimeter of the framework, (iii) first and second interior, mutually exclusive subsets of lateral segments, each of which extends between and interconnects the top side of the perimeter of the framework and the second interior subset of transverse segments, and each of which intersects and interconnects the first interior subset of transverse segments, and (iv) third and fourth interior, mutually exclusive subsets of lateral segments, each of which extends between and interconnects the bottom side of the perimeter of the framework and the second interior subset of transverse segments, and each of which intersects and interconnects the third and fourth interior subsets of transverse segments, (v) wherein each subset of segments comprises one or more segments; and (b) a pair of double-hinge mechanisms, each double-hinge mechanism at least partially embedded in a material of the framework proximate a respective one of said left and right sides of the framework and each double-hinge mechanism including a middle component and end components connected to the middle component on opposite sides of the middle component such that each end component is rotatable between different angles relative to the middle component;

(c) wherein the middle component of the double-hinge mechanism is configured to extend with the framework across the hinge joint, whereby the double-hinge mechanism is operable adjacent, and on opposite sides of, the hinge joint of the body.

2. The support of claim 1, wherein the material of the framework encompasses and completely encircles at least a portion of the middle component.

3. The support of claim 1, wherein each of the end components defines at least one opening therein configured to receive therethrough a strap for attachment of the framework to the body on a respective one of the opposite sides of the hinge joint.

4. The support of claim 3, wherein the framework further defines at least one opening commensurate with one of the openings defined by the end components.

5. The support of claim 3, wherein the framework further defines a groove for guiding of a strap that is received through one of the openings defined by the end components.

6. The support of claim 1, wherein the framework comprises an elastomeric material.

7. The support of claim 6, wherein the framework is configured to be stretched and tensioned into abutment with the area of the body such that the framework conforms to the shape and contour of the area of the body when stretched and tensioned, the framework having a relaxed state when not stretched and tensioned in which the framework does not conform to the shape and contour of the area of the body.

8. The support of claim 6, wherein the framework is in a first configuration when the double-hinge mechanism is in a first position, and the framework is in a second configuration when the double-hinge mechanism is in a second position, the framework storing potential energy that is released as kinetic energy upon transitioning of the double-hinge mechanism from the second position to the first position.

9. The support of claim 1, wherein each double-hinge mechanism is visible from both a front side and a rear side of the framework.

10. The support of claim 1, wherein the framework defines an alignment opening that is dimensioned and shaped to receive a joint protuberance of the hinge joint of the body.

11. The support of claim 10, wherein the alignment opening is symmetrically located relative to the side edges of the framework.

12. The support of claim 10, wherein the alignment opening is dimensioned and shaped to receive a patella of a knee.

13. The support of claim 10, wherein the alignment opening is dimensioned and shaped to receive an elbow.

14. The support of claim 1, wherein the middle component and the end components of each double-hinge mechanism are, respectively, middle and end portions of a single molded piece, wherein the single molded piece comprises first and second adjacent portions each respectively connecting one of the end portions to the middle portion, and wherein each of the middle portion and the end portions of the double-hinge mechanism is more rigid than each of the adjacent portions of the double-hinge mechanism, whereby each end portion is adjustable between different angles relative to the middle portion.

15. The support of claim 14, wherein the framework is molded from an elastomeric material, and wherein the end portions, the middle portion, and the intermediate portions of each of the double-hinge mechanisms is molded from elastomeric material having a greater degree of rigidity than that of the elastomeric material from which the framework is molded.

16. The support of claim 14, wherein the middle portion of each double-hinge mechanism includes a triangular configuration that provides rigidity to the middle portion against bending of the middle portion.

17. The support of claim 14, wherein each intermediate portion of each double-hinge mechanism includes a zig-zag configuration that promotes bending of the intermediate portion.

18. The support of claim 14, wherein each adjacent portion is expandable and recoverable between a respective first initial state and extended states, wherein, when expanded to an extended state, the adjacent portion stores potential energy that is released as kinetic energy upon return of the intermediate portion to the respective first initial state.

19. A method for supporting an area of a body that includes a hinge joint, comprising:

(a) providing a support including, (i) a flexible, elastically stretchable framework configured to extend across the hinge joint of the area of the body, wherein the framework comprises an integrally molded network of interconnected, elongate elastomeric segments, and includes:

(A) left and right sides comprising first and second exterior lateral segments and top and bottom sides comprising first and second exterior transverse segments, which left, right, bottom and top sides collectively define a perimeter of the framework, (B) first, second, third, and fourth interior, mutually exclusive subsets of transverse segments, each of which extends between and interconnects the left and right sides of the perimeter of the framework, (C) first and second interior, mutually exclusive subsets of lateral segments, each of which extends between and interconnects the top side of the perimeter of the framework and the second interior subset of transverse segments, and each of which intersects and interconnects the first interior subset of transverse segments, and (D) third and fourth interior, mutually exclusive subsets of lateral segments, each of which extends between and interconnects the bottom side of the perimeter of the framework and the second interior subset of transverse segments, and each of which intersects and interconnects the third and fourth interior subsets of transverse segments, (E) wherein each subset of segments comprises one or more segments, and (ii) a pair of double-hinge mechanisms, each double-hinge mechanism at least partially embedded in a material of the framework proximate a respective one of the left and right sides of the framework and each double-hinge mechanism including a middle component and end components connected to the middle component on opposite sides of the middle component such that each end component is rotatable between different angles relative to the middle component; and (b) positioning the support against the body such that the middle components of the pair of double-hinge mechanisms extend with the framework across the hinge joint of the body, whereby each of the pair of double-hinge mechanisms is operable adjacent, and on opposite sides of, the hinge joint of the body, said step of positioning the support including tensioning the framework in abutment with the area of the body including the hinge joint and fastening the support to the body on opposite sides of the hinge joint of the body such that the framework is held in tension in its abutment with the area of the body, the flexible, elastically stretchable framework conforming to the surface contour of the area of the body as a result of the tensioning.

* * * * *